(12) United States Patent
Arimilli et al.

(10) Patent No.: US 6,451,340 B1
(45) Date of Patent: Sep. 17, 2002

(54) NUCLEOTIDE ANALOG COMPOSITIONS

(75) Inventors: Murty N. Arimilli, Fremont; Daphne E. Kelly, San Francisco; Thomas T. K. Lee, Redwood City; Lawrence V. Manes, Moss Beach; John D. Munger, Jr., Alviso; Ernest J. Prisbe, Los Altos; Lisa M. Schultze, San Carlos, all of CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/950,031

(22) Filed: Sep. 10, 2001

Related U.S. Application Data

(63) Continuation of application No. 09/121,163, filed on Jul. 23, 1998, now abandoned.
(60) Provisional application No. 60/053,771, filed on Jul. 25, 1997.

(51) Int. Cl.[7] .................................................. A61K 9/20
(52) U.S. Cl. ...................... 424/464; 424/465; 424/489; 514/449
(58) Field of Search ................................ 424/464, 465, 424/489; 514/449

(56) References Cited

U.S. PATENT DOCUMENTS

| | | | |
|---|---|---|---|
| 4,476,248 A | 10/1984 | Gordon et al. | |
| 5,663,159 A | 9/1997 | Starrett, Jr. et al. | 514/181 |
| 5,795,909 A * | 8/1998 | Shashoua et al. | 514/449 |
| 2002/0035085 A1 * | 3/2002 | Sommadossi et al. | 514/45 |

FOREIGN PATENT DOCUMENTS

| | | |
|---|---|---|
| EP | 0 481 214 A1 | 4/1992 |
| EP | 0 632 048 A1 | 6/1994 |
| EP | 0 647 649 A1 | 4/1995 |
| WO | WO 92/09611 | 6/1992 |
| WO | WO 00/16755 A2 * | 3/2000 ......... A61K/31/00 |

OTHER PUBLICATIONS

Benzaria et al., "New Prodrugs of 9-(2-Phosphonomethoxyethyl) Adenine [PMEA]: Synthesis and Stability Studies", 14(3–5):563–565, NUCLS & NUCLT, 1995.

Berge et al., "Pharmaceutical Salts", 66(1):1–19, J Pharm Sci, Jan. 1977.

Cundy et al., "Oral bioavailability of the antiretroviral agent 9-(2-phosphonylmethoxyethyl)adenine (PMEA) from three formulations of the prodrug bis(pivaloyloxymethyl)–PMEA in fasted male cynomolgus monkeys", 11(6):839–843, Pharm Res, 1994.

Gordon et al., "Common Solvents for Crystallization", pp. 442–443, The Chemist's Companion, 1972.

Iyer et al., "Synthesis of Acyloxyalkyl Acylphosphonates as Potential Prodrugs of the Antiviral, Trisodium Phosphonoformate (Foscarnet Sodium)", 30(51):7141:7144, Tet Lett, 1989.

Landgrebe, John A., "Crystallization and Filtration", 3rd edition, pp. 65–77, Theory and Practice in the Organic Laboratory, 1982.

Lee et al., "Characterization of the Thermal Decomposition of Adefovir Dipivoxil in the Solid State", Poster, AAPS, Apr. 24 & 25, 1997.

MIT Student Manual, "Purification of Solids", Chapter 5, pp. 1–18, (precedes filing date).

(List continued on next page.)

Primary Examiner—Thurman K. Page
Assistant Examiner—Robert M. Joynes
(74) Attorney, Agent, or Firm—Max D. Hensley

(57) ABSTRACT

The invention provides crystalline forms of adefovir dipivoxil and methods to prepare the crystals. The compositions and methods of the present invention have desirable properties for large scale synthesis of crystalline adefovir dipivoxil or for its formulation into therapeutic dosages. Invention compositions include an anhydrous crystal form of adefovir dipivoxil.

47 Claims, 29 Drawing Sheets

OTHER PUBLICATIONS

Munzel, K., "Der Einfluss der Formgebung auf die Wirkung eines Arzneimittels", 14:309–321, Ritte Der Arzneimittelforschung, 1970.

Myerson, Allan S. (editor), "Solutions and Solution Properties", p. 1–165, Handbook of Industrial Crystallization, 1993.

Serafinowska et al., "Synthesis and in Vivo Evaluation of Prodrugs of 9-[2-(Phosphonomethoxy)ethoxy]adenine", 38:1372–1379, J Med Chem, 1995.

Starrett et al, "Synthesis and in vitro evaluation of a phosphonate prodrug: bis(pivaloyloxymethyl) 9-(2-phosphonylmethoxyethyl)adenine", 19:267–273, Antiviral Res, 1992.

Starrett et al., "Synthesis, Oral Bioavailability Determination, and in Vitro Evaluation of Prodrugs of the Antiviral Agent 9-[2-(Phosphonomethoxy)ethyl]adenine (PMEA)", 37:1857–1864, J Med Chem, 1994.

* cited by examiner (a) Observed:

(b) Calculated:

NUCLEOTIDE ANALOG COMPOSITIONS

CROSS-REFERENCE TO RELATED APPLICATIONS

This application is a continuation of application Ser. No. 09/121,163, filed Jul. 23, 1998, now abandoned, and a continuation-in-part of provisional application Ser. No. 60/053,771, filed Jul. 25, 1997, now abandoned.

BACKGROUND OF THE INVENTION

The invention relates to the nucleotide analog 9-[2-[[bis[(pivaloyloxy)methoxy]phosphinyl]methoxy]ethyl]adenine ("adefovir dipivoxil" or "AD") and to its use. The present invention also relates to methods to synthesize AD.

AD is the bis-pivaloyloxymethyl ester of the parent compound 9-[2-(phosphonomethoxy)ethyl]adenine ("PMEA"), which has antiviral activity in animals and in humans. AD and PMEA have been described, e.g., U.S. Pat. Nos. 4,724,233 and 4,808,716, EP 481 214, Benzaria et al., *Nucleosides and Nucleotides* (1995) 14(3–5):563–565, Holy et al., *Collect. Czech. Chem. Commun.* (1989) 54:2190–2201, Holy et al., *Collect. Czech. Chem. Commun.* (1987) 52:2801–2809, Rosenberg et al., *Collect. Czech. Chem. Commun.* (1988) 53:2753–2777, Starrett et al., *Antiviral Res.* (1992) 19:267–273; Starrett et al., *J. Med. Chem.* (1994) 37:1857–1864. Heretofore, AD has been provided only as a noncrystalline or amorphous form. It has not been reported to have been prepared as a crystalline material.

Methods for crystallizing organic compounds per se are described in J. A. Landgrebe, *Theory and Practice in the Organic Laboratory,* 2nd edition, 1977, D.C. Heath and Co., Lexington, Mass., p. 43–51; A. S. Myerson, *Handbook of Industrial Crystallization,* 1993, Butterworth-Heinemann, Stoneham, Mass., p. 1–101).

OBJECTS OF THE INVENTION

The invention provides one or more compositions or methods that meet one or more of the following objects.

A principal object of the invention is to provide compositions comprising novel AD forms having desirable properties for large scale synthesis or for formulation into therapeutic dosages.

Another object is to provide AD having good melting point, and/or flow or bulk density properties, which facilitates manufacturing and formulation of compositions containing AD.

Another object is to provide storage-stable forms of AD.

Another object is to provide AD which can be readily filtered and easily dried.

Another object is to provide highly purified AD having at least about 97% (w/w) purity and preferably at least about 98%.

Another object is to eliminate or minimize by-products made during AD synthesis.

Another object is to provide a method for purifying AD that avoids expensive and time-consuming column chromatography.

SUMMARY OF THE INVENTION

The invention accomplishes its primary objects by providing crystalline AD, in particular, an anhydrous crystalline form (hereafter "Form 1"), a hydrated form, $C_{20}H_{32}N_5O_8P_1 \cdot 2H_2O$, (hereafter "Form 2"), a methanol solvate form, $C_{20}H_{32}N_5O_8P_1 \cdot CH_3OH$, (hereafter "Form 3"), a fumaric acid salt or complex, $C_{20}H_{32}N_5O_8P_1 \cdot C_4H_4O_4$ (hereafter "Form 4"), a hemisulfate salt or complex, a hydrobromide salt or complex, a hydrochloride salt or complex, a nitrate salt or complex, a mesylate ($CH_3SO_3H$) salt or complex, an ethyl sulfonate salt ($C_2H_5SO_3H$) or complex, a β-naphthylene sulfonic acid salt or complex, an α-naphthylene sulfonic acid salt or complex, an (S)-camphor sulfonic acid salt or complex, a succinic acid salt or complex, a maleic acid salt or complex, an ascorbic acid salt or complex and a nicotinic acid salt or complex.

Invention embodiments include (1) crystalline Form 1 AD essentially having an X-ray powder diffraction ("XRD") spectrum using Cu—Kα radiation, expressed in degrees 2θ at any one or more (in any combination) of about 6.9, about 11.8, about 12.7, about 15.7, about 17.2, about 20.7, about 21.5, about 22.5, and about 23.3; (2) crystalline Form 2 AD essentially having an XRD spectrum using Cu—Kα radiation, expressed in degrees 2θ at any one or more (in any combination) of about 8.7–8.9, about 9.6, about 16.3, about 18.3, about 18.9, about 19.7, about 21.0, about 21.4, about 22.0, about 24.3, about 27.9, about, 30.8, and about 32.8; (3) crystalline Form 3 AD essentially having an XRD spectrum using Cu—Kα radiation, expressed in degrees 2θ at any one or more (in any combination) of about 8.1, about 8.7, about 14.1, about 16.5, about 17.0, about 19.4, about 21.1, about 22.6, about 23.4, about 24.2, about 25.4, and about 30.9; and crystalline Form 4 AD essentially having an XRD spectrum using Cu—Kα radiation, expressed in degrees 2θ at any one or more (in any combination) of about 9.8, about 15.2, about 15.7, about 18.1, about 18.3, about 21.0, about 26.3 and about 31.7.

Invention embodiments include AD crystals having the crystal morphologies shown in any one or more of FIGS. 4–10.

In other embodiments, the invention provides methods to produce AD crystals by allowing crystals to form from a crystallization solution comprising about 6–45% AD and about 55–94% crystallization solvent wherein the crystallization solvent is selected from the group consisting of (1) a mixture between about 1:10 v/v to about 1:3 v/v of acetone:di-n-butyl ether, (2) a mixture between about 1:10 v/v to about 1:3 v/v of ethyl acetate:di-n-propyl ether, (3) a mixture between about 1:10 v/v to about 10:1 v/v of t-butanol:di-n-butyl ether, (4) a mixture between about 1:10 v/v to about 1:3 v/v of methylene chloride:di-n-butyl ether, (5) a mixture between about 1:10 v/v to about 10:1 v/v of diethyl ether:di-n-propyl ether, (6) a mixture between about 1:10 v/v to about 1:3 v/v of tetrahydrofuran:di-n-butyl ether, (7) a mixture between about 1:10 v/v to about 1:3 v/v of ethyl acetate:di-n-butyl ether, (8) a mixture between about 1:10 v/v to about 1:3 v/v of tetrahydropyran:di-n-butyl ether, (9) a mixture between about 1:10 v/v to about 1:3 v/v of ethyl acetate:diethyl ether, (10) t-butyl-methyl ether, (11) diethyl ether, (12) di-n-butyl ether, (13) t-butanol, (14) toluene, (15) isopropyl acetate, (16) ethyl acetate, (17) a mixture consisting essentially of (A) a first crystallization solvent consisting of a first dialkyl ether of the formula $R^1$—O—$R^2$ wherein $R^1$ is an alkyl group having 1, 2, 3, 4, 5 or 6 carbon atoms, $R^2$ is an alkyl group having 2, 3, 4, 5 or 6 carbon atoms or both $R^1$ and $R^2$ are linked together to form a 5-, 6-, 7-, or 8-membered ring, provided that the dialkyl ether is not methyl-ethyl ether, and (B) a second crystallization solvent selected from the group consisting of (a) a second dialkyl ether of the formula $R^1$—O—$R^2$, wherein the second dialkyl ether is different from the first dialkyl ether, but is not methyl ethyl ether, (b) toluene, (c) tetrahydrofuran, (d) t-butanol, (e) ethyl acetate, (f) methylene chloride, (g) propyl acetate and (h) isopropanol.

Invention embodiments include purified crystalline AD (e.g., form 1 and/or form 2). Invention embodiments also include compositions comprising crystalline AD (e.g., form 1 and/or form 2) and one or more compounds, such as pharmaceutical excipients or compounds present in reaction mixtures that contain the crystalline AD.

Invention embodiments include a method to produce AD crystals comprising dissolving AD in methanol and allowing crystals to form.

Another embodiment is crystalline AD suitable for pharmaceutical compositions or uses comprising, e.g., one or more of Form 1, Form 2, Form 3 and/or Form 4 AD and a pharmaceutically acceptable carrier(s) for treating viral conditions for which PMEA is known to be active, such as a retroviral infection (HIV, SIV, FIV) or hepatitis B virus or other hepadnavirus infections, or DNA virus infection (human cytomegalovirus or herpesvirus, e.g., HSV1 or HSV2) in humans or animals.

The invention provides a method to produce crystalline Form 2 AD comprising forming AD crystals in the presence of water.

In another embodiment, a method for preparing AD comprises contacting PMEA with chloromethyl pivalate in N-methylpyrrolidinone (NMP, 1-methyl-2-pyrrolidinone) and a trialkylamine such as triethylamine (TEA) and recovering AD.

In a further embodiment, a PMEA composition containing less than about 2% salt is provided, which may be used in a method comprising contacting PMEA containing less than about 2% salt.

In a further embodiment, an AD product is obtained by a process comprising preparing wet granules from a mixture comprising a liquid, Form 1 adefovir dipivoxil and an acceptable excipient and, optionally drying the wet granules.

BRIEF DESCRIPTION OF THE FIGURES

FIGS. 4–10 are copies of the photographs made at a 128% enlargement.

DETAILED DESCRIPTION OF THE INVENTION

Figure 1:
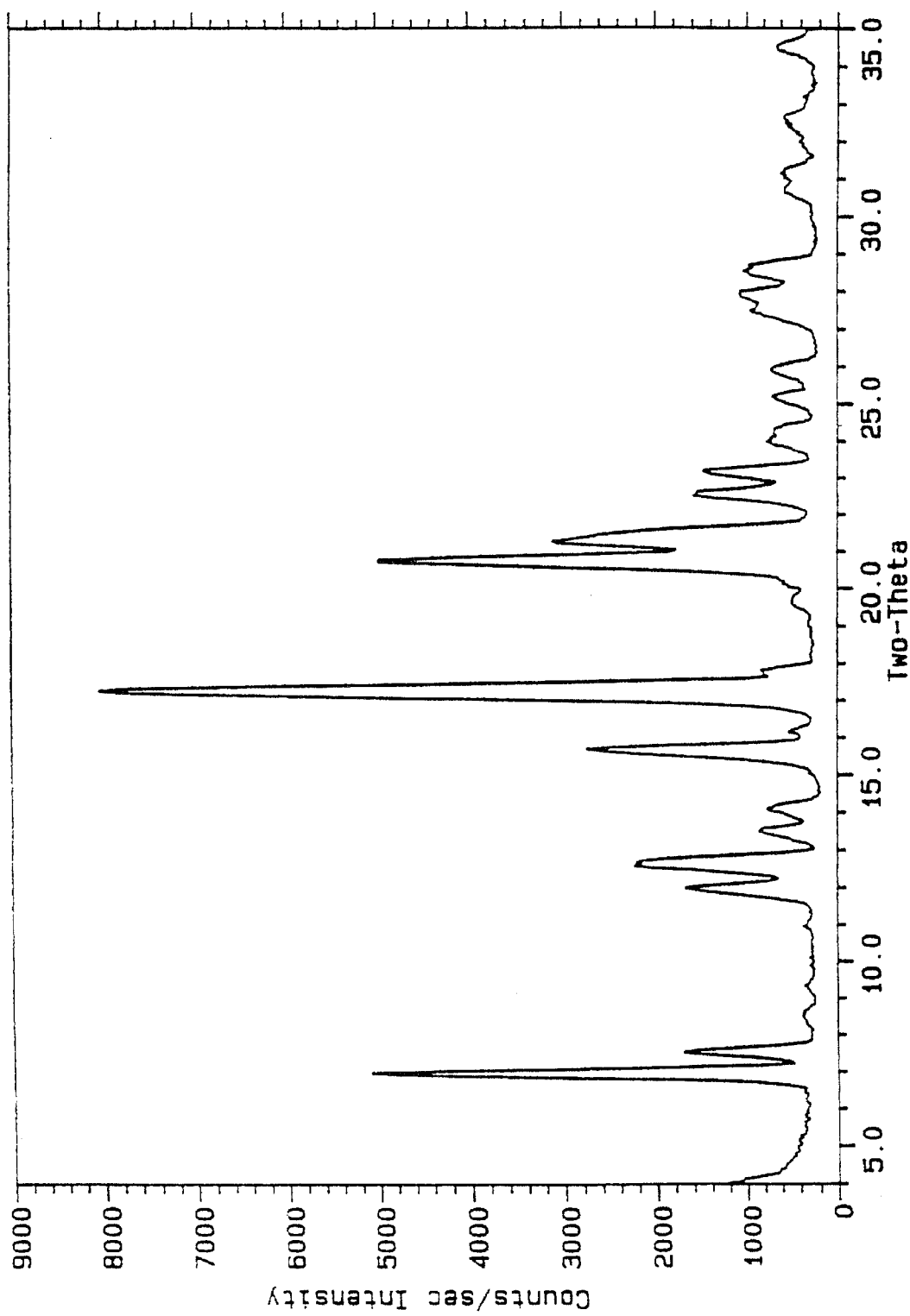
FIG. 1 shows a Form 1 crystal XRD pattern.

Unless otherwise indicated, temperatures are in degrees Celsius (°) Room temperature means about 18–23°.

As used herein, alkyl means linear, branched and cyclic saturated hydrocarbons. "Alkyl" or "alkyl moiety" as used herein, unless stated to the contrary, is a hydrocarbon containing 1, 2, 3, 4, 5, 6, 7, 8, 9, 10, 11 or 12 normal, secondary, tertiary or cyclic structures. The term $C_{1-10}$ alkyl means alkyl groups having 1, 2, 3, 4, 5, 6, 7, 8, 9 or 10 carbon atoms. Examples are —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_2$CH$_3$, —CH(CH$_3$)CH$_2$CH$_2$CH$_3$, —CH(CH$_2$CH$_3$)$_2$, —C(CH$_3$)$_2$CH$_2$CH$_3$, —CH(CH$_3$)CH(CH$_3$)$_2$, —CH$_2$CH$_2$CH(CH$_3$)$_2$, —CH$_2$CH(CH$_3$)CH$_2$CH$_3$, —CH$_2$C(CH$_3$)$_3$, —CH$_2$CH$_2$CH$_2$CH$_2$CH$_3$, —CH(CH$_3$) CH$_2$CH$_2$CH$_2$CH$_3$, —CH(CH$_2$CH$_3$) (CH$_2$CH$_2$CH$_3$), —C(CH$_3$)$_2$CH$_2$CH$_2$CH$_3$, —CH(CH$_3$)CH(CH$_3$)CH$_2$CH$_3$, CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH(CH$_2$CH$_3$)CH(CH$_3$)$_2$, —C(CH$_3$)$_2$CH(CH$_3$)$_2$, —CH(CH$_3$)C(CH$_3$)$_3$, cyclopropyl, cyclobutyl, cyclopropylmethyl, cyclopentyl, cyclobutylmethyl, 1-cyclopropyl-1-ethyl, 2-cyclopropyl-1-ethyl, cyclohexyl, cyclopentylmethyl, 1-cyclobutyl-1-ethyl, 2-cyclobutyl-1-ethyl, 1-cyclopropyl-1-propyl, 2-cyclopropyl-1-propyl, 3-cyclopropyl-1-propyl, 2-cyclopropyl-2-propyl, and 1-cyclopropyl-2-propyl.

"Alkoxide" as used herein, unless stated to the contrary, is a hydrocarbon containing 1, 2, 3, 4, 5 or 6 carbon atoms, as defined herein for alkyl, linked to an oxygen atom. Examples are —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH(CH$_3$)CH$_2$CH$_3$, —OC(CH$_3$)$_3$, —OCH$_2$CH$_2$CH$_2$CH$_2$CH$_3$, —OCH(CH$_3$)CH$_2$CH$_2$CH$_3$, —OCH(CH$_2$CH$_3$)$_2$, —OC(CH$_3$)$_2$CH$_2$CH$_3$, —OCH(CH$_3$)CH(CH$_3$)$_2$, —OCH$_2$CH$_2$CH(CH$_3$)$_2$, —OCH$_2$CH(CH$_3$)CH$_2$CH$_3$, —OCH$_2$C(CH$_3$)$_3$, —OCH(CH$_3$)(CH$_2$)$_3$CH$_3$, —OC(CH$_3$)$_2$(CH$_2$)$_2$CH$_3$, —OCH(C$_2$H$_5$)(CH$_2$)$_2$CH$_3$, —O(CH$_2$)$_3$CH(CH$_3$)$_2$, —(CH$_2$)$_2$C(CH$_3$)$_3$, —OCH$_2$CH (CH$_3$)(CH$_2$)$_2$CH$_3$, and —OCH$_2$CH$_2$CH$_2$CH$_2$CH$_2$CH$_3$.

"Trialkylamine" means an nitrogen atom substituted with three $C_{1-6}$ alkyl moieties, which are independently chosen. Examples are nitrogen substituted with 1, 2 or 3 —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_2$CH$_3$, —CH(CH$_3$)CH$_2$CH$_2$CH$_3$, —CH(CH$_2$CH$_3$)$_2$, —C(CH$_3$)$_2$CH$_2$CH$_3$, —CH(CH$_3$)CH(CH$_3$)$_2$, —CH$_2$CH$_2$CH(CH$_3$)$_2$, —CH$_2$CH (CH$_3$)CH$_2$CH$_3$, —CH$_2$C(CH$_3$)$_3$, —CH$_2$CH$_2$CH$_2$CH$_2$CH$_2$CH$_3$, —CH(CH$_3$)CH$_2$CH$_2$CH$_2$CH$_3$, —CH(CH$_2$CH$_3$)(CH$_2$CH$_2$CH$_3$), —C(CH$_3$)$_2$CH$_2$CH$_2$CH$_3$, —CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH(CH$_2$CH$_3$)CH(CH$_3$)$_2$, —C(CH$_3$)$_2$CH(CH$_3$)$_2$ or —CH(CH$_3$)C(CH$_3$)$_3$ moieties.

"Heteroaryl" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A series of Monographs* (John Wiley & Sons, New York, 1950 to present), in particular Volumes 13, 14, 16, 19, and 28; and *J. Am. Chem. Soc.*, (1960) 82:5566.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, b-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include
2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein, AD that is a "crystalline material", "crystalline" or "crystal" means a solid AD having an ordered arrangement of substantially all of the constituent molecule(s) in a definite three-dimensional spatial pattern or lattice. Crystalline or crystal AD may comprise one or more than one type of composition, e.g., AD.fumaric acid or AD.2H$_2$O. A crystalline material or crystal may occur in one or more than one crystal habits, e.g., tablets, rods, plates or needles.

Unless specified otherwise explicitly or by context, we express percentage amounts as % by weight (w/w). Thus, a solution containing at least about 40% AD is a solution containing at least about 40% w/w AD. Solid AD containing 0.1% water means 0.1% w/w water is associated with the solid.

Crystalline AD substantially free of noncrystalline AD means a solid composition in which more than about 60% of the AD is present in the composition as crystalline material. Such compositions typically contain at least about 80%, usually at least about 90%, of one or more AD crystal forms, with the remaining AD being present as noncrystalline AD.

Invention compositions optionally comprise salts of the compounds herein, including pharmaceutically acceptable salts comprising, for example, an uncharged moiety or a monovalent anion. Salt(s) include those derived by combination of appropriate anions such as inorganic or organic acids. Suitable acids include those having sufficient acidity to form a stable salt, preferably acids of low toxicity. For example, one may form invention salts from acid addition of certain organic and inorganic acids, e.g., HF, HCl, HBr, HI, H$_2$SO$_4$, H$_3$PO$_4$, or from organic sulfonic acids, organic carboxylic acids to basic centers, typically amines. Exemplary organic sulfonic acids include C$_{6-16}$ aryl sulfonic acids, C$_{6-16}$ heteroaryl sulfonic acids and C$_{1-16}$ alkyl sulfonic acids such as phenyl, α-naphthyl, β-naphthyl, (S)-camphor, methyl, ethyl, n-propyl, i-propyl, n-butyl, s-butyl, i-butyl, t-butyl, pentyl and hexyl sulfonic acids. Exemplary organic carboxylic acids include C$_{1-16}$ alkyl, C$_{6-16}$ aryl carboxylic acids and C$_{4-16}$ heteroaryl carboxylic acids such as acetic, glycolic, lactic, pyruvic, malonic, glutaric, tartaric, citric, fumaric, succinic, malic, maleic, hydroxymaleic, benzoic, hydroxybenzoic, phenylacetic, cinnamic, salicylic and 2-phenoxybenzoic. Salts also include the invention compound salts with one or more amino acids. Many amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine. Salts are usually biologically compatible or pharmaceutically acceptable or non-toxic, particularly for mammalian cells. Salts that are biologically toxic are generally used with synthetic intermediates of invention compounds. The salts of AD are typically crystalline, such as Form 4 described herein.

Embodiments include compositions that transiently occur when a method step or operation is performed. For example, when a sodium alkoxide is brought into contact with a 9-(2-hydroxyethyl)adenine solution, the composition at the initiation of mixing will contain negligible amounts of the sodium alkoxide. This composition will be generally be present as a non-homogenous mixture prior to sufficient agitation to mix the solution. Such a composition usually comprises negligible reaction products and comprises mostly reactants. Similarly, as a reaction proceeds, the proportions of reactants, products and by-products will change relative to each other. These transient compositions are intermediates that arise when a process step is performed and they are expressly included as invention embodiments.

Crystalline forms of AD

AD prepared and recovered as described (Starrett et al., *J. Med. Chem.* (1994) 19:1857–1864) and as recovered from a silica gel column in a solution of methanol (about 4%) and methylene chloride (about 96%) by rotary evaporation under reduced pressure at about 35° precipitates as a noncrystalline or an amorphous solid. We now have discovered that AD can be prepared in crystalline form.

We have identified several different crystalline AD forms. We have characterized them by several methods, usually by XRD and DSC thermogram. Workers commonly use XRD to characterize or identify crystal compositions (see, e.g., U.S. Pharmacopoeia, volume 23, 1995, method 941, p 1843–1845, U.S.P. Pharmacopeial Convention, Inc., Rockville, Md.; Stout et al, *X-Ray Structure Determination; A Practical Guide,* MacMillan Co., New York, N.Y. 1968). The diffraction pattern obtained from a crystalline compound is often diagnostic for a given crystal form, although weak or very weak diffraction peaks may not always appear in replicate diffraction patterns obtained from successive batches of crystals. This is particularly the case if other crystal forms are present in the sample in appreciable amounts, e.g., where Form 1 crystals have become partially hydrated to Form 2 crystals. The relative intensities of bands, particularly at low angle X-ray incidence values (low $2\theta$), may vary due to preferred orientation effects arising from differences in, e.g., crystal habit, particle size and other conditions of measurement. Thus, the relative intensities of the diffraction peaks are not conclusively diagnostic of the crystal form in question. Instead, one should look to the relative positioning of the peaks rather than their amplitude to determine if an AD crystal is one of the forms described herein. Individual XRD peaks in different samples are generally located within about 0.3–1 $2\theta$ degree for broad peaks. Broad XRD peaks may consist of two or more individual peaks located closely together. For sharp isolated peaks under reproducible conditions, the peak is usually found within about 0.1 $2\theta$ degrees on successive XRD analyses. Assuming one uses the same instrument to measure a compound's XRD spectrum on successive XRD analyses, the differences in XRD peak locations under typical conditions are due primarily to differences in sample preparation or the purity of the sample itself. When we identify a sharp isolated XRD peak at a given position as being located at, e.g., about 6.9, this means that the peak is at 6.9±0.1. When we identify a broad XRD peak at a given position as being located at about a given $2\theta$ value, this means that the peak is at that $2\theta$ value±0.3.

Note that it is not necessary to rely on all bands that one observes in the highly purified AD reference samples herein; even a single band may be diagnostic of a given crystal form of AD, e.g., 6.9 for Form 1. Identification should focus on band position and general pattern, particularly the selection of bands unique to the various crystal forms.

Additional diagnostic techniques that one can optionally use to identify crystalline AD include differential scanning calorimetry (DSC), melting point measurements and infrared absorption spectroscopy (IR). DSC measures thermal transition temperatures at which a crystal absorbs or releases heat when its crystal structure changes or it melts. Thermal transition temperatures and melting points are typically within about 2° C. on successive analyses, usually within about 1 degree. When we state that a compound has a DSC peak or a melting point at a given value, it means that the DSC peak or a melting point is within ±2° C. DSC and melting points provide an alternate means for one to distinguish between different AD crystal forms. Different crystal forms may be identified, at least in part, based on their different transition temperature profiles. IR measures absorption of infrared light caused by the presence of particular chemical bonds associated with groups in a molecule that vibrate in response to the light. DSC and/or IR can thus provide physicochemical information one can use to describe AD crystals.

Form 1

Single crystal X-ray crystallography was used to characterize Form 1 AD. Cell constants and an orientation matrix obtained from a least squares refinement using the measured positions of 3242 reflections with I>10σ in the range $3.00<2\theta<45.00°$ corresponded to a C-centered monoclinic cell specified as follows: a=12.85 Å, b=24.50 Å, c=8.28 Å, $\beta$=100.2°, Z=4, space group Cc.

The Form 1 XRD pattern usually shows a peak(s) at about 6.9, typically at about 6.9 and about 20.7, or more typically at about 6.9, about 15.7 and about 20.7 and ordinarily at least at about 6.9, about 11.8, about 15.7 and about 20.7. Typically the XRD peak at about 6.9, or usually either (1) this peak plus one or two peaks additional peaks or (2) the peak at about 6.9 plus one or two other peaks coupled with differential scanning calorimetry data or melting point data, is sufficient to distinguish Form 1 crystals from other forms or to identify Form 1 itself. The Form 1 spectrum commonly has peaks at about 6.9, about 11.8, about 12.7, about 15.7, about 17.2, about 20.7, about 21.5, about 22.5 and about 23.3. The Form 1 XRD pattern usually shows a peak(s) at any one (or combination) of about 6.9 and/or 11.8 and/or 15.7 and/or 17.2 and/or 20.7 and/or 23.3. FIG. 1 shows a typical Form 1 crystal X-ray diffraction pattern. It should be understood, however, that FIGS. 1–26 are only exemplary and that diagnostic representations of other crystalline AD preparations may depart from these depictions.

Form 1 AD is anhydrous, containing little or no detectable water. In general, Form 1 crystals ordinarily will contain less than about 1%, typically less than about 0.5%, and usually less than about 0.2% of water. Moreover, Form 1 crystals ordinarily will contain less than about 20%, typically will contain less than about 10%, often less than about 1%, and usually less than about 0.1% noncrystalline AD. Often, Form 1 crystals will contain no noncrystalline AD that is detectable by DSC, XRD or polarized light microscopy at 100× magnification. Form 1 AD is typically substantially free of crystallization solvent, i.e., typically less than about 1%, usually less than about 0.6%, if adequately recovered from the crystallization bath, and it does not contain lattice-entrained solvent molecules.

Form 1 crystals generally have a median size by light scattering of about 25–150 μm, usually about 30–80 μm. Individual Form 1 preparations usually contain crystals that have a length range of about 1–200 μm and have a typical maximum dimension for individual crystals in a preparation of about 60–200 μm. In some Form 1 preparations, about 1–10% of the crystals in a preparation will have a maximum dimension of greater than 250 μm. The Form 1 crystals shown in FIGS. 4–10 typically have tablet, plate, needle and/or irregular habits. Aggregates of Form 1 crystals also occur with a typical diameter range of about 25–150 μm.

Form 1 crystals exhibit a DSC endothermic transition at about 102° C. (see FIG. 2) and an IR spectrum essentially as depicted in FIG. 3. Different Form 1 crystal preparations have a bulk density of about 0.15–0.60 g/mL, usually about 0.25–0.50 g/mL, with a surface area of about 0.10–2.20 m²/g, usually about 0.20–0.60 m²/g. Form 1 AD is thus characterized by an XRD spectrum peak using Cu—Kα radiation, expressed in degrees 2θ at any one (or combination) of about 6.9 and/or 11.8 and/or 15.7 and/or 20.7 and an endothermic transition as measured by differential scanning calorimetry at about 102° C. Form 1 AD is alternatively characterized by an obvious XRD spectrum peak using Cu—Kα radiation, expressed in degrees 2θ at 6.9±0.1, 11.8±0.1, 15.7±0.1, 17.2±0.1, 20.7±0.1 and an endothermic transition peak as measured by differential scanning calorimetry at 102.0±2° and/or an endothermic onset at 99.8±2°.

Form 2

Figure 11:
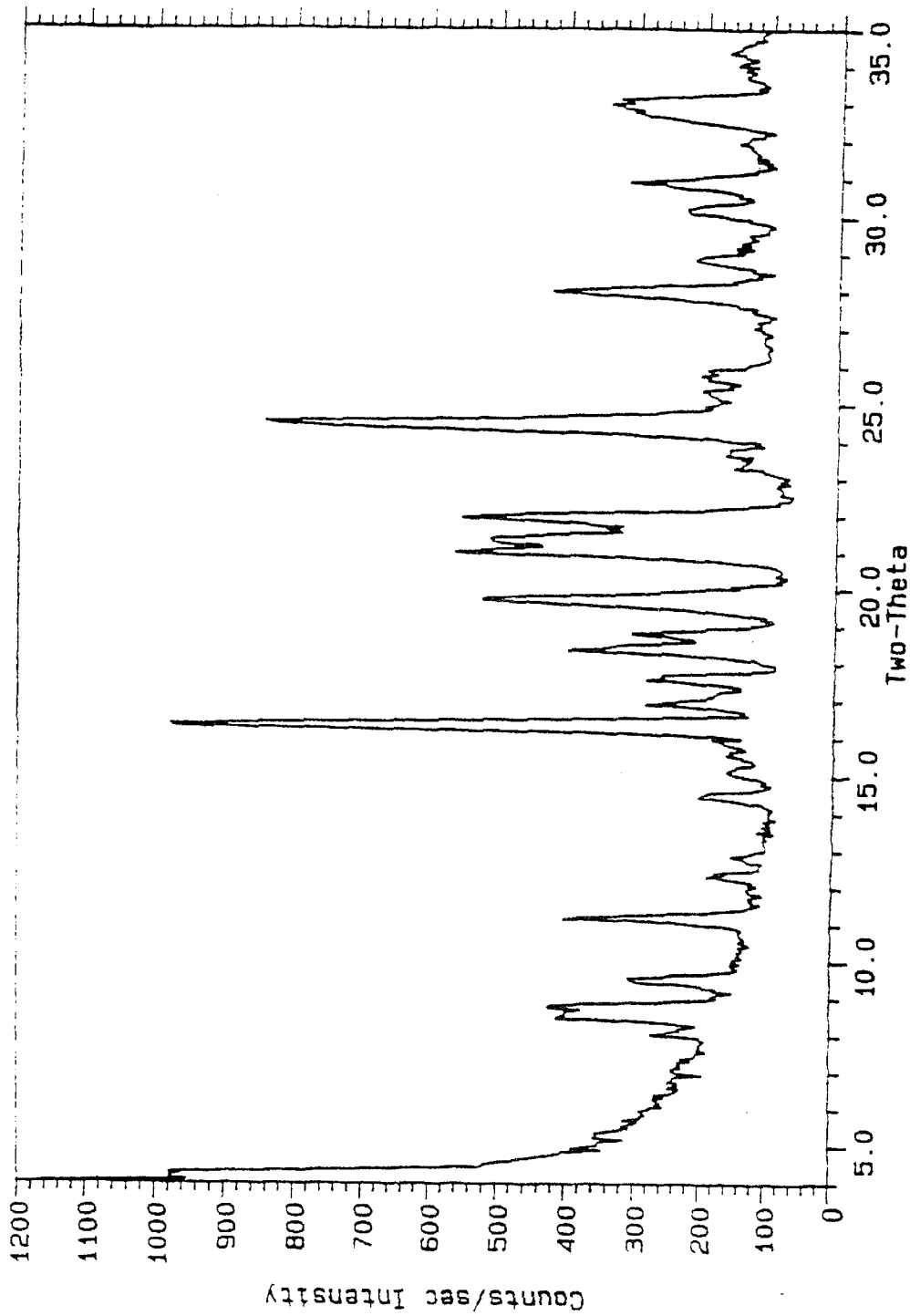
FIG. 11 shows an XRD pattern of Form 2 crystals.

The Form 2 XRD pattern, an example of which is depicted in FIG. 11, usually shows a peak(s) at about 22.0, typically at about 18.3 and about 22.0, or more typically at about 9.6, about 18.3 and about 22.0 and ordinarily at least at about 9.6, about 18.3, about 22.0 and about 32.8. Typically any three or four of these four characteristic XRD peaks, or usually either (1) four peaks or (2) two or three of these peaks coupled with differential scanning calorimetry data or melting point data, is sufficient to distinguish Form 2 crystals from other forms or to identify Form 2 itself. The Form 2 XRD pattern usually shows a peak(s) at any one (or combination) of about 8.7–8.9, about 9.6, about 16.3, about 18.3, about 18.9, about 19.7, about 21.0–21.3, about 21.4, about 22.0, about 24.3, about 27.9, about 30.8 and about 32.8.

Form 2 crystals are AD dihydrate, and they usually contain essentially no detectable crystallization solvent, other than water. Form 2 crystals ordinarily will contain less than about 30%, typically less than about 10%, often less than about 1%, usually less than about 0.1% of noncrystalline AD. Generally, the crystals will contain no noncrystalline AD that is detectable by DSC, XRD or polarized light microscopy at 100× magnification. Form 2 crystals typically have a median size of about 15–85 μm by light scattering, ordinarily about 25–80 μm. Individual Form 2 preparations usually contain crystals that have a length range of about 1–300 μm. Form 2 crystals have a DSC endothermic transition at about 73° C. (see FIG. 12) and an IR spectrum substantially as shown in FIG. 13. Form 2 AD is thus characterized by an XRD spectrum peak using Cu—Kα radiation, expressed in degrees 2θ at any one (or combination) of about 9.6 and/or 18.3 and/or 22.0 and/or 32.8 and an endothermic transition as measured by differential scanning calorimetry at about 73° C. Form 2 AD is alternatively characterized by an obvious XRD spectrum peak using Cu—Kα radiation, expressed in degrees 2θ at 9.6±0.1, 18.3±0.1, 22.0±0.1, 24.3±0.1 and 32.8±0.1 and an endothermic transition peak as measured by differential scanning calorimetry at 72.7±2° and/or an endothermic onset at 69.5±2°.

Form 3

Figure 14:
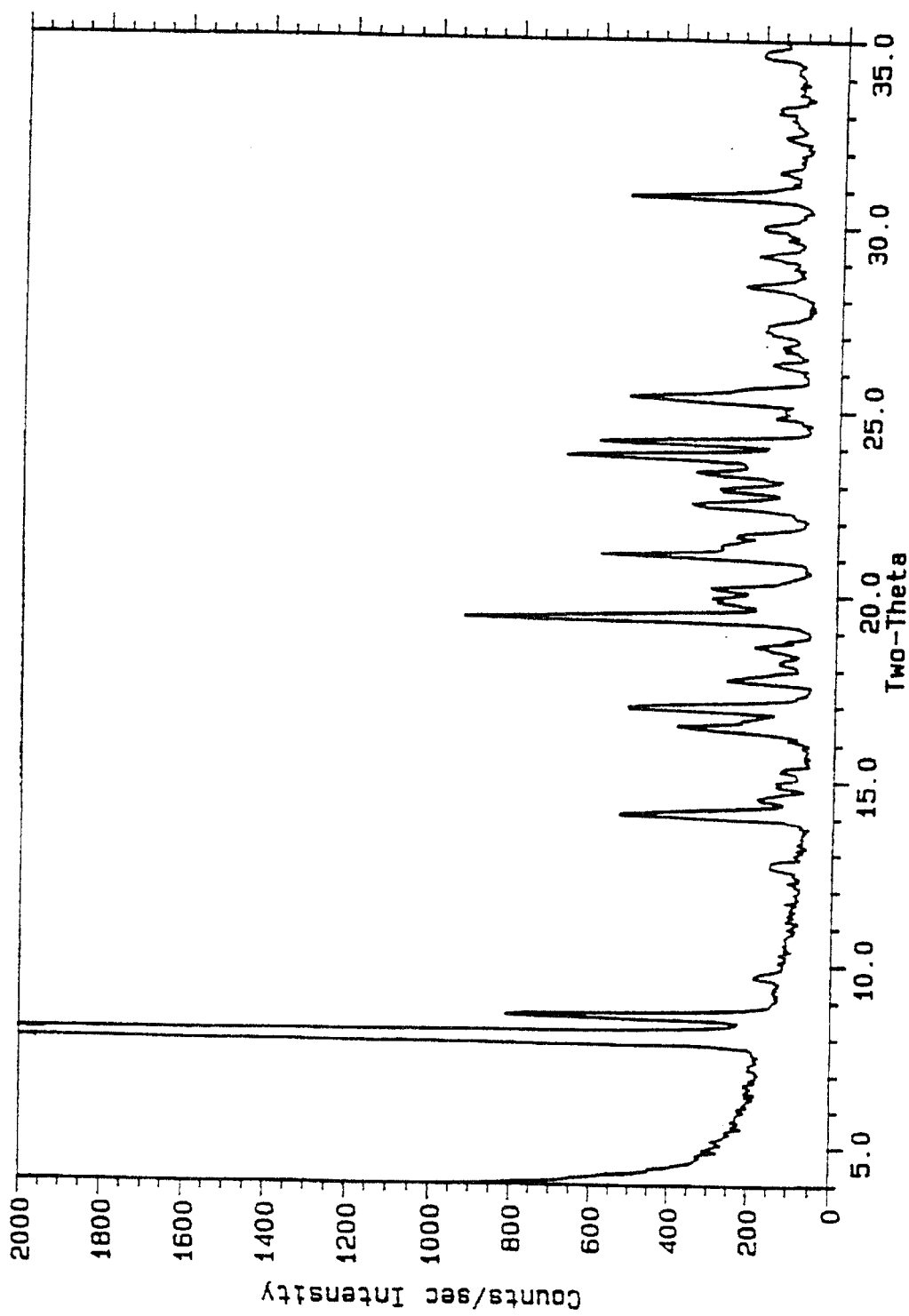
FIG. 14 shows an XRD pattern of Form 3 crystals.
Figure 15:
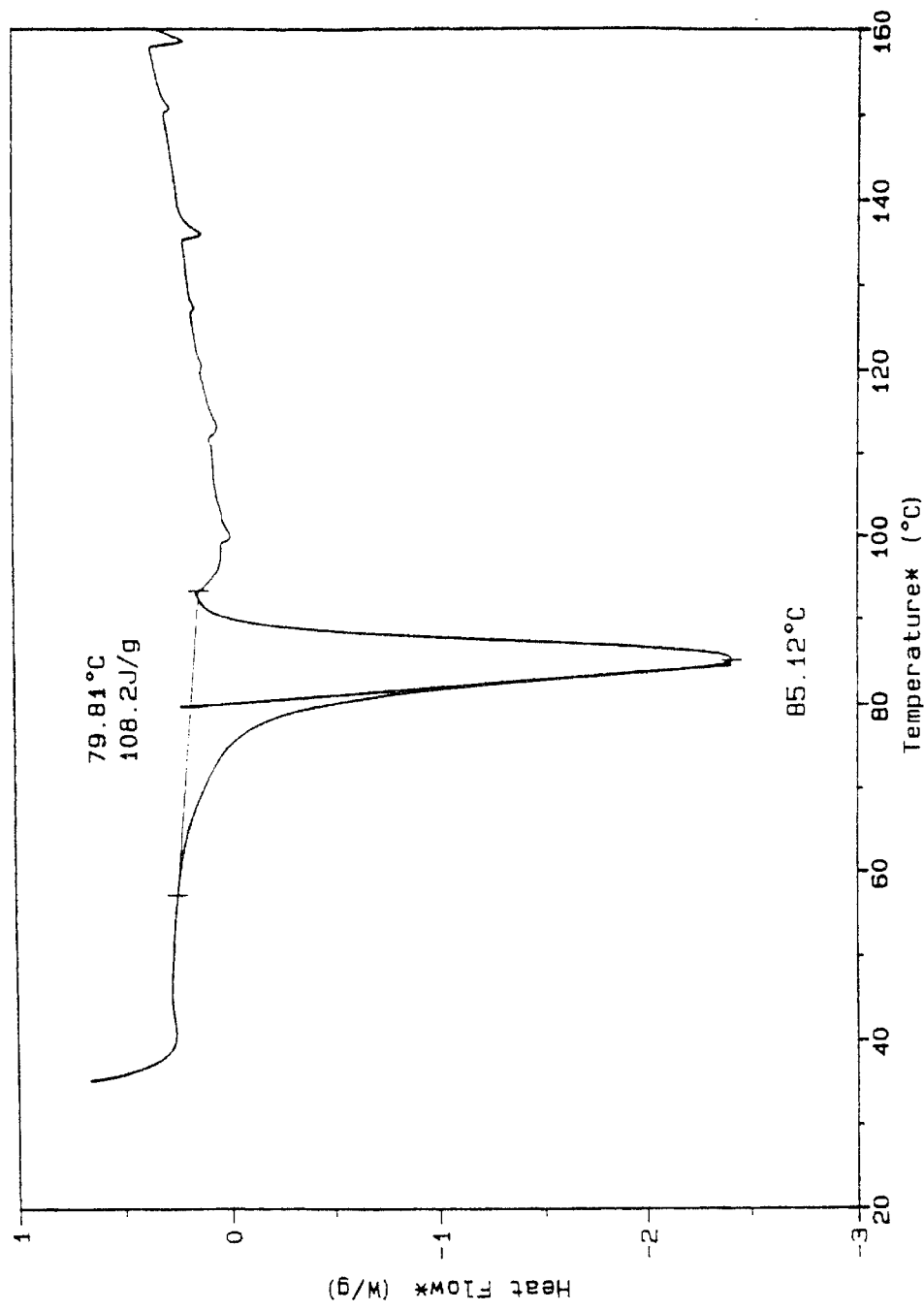
FIG. 15 shows a thermogram obtained by differential scanning calorimetry of Form 3 crystals.

A Form 3 XRD pattern such as that shown in FIG. 14 usually shows a peak(s) at about 8.1, typically at about 8.1 and about 25.4, or more typically at about 8.1, about 19.4 and about 25.4. Typically any one or two of these three characteristic XRD peaks, or usually either (1) three or four of these peaks or (2) two or three of these peaks coupled with differential scanning calorimetry data or melting point data, is sufficient to distinguish Form 3 crystals from other forms or to identify Form 3 itself. Form 3 AD has an endothermic transition at about 85° as measured by differential scanning calorimetry (FIG. 15). The Form 3 spectrum commonly has peaks at any one (or combination) of about 8.1, about 8.7, about 14.1, about 16.5, about 17.0, about 19.4, about 21.1, about 22.6, about 23.4, about 24.2, about 25.4 and about 30.9.

Unlike Forms 1 and 2, Form 3 crystals contain about one equivalent of methanol in the crystal lattice. The methanol typically is donated by crystallization solvent. However, Form 3 contains essentially no other detectable solvent or water. Form 3 crystals ordinarily will contain less than about 20%, typically less than about 10%, often less than about 1%, usually less than about 0.1% of noncrystalline AD. The crystals will contain no noncrystalline AD that is detectable by DSC, XRD or polarized light microscopy at 100× magnification. Form 3 crystals typically have a median size of about 20–150 μm by light scattering, ordinarily about 30–120 μm. Individual Form 3 preparations usually contain crystals that have a length range of about 1–300 μm.

Form 4

Figure 16:
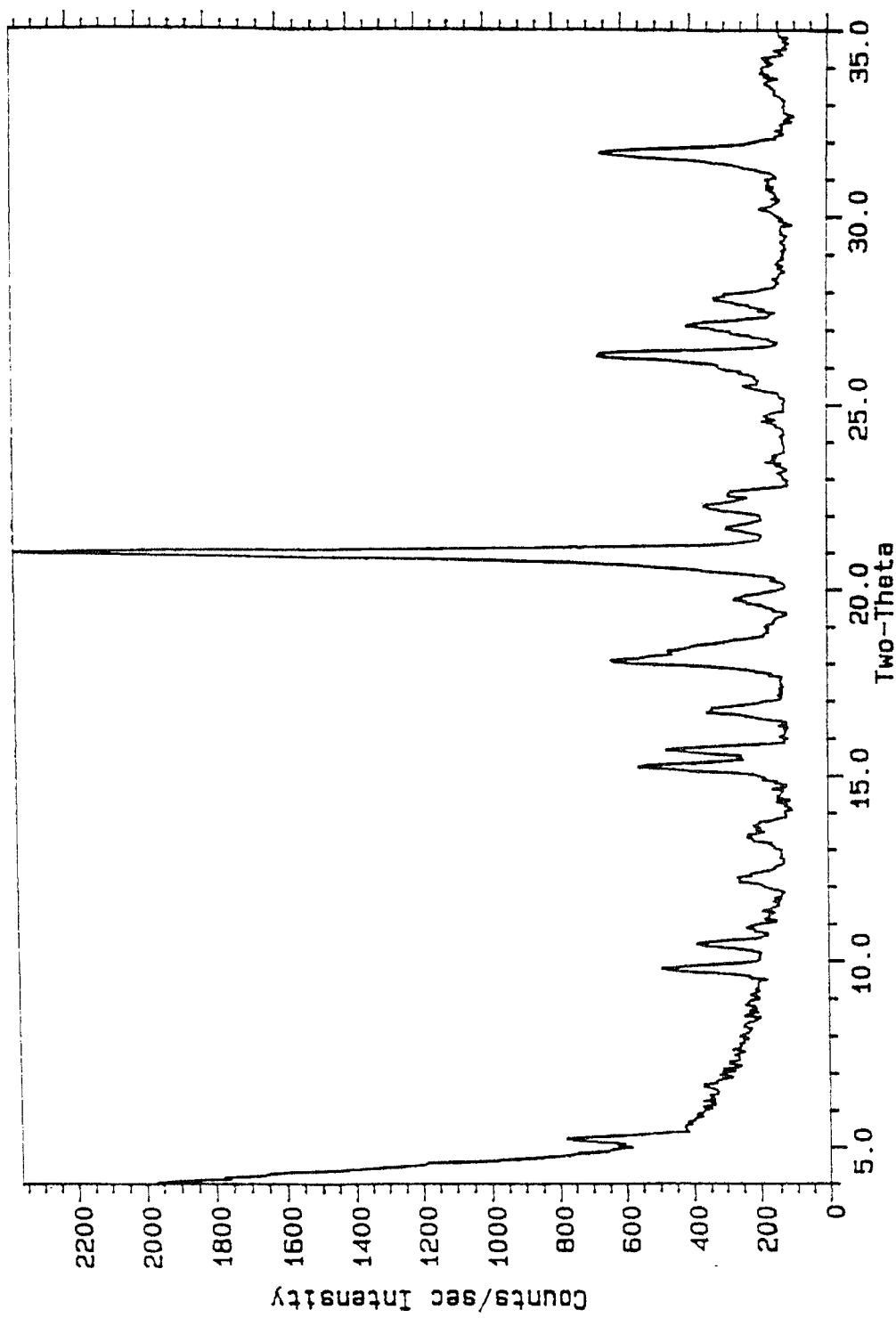
FIG. 16 shows a Form 4 crystal XRD pattern.
Figure 17:
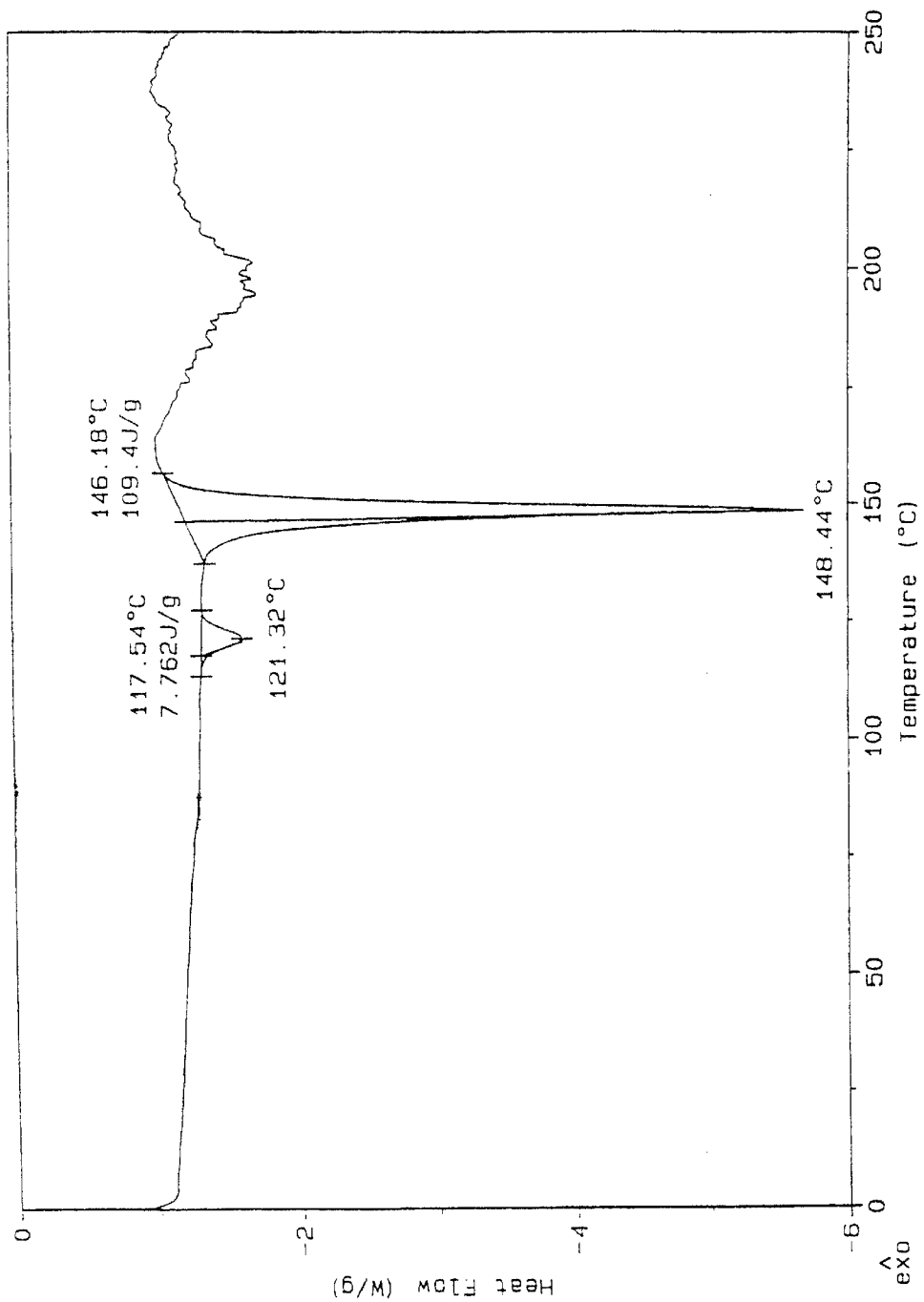
FIG. 17 shows a thermogram obtained by differential scanning calorimetry of Form 4 crystals.

A Form 4 XRD pattern such as that shown in FIG. 16 usually shows a peak(s) at about 26.3, typically at about 26.3 and about 31.7, or typically at about 26.3, about 31.7 and about 15.2, or usually at about 26.3, about 31.7, about 15.2 and about 21.0. Typically these four characteristic XRD peaks, or usually either (1) three of these peaks or (2) two or three of these peaks coupled with differential scanning calorimetry data or melting point data, is sufficient to distinguish Form 4 crystals from other forms or to identify Form 4 itself. Form 4 AD has endothermic transitions at about 121° and about 148° as measured by differential scanning calorimetry (FIG. 17). The Form 4 spectrum commonly has peaks at any one (or combination) of about 9.8, about 15.2, about 15.7, about 18.1, about 18.3, about 21.0, about 26.3, and about 31.7.

The invention includes compositions comprising mixtures of two or more different crystal types or forms, e.g., Form 1 and Form 2 crystals, Form 1, Form 2 and Form 4 crystals, or Form 2 and Form 4 crystals. Mixtures of Form 1 and Form 2 AD crystals may be present in pharmaceutical formulations or their manufacture, and typically such mixtures comprise at least about 70% Form 1, usually at least about 90%, but in some instances up to about 70% of such a mixture may comprise Form 2.

Crystalline Salts of Organic and Inorganic Acids

Figure 24:
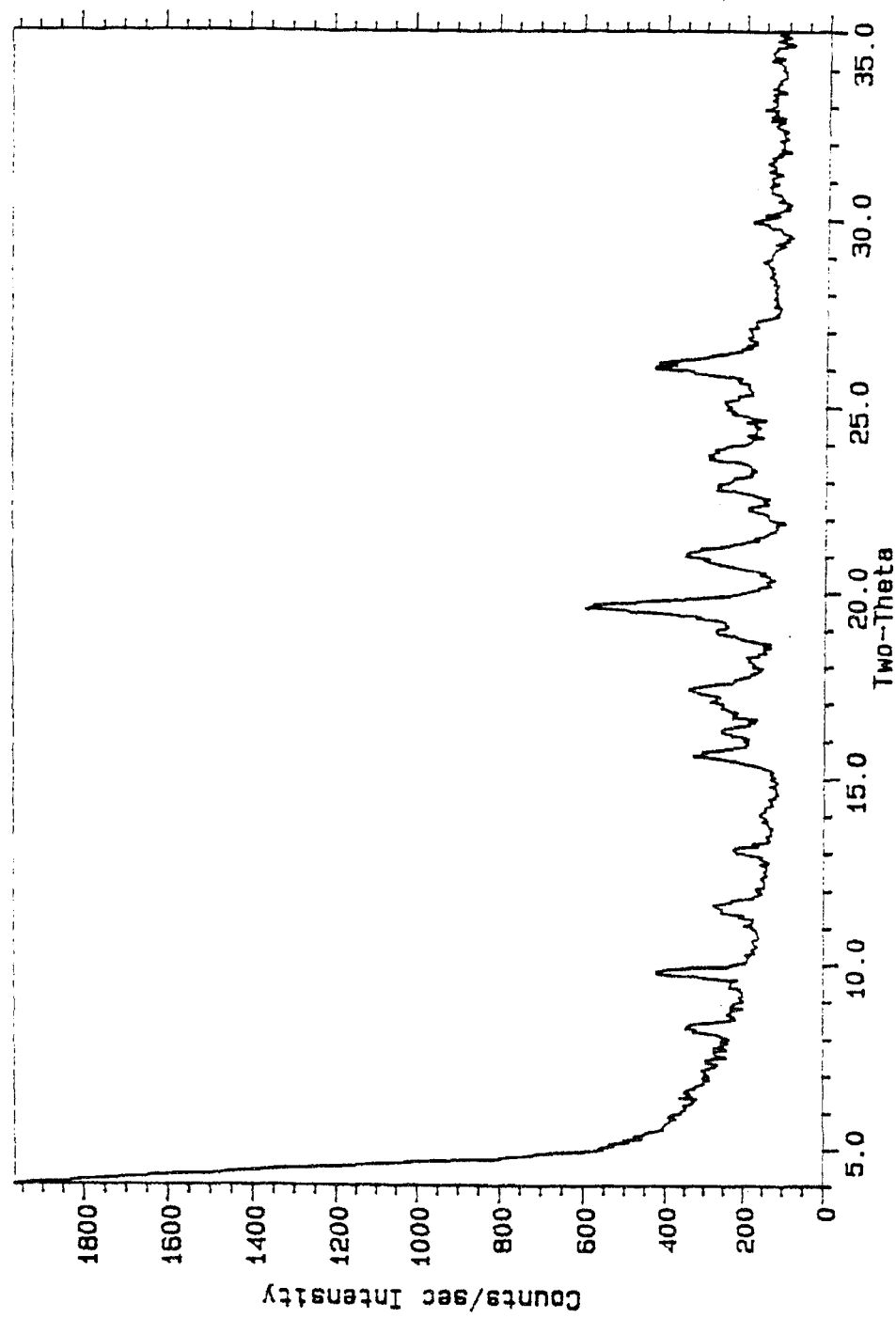
FIG. 24 shows an AD α-naphthylene sulfonate salt crystal XRD pattern.
Figure 25:
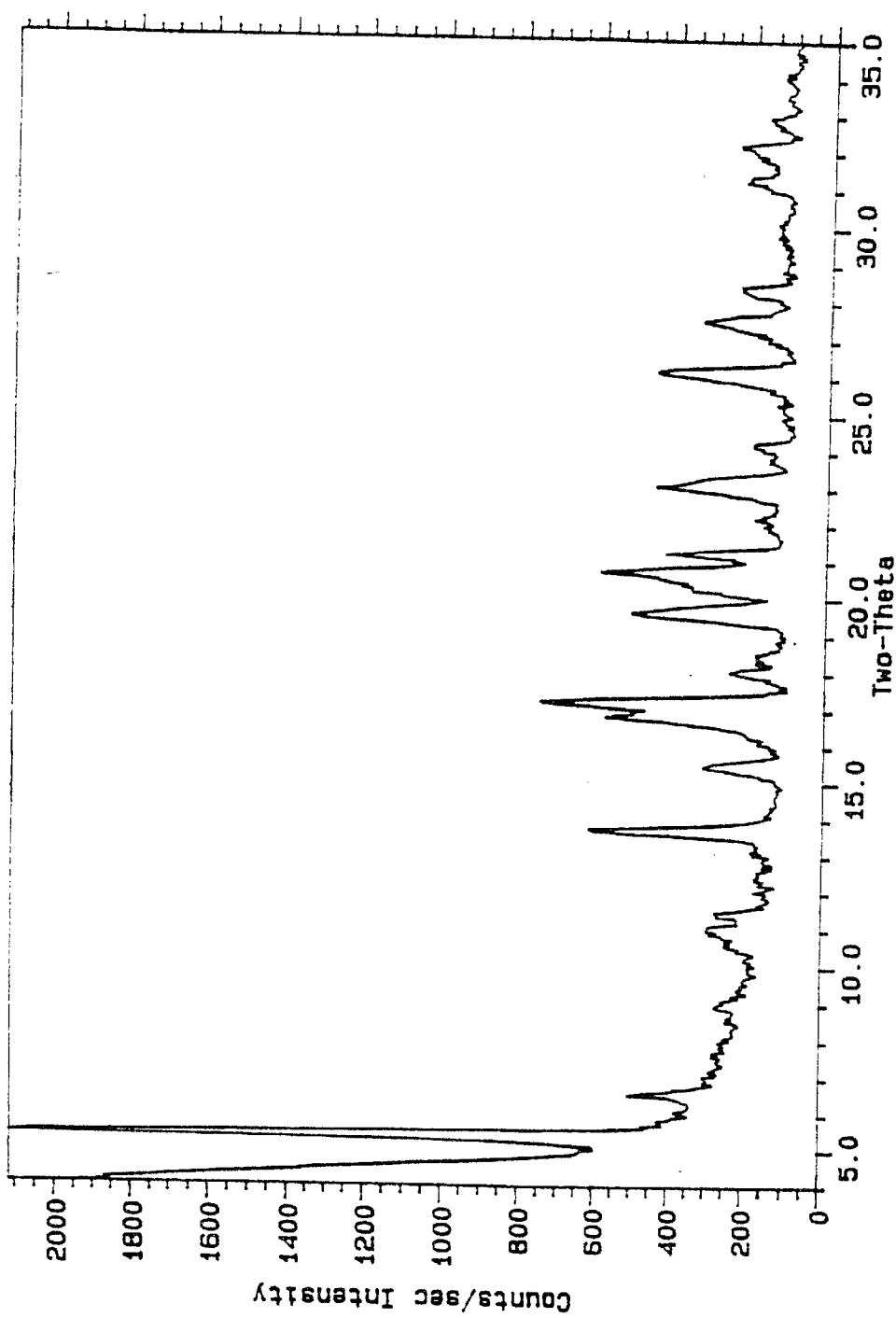
FIG. 25 shows an AD (S)-camphor sulfonate salt crystal XRD pattern.
Figure 26:
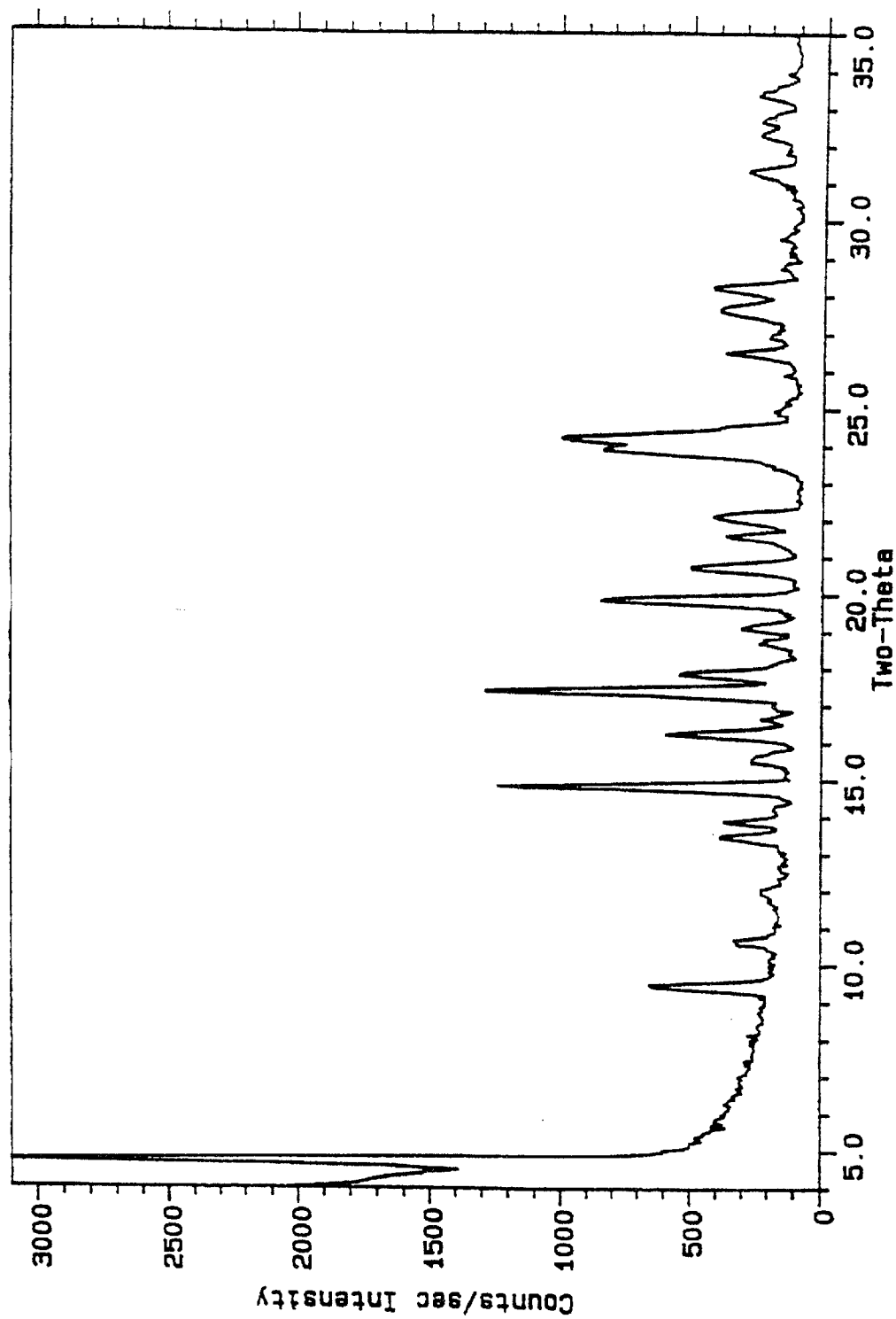
FIG. 26 shows an AD succillic acid salt crystal XRD pattern.

FIGS. 18–26 show XRD spectra obtained from crystalline salts or, alternatively, complexes of AD and organic and inorganic acids. These salts are a hemisulfate salt or complex (FIG. 18), a hydrobromide salt or complex (FIG. 19), a nitrate salt or complex (FIG. 20), a mesylate ($CH_3SO_3H$) salt or complex (FIG. 21), an ethyl sulfonate salt ($C_2H_5SO_3H$) or complex (FIG. 22), a β-naphthylene sulfonic acid salt or complex (FIG. 23), an α-naphthylene sulfonic acid salt or complex (FIG. 24), an (S)-camphor sulfonic acid salt or complex (FIG. 25) and a succinic acid salt or complex (FIG. 26). These XRD spectra show a number of peaks that characterize the compounds and allow one to identify each compound from other crystalline forms.

Figure 18:
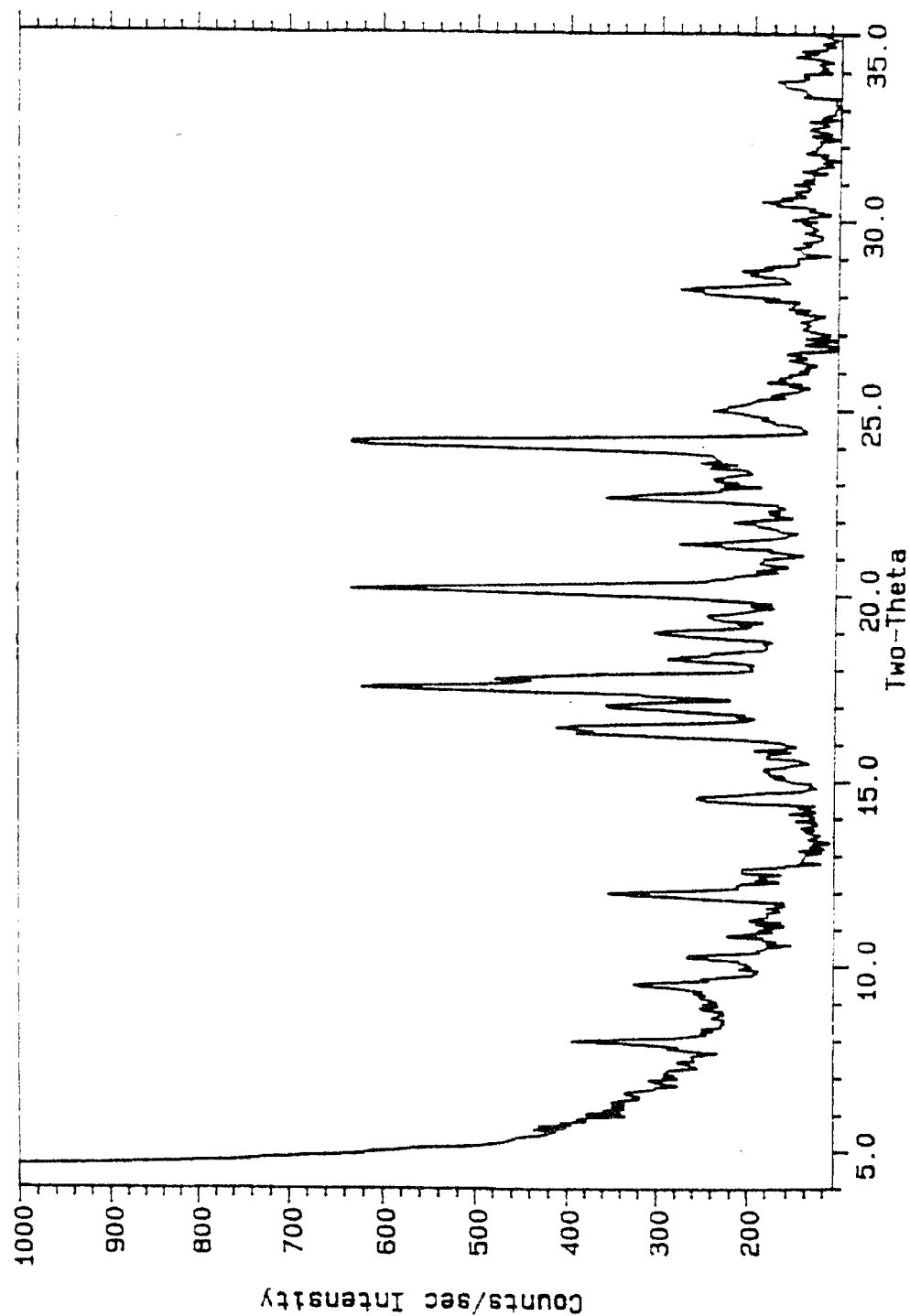
FIG. 18 shows an AD hemisulfate salt crystal XRD pattern.

FIG. 18 shows that the hemisulfate salt or complex has distinctive XRD peaks in degrees 2θ at any one (or combination) of about 8.0, about 9.5, about 12.0, about 14.6, about 16.4, about 17.0, about 17.5–17.7, about 18.3, about 19.0, about 20.2, about 22.7, about 24.1 and about 28.2. The salt or complex has a melting point of about 131–134° C. It is thus characterized as having four of these distinctive XRD peaks at about 12.0, about 14.6, about 16.4 and about 17.5–17.7. One may further characterize the compound as having three or four of these XRD peaks and having a melting point of about 131–134° C. The hemisulfate of AD is alternatively characterized by an obvious XRD spectrum peak using Cu—Kα radiation, expressed in degrees 2θ at 8.0±0.1, 12.0±0.1, 14.6±0.1, 16.4±0.1 and 17.5–17.7±0.3 and a melting point of 131–134±2.0°.

Figure 19:
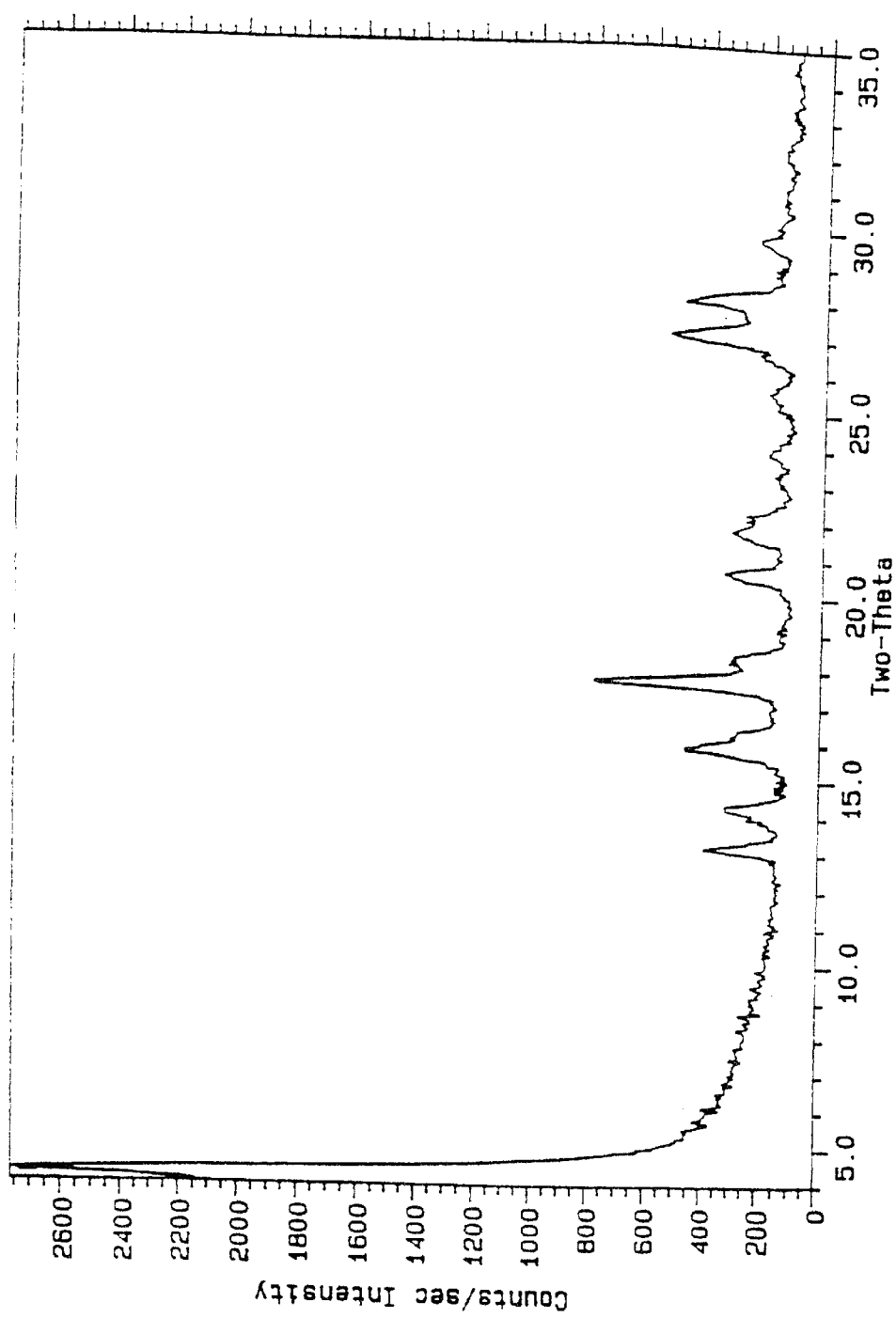
FIG. 19 shows an AD hydrobromide salt crystal XRD pattern.

FIG. 19 shows that the hydrobromide salt or complex has distinctive XRD peaks in degrees 2θ at any one (or combination) of about 13.2, about 14.3, about 15.9, about 17.8, about 20.7, about 21.8, about 27.2 and about 28.1. The salt or complex decomposes on heating at about 196–199° C. It is thus characterized as having four distinctive XRD peaks at about 13.2, about 14.3, about 17.8 and about 28.1. One may further characterize the compound as having three or four of these XRD peaks and decomposing on heating to about 196–199° C. The hydrobromide of AD is alternatively characterized by an obvious XRD spectrum peak using Cu—Kα radiation, expressed in degrees 2θ at 13.2±0.1, 14.3±0.1, 17.8±0.1, 20.7±0.1 and 27.2±0.1 and a decomposition point of 196–199±2.0°.

Figure 20:
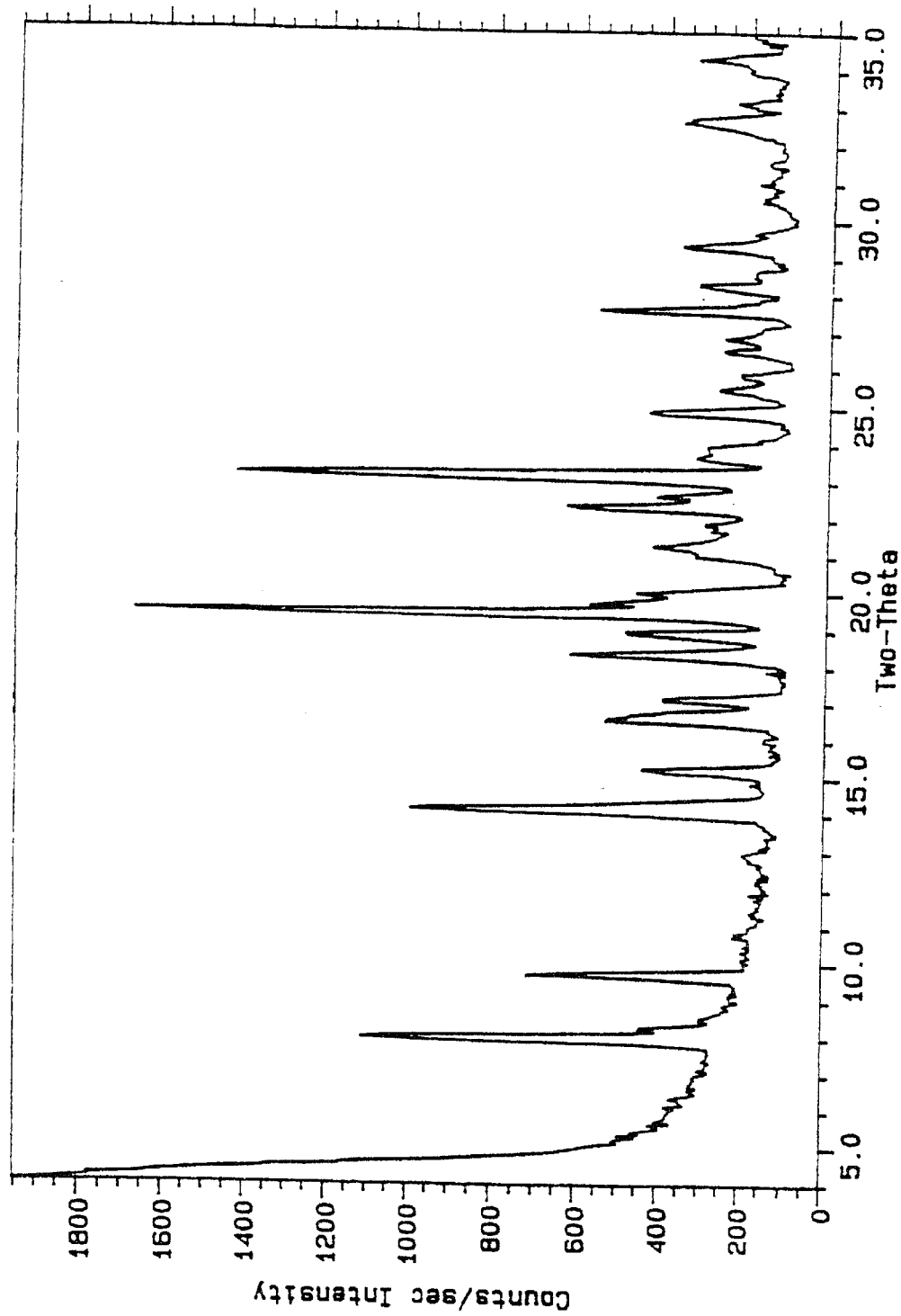
FIG. 20 shows an AD nitrate salt crystal XRD pattern.

FIG. 20 shows that the nitrate salt or complex has distinctive XRD peaks in degrees 2θ at any one (or combination) of about 8.0, about 9.7, about 14.1, about 15.2, about 16.7, about 17.1, about 18.3, about 18.9, about 19.4, about 20.0, about 21.2, about 22.3, about 23.2, about 24.9, about 27.6, about 28.2, about 29.4 and about 32.6. The salt or complex decomposes on heating at about 135–136° C. It is thus characterized as having four distinctive XRD peaks at about 14.1, about 23.2, about 29.4 and about 32.6. One may further characterize the compound as having three or four of these XRD peaks and having a melting point of about 131–134° C. The nitrate of AD is alternatively characterized by an obvious XRD spectrum peak using Cu—Kα radiation, expressed in degrees 2θ at 8.0±0.1, 14.1±0.1, 23.2±0.1, 29.4±0.1 and 32.6±0.1 and a decomposition point of 135–136±2.0°.

Figure 21:
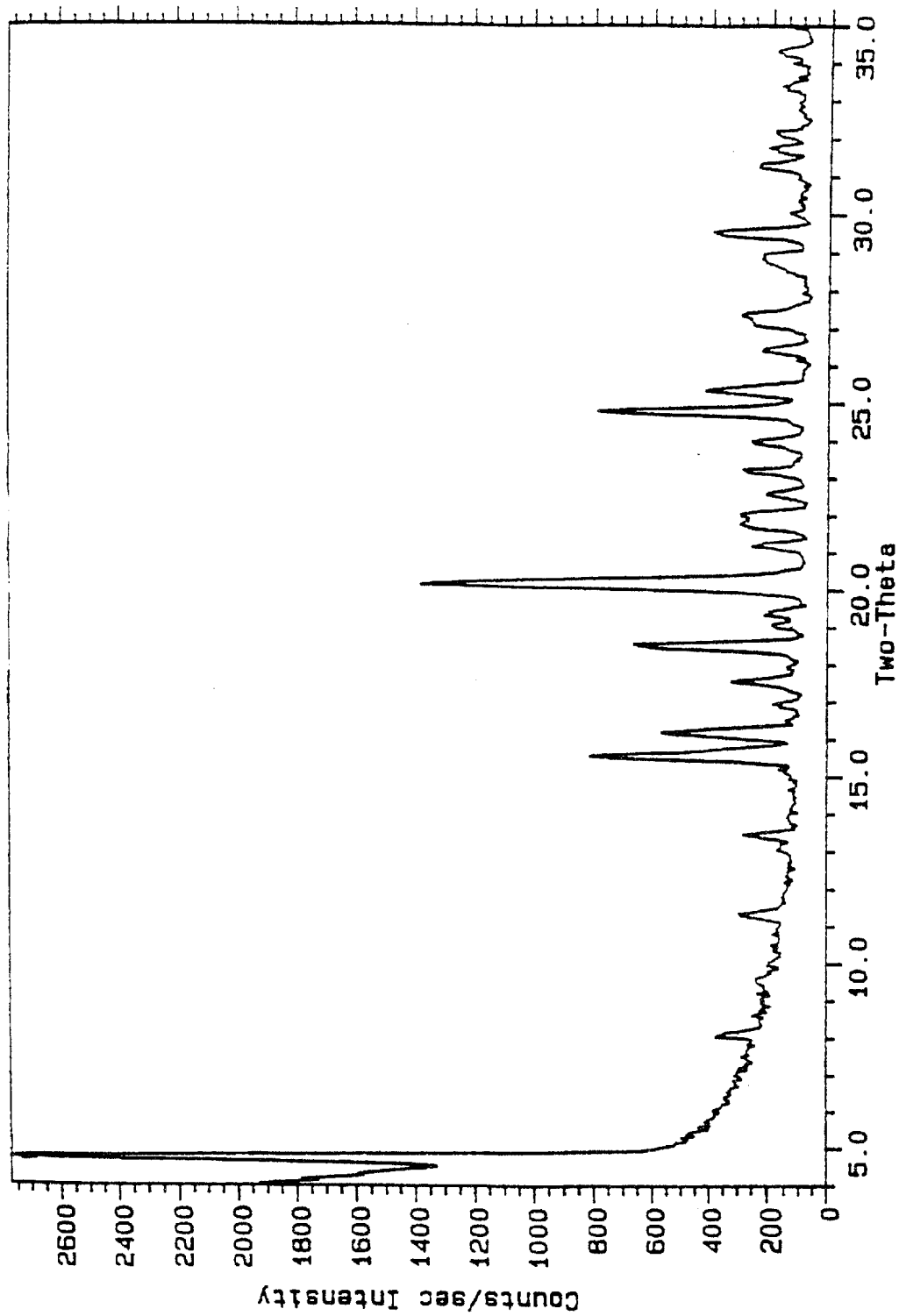
FIG. 21 shows an AD mesylate salt crystal XRD pattern.

FIG. 21 shows that the mesylate salt or complex has distinctive XRD peaks in degrees 2θ at any one (or combination) of about 4.8, about 15.5, about 16.2, about 17.5, about 18.5, about 20.2, about 24.8, about 25.4 and about 29.5. The salt or complex has a melting point of about 138–139° C. It is thus characterized as having four distinctive XRD peaks at about 4.8, about 15.5, about 20.2 and about 24.8. One may further characterize the compound as having three or four of these XRD peaks and having a melting point of about 138–139° C. The mesylate of AD is alternatively characterized by an obvious XRD spectrum peak using Cu—Kα radiation, expressed in degrees 2θ at 4.8±0.1, 15.5±0.1, 16.2±0.1, 20.2±0.1 and 24.8±0.1 and a melting point of 138–139±2.0°.

Figure 22:
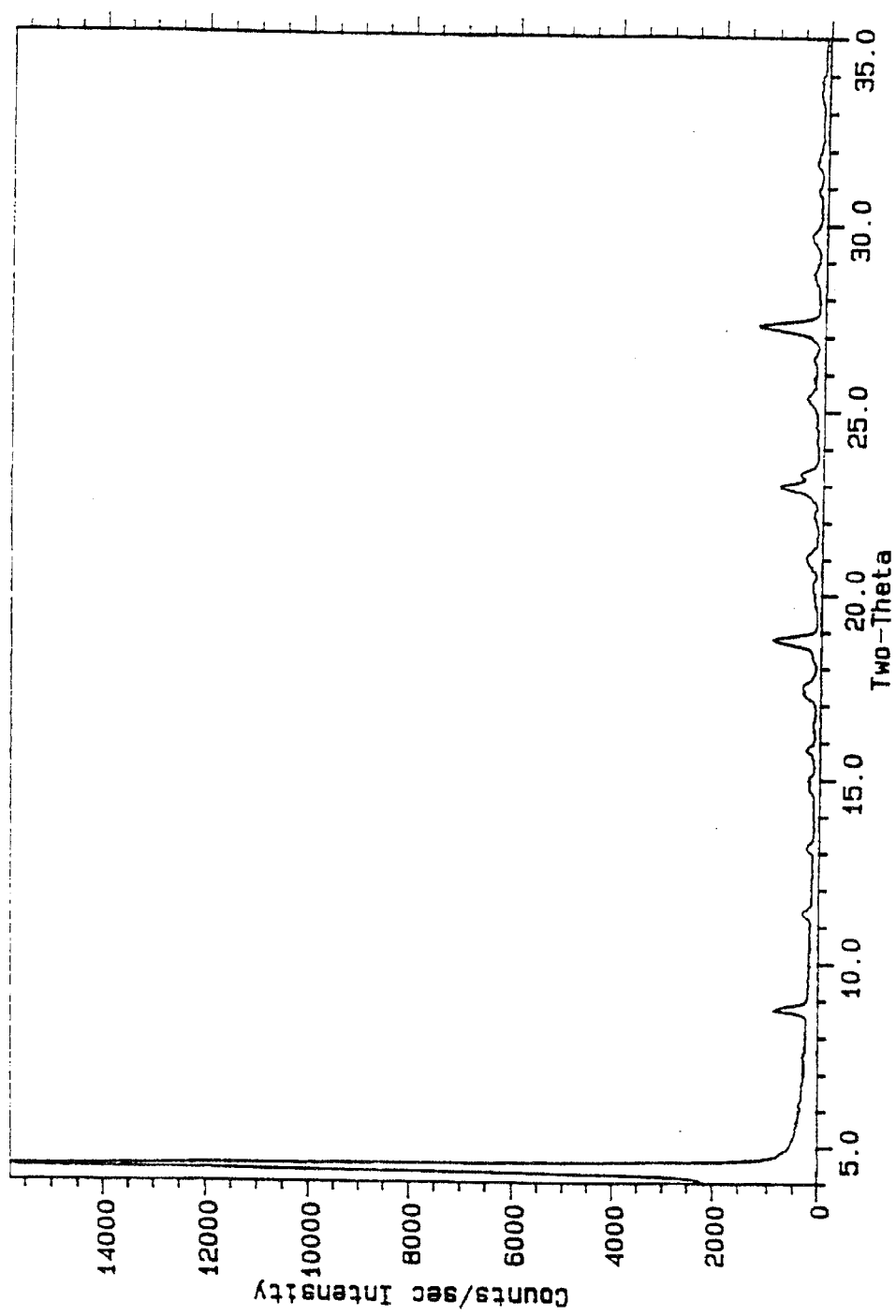
FIG. 22 shows an AD ethyl sulfonate salt crystal XRD pattern.

FIG. 22 shows that the ethyl sulfonate salt or complex has distinctive XRD peaks in degrees 2θ at any one (or combination) of about 4.4, about 8.8, about 18.8, about 23.0–23.3 and about 27.3. The salt or complex has a melting point of about 132–133° C. It is thus characterized as having four distinctive XRD peaks at about 4.4, about 8.8, about 18.8 and about 27.3. One may further characterize the compound as having three or four of these XRD peaks and having a melting point of about 132–133° C. The ethyl sulfonate of AD is alternatively characterized by an obvious XRD spectrum peak using Cu—Kα radiation, expressed in degrees 2θ at 4.4±0.1, 8.8±0.1, 18.8±0.1, 23.0–23.3±0.3 and 27.3±0.1 and a melting point of 132–133±2.0°.

Figure 23:
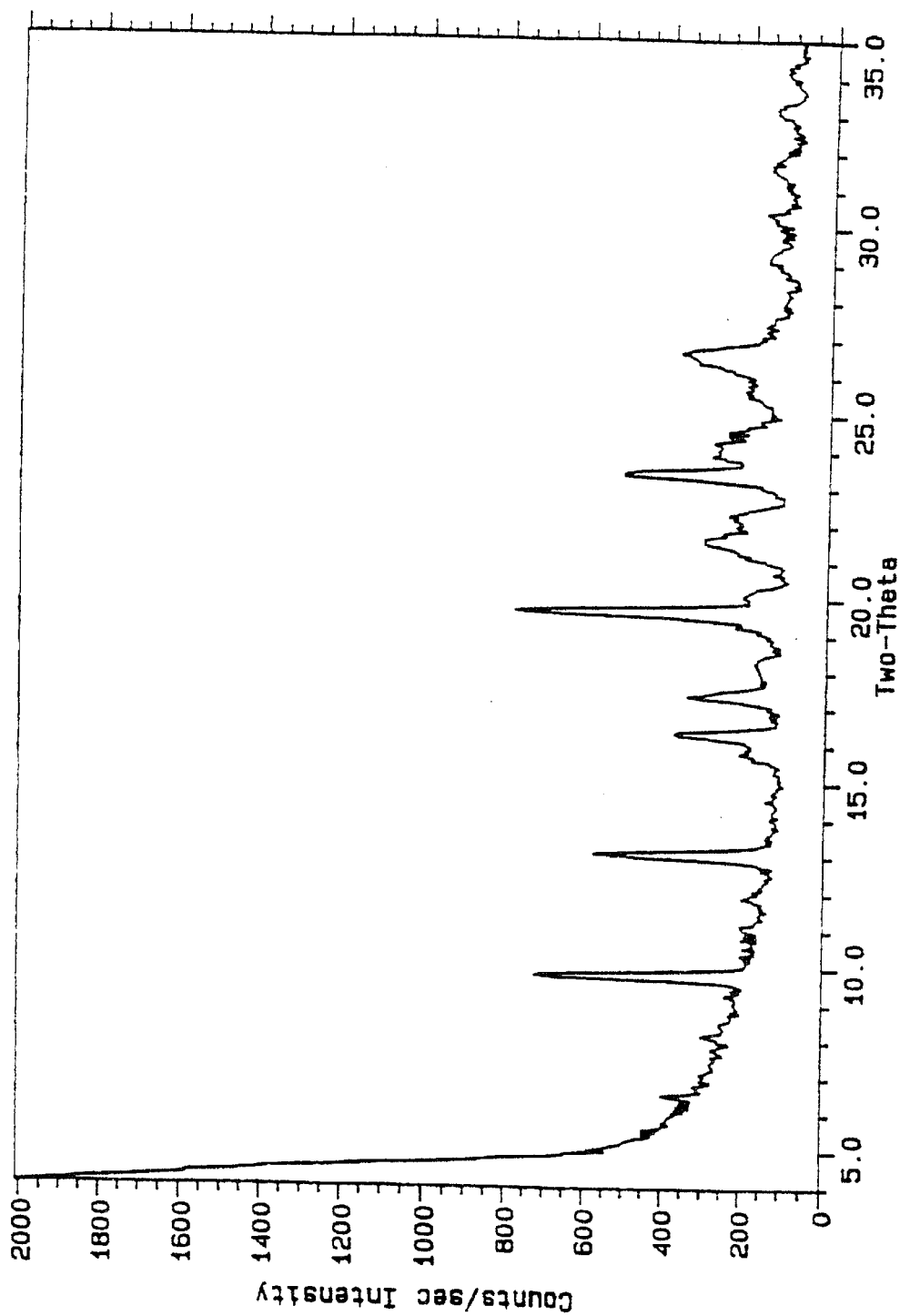
FIG. 23 shows an AD β-naphthylene sulfonate salt crystal XRD pattern.

FIG. 23 shows that the β-naphthylene sulfonic acid salt or complex has distinctive XRD peaks in degrees 2θ at any one (or combination) of about 9.8, about 13.1, about 16.3, about 17.4, about 19.6, about 21.6–22.3, about 23.4, about 24.1–24.5 and about 26.6. The salt or complex has a melting point of about 156–157° C. It is thus characterized as having four distinctive XRD peaks at about 13.1, about 17.4, about 23.4 and about 26.2. One may further characterize the compound as having three or four of these XRD peaks and having a melting point of about 156–157° C. The β-naphthylene sulfonate of AD is alternatively characterized by an obvious XRD spectrum peak using Cu—Kα radiation, expressed in degrees 2θ at 9.8±0.1, 13.1±0.1, 17.4±0.1, 23.4±0.1 and 26.2±0.1 and a melting point of 156–157±2.0°.

FIG. 24 shows that the α-naphthylene sulfonic acid salt or complex has distinctive XRD peaks in degrees 2θ at any one (or combination) of about 8.3, about 9.8, about 11.5, about 15.6, about 16.3, about 16.7–17.4, about 19.6, about 21.0, about 22.9, about 23.7, about 25.0 and about 26.1. The salt or complex has a melting point of about 122–128° C. It is thus characterized as having four distinctive XRD peaks at about 9.8, about 15.6, about 19.6 and about 26.1. One may further characterize the compound as having three or four of these XRD peaks and having a melting point of about 122–128° C. The α-naphthylene sulfonate of AD is alternatively characterized by an obvious XRD spectrum peak using Cu—Kα radiation, expressed in degrees 2θ at 9.8±0.1, 15.6±0.1, 19.6±0.1, 21.0±0.1 and 26.1±0.1 and a melting point of 122–128±2.0°.

FIG. 25 shows that the (S)-camphor sulfonic acid salt or complex has distinctive XRD peaks in degrees 2θ at any one (or combination) of about 5.4, about 6.5, about 13.7, about 15.5, about 16.8–17.2, about 19.6, about 20.4–20.7, about 21.2, about 23.1, about 26.1, about 27.5, about 28.4, about 31.3 and about 32.2. The salt or complex has a melting point of about 160–161° C. It is thus characterized as having four distinctive XRD peaks at about 5.4, about 6.5, about 13.7 and about 16.8–17.2. One may further characterize the compound as having three or four of these XRD peaks and having a melting point of about 160–161° C. The (S)-camphor sulfonate of AD is alternatively characterized by an obvious XRD spectrum peak using Cu—Kα radiation, expressed in degrees 2θ at 5.4±0.1, 6.5±0.1, 13.7±0.1, 16.8–17.2±0.3 and 19.6±0.1 and a melting point of 160–161±2°.

FIG. 26 shows that the succinic acid salt or complex has distinctive XRD peaks in degrees 2θ at any one (or combination) of about 4.7, about 9.5, about 10.6, about 14.9, about 16.3, about 17.4, about 17.9, about 19.9, about 20.8, about 22.1, about 23.9–24.2, about 26.5, about 27.6 and about 28.2. The salt or complex has a melting point of about 122–124° C. It is thus characterized as having four distinctive XRD peaks at about 4.7, about 9.5 about 14.9 and about 17.4. One may further characterize the compound as having three or four of these XRD peaks and having a melting point of about 122–124° C. The succinate of AD is alternatively characterized by an obvious XRD spectrum peak using Cu—Kα radiation, expressed in degrees 2θ at 9.5±0.1, 14.9±0.1, 16.3±0.1, 17.4±0.1 and 23.9–24.2±0.6 and a melting point of 122–124±2.0°.

Invention embodiments include compositions comprising a crystalline salt, e.g., a salt as characterized above, of adefovir dipivoxil and a pharmaceutically acceptable excipient(s). Other embodiments include a process to prepare a pharmaceutically acceptable composition by contacting a crystalline salt, e.g., a salt as characterized above, of adefovir dipivoxil and a pharmaceutically acceptable excipient(s). Other embodiments include the product produced by the process of contacting a crystalline salt, e.g., a salt as characterized above, of adefovir dipivoxil and a pharmaceutically acceptable excipient(s).

Methods for AD Synthesis

Diagram A below shows a representative process flow diagram for making AD and Form 1 AD crystals.

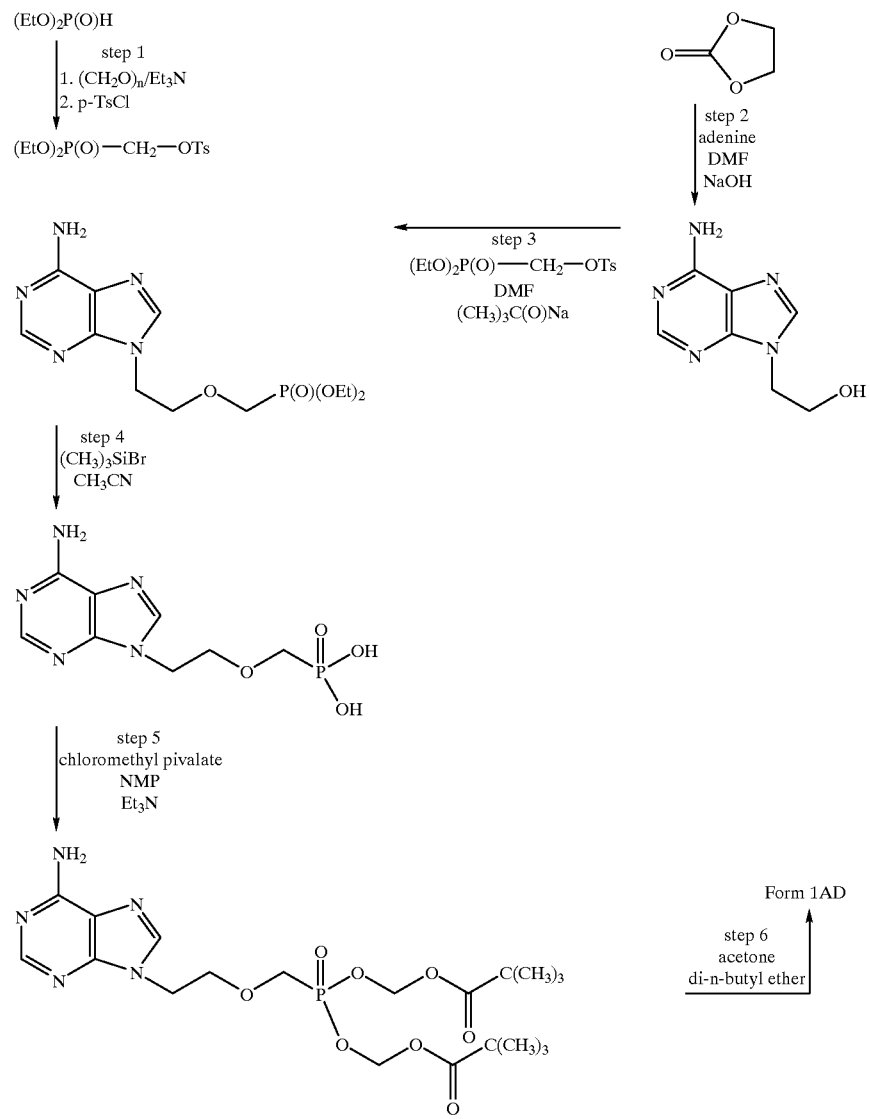

Diagram A

One can increase or decrease the scale of the process steps shown in Diagram A and described below if desired.

Methods for Diethyl p-toluenesulfonyloxymethylphosphonate Synthesis

In an embodiment, synthesis of diethyl p-toluenesulfonyloxymethylphosphonate, shown in Diagram A, Step 1, is described as follows. In a reactor having an inert atmosphere, e.g., nitrogen, a mixture of diethylphosphite (0.8 kg), paraformaldehyde (0.22 kg), and triethylamine (0.06 kg) in toluene (2.69 kg) is heated to 87° C. (84 to 110° C.) for 2 hours with agitation, then heated to reflux and maintained for at reflux for 1 hour, until the reaction is complete. Reaction completion is monitored by TLC (trace or no diethyl phosphite detectable) and confirmed by $^1$H NMR showing no more than 1% of the diethyl phosphite peak at δ 8.4–8.6 ppm. The solution is cooled to about 1° C. (−2 to 4° C.) and p-toluenesulfonyl chloride (1.0 kg) is added and then triethylamine (0.82 kg) at no more than 10° C. is slowly added (over about 3–6 hours in an exothermic reaction). The resulting mixture is warmed to 22° C. (19–25° C.) and stirred for at least 5 hours (typically about 16–24 hours), until the reaction is complete. Reaction completion is monitored by TLC (trace or no p-toluenesulfonyl chloride detectable) and confirmed by $^1$H NMR (p-toluenesulfonyl chloride doublet at δ 7.9 ppm no longer detected). The solids are removed by filtration and rinsed with toluene (0.34 kg). The combined washings and filtrate are washed either twice with water (1.15 kg each), or optionally with a sequence of water (1.15 kg), 5% aqueous sodium carbonate (3.38 kg), and twice with water (1.15 kg each). In the event emulsion occurs, brine may be added to the first organic/water mixture. The organic phase, which is at no more than 50° C., is distilled in vacuo (to LOD no more than 10% and water content, by KF (Karl Fischer) titration, no more than 0.5%), affording the title compound as an oil of about 85–95% purity, exclusive of toluene. The oil may become viscous on cooling.

Methods for 9-(2-Hydroxyethyl)adenine Synthesis

In an embodiment, synthesis of 9-(2-hydroxyethyl) adenine, shown in Diagram A, Step 2, is described as follows. In a reactor having an inert atmosphere, e.g., nitrogen, sodium hydroxide (6 g) is added to a slurry of adenine (1.0 kg) and molten ethylene carbonate (0.72 kg, m.p. 37–39° C.), in DMF (2.5 kg) and the mixture is heated to 125° C. (95° C. to reflux) with agitation until the reaction is complete (about 3–9 hours if the mixture temperature is at 110° C. to reflux or about 15–48 hours if at 95 to 110° C.). Reaction completion is monitored by HPLC (no more than 0.5% adenine remaining). The mixture is cooled to below 50° C. and diluted with toluene (3.2 kg). The resulting slurry is cooled to 3° C. (0–6° C.) and agitated for at least 2 hours. The slurry is filtered and the filter cake is washed twice with cold (0–5° C.) toluene (0.6 kg each). The filter cake is dried in vacuo at 35 to 70° C. (no more than 2% toluene, by $^1$H NMR or LOD) and optionally milled, affording the title compound as a white to off-white powdery solid.

Methods for 9-[2-(Diethylphosphonomethoxy)ethyl]adenine Synthesis

This compound is prepared using a composition comprising sodium alkoxide ($C_{1-6}$ alkyl) and 9-(2-hydroxyethyl)adenine. One contacts sodium alkoxide, typically sodium t-butoxide or sodium i-propoxide, with 9-(2-hydroxyethyl)adenine in a solvent such as DMF, at a temperature of about 20–30° over about 1–4 hours. The synthesis typically gives good results with 1 molar equivalent of 9-(2-hydroxyethyl)adenine and about 1.2–2.2 molar equivalents of sodium alkoxide.

In an embodiment, synthesis of 9-[2-(diethylphosphonomethoxy)ethyl]adenine, shown in Diagram A, Step 3, is described as follows. In a reactor having an inert atmosphere, e.g., nitrogen, a slurry of 9-(2-hydroxyethyl)adenine (1.0 kg) and DMF (4.79 kg) is warmed to about 130° (125–135°) for 30–60 minutes. The reactor contents are rapidly cooled with vigorous agitation to about 25° (20–30°) and sodium tert-butoxide (0.939 kg) is added in portions over about 1–3 hours while maintaining vigorous agitation and the contents temperature at about 25° (20–30°). The agitation and temperature is maintained for about 15–45 minutes after all sodium tert-butoxide has been added. Then the reactor contents are cooled to about −10° (−13 to 0°) and a solution of diethyl p-toluenesulfonyloxymethyl-phosphonate (2.25 kg on a pure basis) in DMF (1.22 kg) is added over about 5–10 hours. The mixture is kept at about −5° (−10 to 0°) until the reaction is complete, which is typically about 0.5–2 hours after the final portion of diethyl p-toluenesulfonyloxymethyl-phosphonate has been added. Reaction completion is monitored by HPLC (not more than 3% 9-(2-hydroxyethyl)adenine remaining). Glacial acetic acid (0.67 kg) is added, with the pot temperature controlled to no more than 20°. The mixture at about 22° (15–25°) is agitated for about 15–45 minutes. The quenched mixture is concentrated in vacuo until distillation stops and the contents are then cooled to below 40°. Dichloromethane (16.0 kg) is added and the contents at 20° (15–25°) are agitated for at least 1 hour. If the DMF content versus total solids (NaOTs (sodium tosylate), NaOAc, Et$_2$PMEA) is greater than 20% (by $^1$H NMR) the mixture is concentrated in vacuo until distillation stops, the contents are cooled to below 40° C., dichloromethane (16 kg) is added and the reactor contents at about 20° (15–25°) are agitated for at least 1 hour. Diatomaceous earth (0.5 kg) is added and the contents, which are at about 20° (15–25°), are agitated for at least 1 hour. The solids are removed by filtration and rinsed 3 times with $CH_2Cl_2$ (about 1 kg each). The filtrate and rinses at no more than 80° are concentrated in vacuo until distillation stops, the reactor contents are cooled to below 40°, dichloromethane (5.0 kg) is added to the residue and the contents at about 25° (20–40°) are agitated to dissolve the solids. The resulting solution at no more than 80° is concentrated in vacuo until distillation stops. Dichloromethane (7.0 kg) is added and the contents at about 25° (20–40°) are agitated to dissolve the solids. If the DMF content compared to diethyl PMEA is greater than 12%, the mixture at no more than 80° is concentrated in vacuo, the contents are cooled to below 40°, dichloromethane (7.0 kg) is added and the contents at about 25° (20–40°) are agitated to dissolve the solids. The mixture is washed with water (0.8 kg) at about 25° (22–30°) by agitating for about 15–45 minutes. The phases are allowed to separate for 4 hours and the phases are then separated. The aqueous phase is back-extracted twice with dichloromethane (1.5 kg per wash) by agitation for about 15–45 minutes with the solution maintained at about 25° (22–30°), followed by allowing the phases to separate for at least 2 hours. The combined organics at no more than 80° are then concentrated in vacuo until distillation stops. Toluene (3.0 kg) is added, agitated at about 25° (22–30°) for about 15–45 minutes and the resulting mixture at no more than 80° is azeotroped in vacuo. Toluene (3.0 kg) is added and the mixture is heated to about 80° (75–85°), agitated for about 15–45 minutes, cooled to below 30° over about 60–90 minutes and then cooled to about 0° (−3 to 6°). After at least 12 hours at about 0° with slow agitation, the resulting slurry is filtered and the filter cake is rinsed three times with cold (about 0–6°) toluene (about 0.2 kg per rinse). The wet cake is dried in vacuo at about 50° (35 to 65°) and the dried product is milled. Product drying is monitored for water removal (no more than 0.3% water detected by KF titration). The inert atmosphere is maintained throughout step 3.

Methods for PMEA Synthesis

In an embodiment, synthesis of PMEA, shown in Diagram A, Step 4, is described as follows. In a reactor having an inert atmosphere, e.g., nitrogen, a mixture of diethyl PMEA (1.00 kg), acetonitrile (2.00 kg), and bromotrimethylsilane (1.63 kg) is heated to and maintained at reflux for about 1–3 hours with agitation, until the reaction is complete. Reaction completion is monitored by $^{31}$P NMR or HPLC (no diethyl PMEA and no more than 2% monoethyl PMEA detected). The solution at ≦80° C. is distilled in vacuo to a semi-solid, which is taken up in water (2.00 kg) and warmed to about 55° C. (52–58° C.) for about 30–60 minutes with agitation to dissolve all solids. The resulting mixture is cooled to about 22° C. (19–25° C.), adjusted to pH 3.2 with aqueous sodium hydroxide, the contents are heated to about 75° C. (72–78° C.) until the consistency thins (about 15–120 minutes), cooled to about 3° C. (0–6° C.), and stirred for at least 3 hours (3–6 hours). The slurry is filtered and the filter cake is rinsed with water (1.00 kg). The wet cake is suspended in water (3.75 kg) and the suspension is heated to about 75° C. (72–78° C.) with vigorous stirring. After stirring for about 2 hours, the slurry is cooled to about 3° C. (0–6° C.) and stirred for at least another 2 hours. The slurry is filtered and the filter cake is rinsed sequentially with two portions of water (0.50 kg per rinse) and two portions of acetone (1.00 kg per rinse). The isolated solid is dried in vacuo at no more than about 90° C. to a low water content (no more than 0.5% water detected by KF titration), to provide PMEA as white crystals. The product is milled to a fine particle size.

Methods for AD Synthesis

An exemplary method to prepare AD comprises suspending 1 molar equivalent of PMEA in a volume of about 5.68–56.8 equivalents of NMP/equivalent PMEA and, after one suspends the PMEA, adding about 2–5 molar equivalents, often about 2.5–3.5, usually about 3 molar equivalents, of triethylamine ("TEA") to the solution using mild to moderate agitation. One then adds about 3–6 molar equivalents, often about 4.5–5.5 molar equivalents, usually about 5 equivalents, of chloromethyl pivalate to obtain a reaction mixture. We usually prepare the reaction mixture at room temperature. One heats the reaction mixture to maintain a temperature of less than 66°, typically about 28–65°, usually between about 55–65° for about 2–4 hours to conduct the reaction. The time needed to heat the reaction mixture to about 28–65° is not critical and can vary depending on the reaction mixture volume and the capacity of the apparatus used to heat the mixture. Mild or moderate agitation maintains solids in suspension during the reaction and this minimizes extensive splashing of the reactants in the reaction vessel. This method results in a product comprising AD produced by the process of reacting the listed reactants, typically under the given conditions.

In an embodiment, conversion of PMEA to AD, shown in Diagram A, Step 5, is described as follows. In a reactor having an inert atmosphere, e.g., nitrogen, a mixture of 1-methyl-2-pyrrolidinone (3.15 kg), PMEA (1.00 kg), triethylamine (1.11 kg), and chloromethyl pivalate (2.76 kg) is heated to about 60±3° C. (no more than 66° C.) and stirred using moderate agitation for ≦4 hours (1–4 hours) until the reaction is complete, as indicated by $^{31}P$ NMR or HPLC (no more than 15% mono(POM)PMEA). The mixture is diluted with isopropyl acetate (12.00 kg), cooled to 25±3° C., and agitated for about 30 minutes. The solids are removed by filtration and washed with isopropyl acetate (5.0 kg). The combined organics are washed twice with water (3.70 kg per wash) by moderately agitating the mixture at a mixture temperature of 25±3° C. for about 15–45 minutes. The combined aqueous washes are back-extracted twice with isopropyl acetate (4.00 kg per extraction) at a mixture temperature of 25±3° C. by agitation for 15–45 minutes. The combined organics at 25±3° C. are washed with water (1.80 kg) by agitation for 15–45 minutes and then the organics at about 35±5° C. (no more than 40° C.) are concentrated in vacuo to approximately 40% of the original volume. After a polishing filtration (1 μm filter), and a rinse forward with 1.5 kg of isopropyl acetate, the concentration of the organics in vacuo is resumed until a pale oil remains the organics at about 35±5° C. (no more than 50° C.). The oil typically comprises about 6–45% AD, usually about 30–42%.

Methods for AD Crystallization

AD Crystallization from the organic oil is usually accomplished by (1) using a relatively low volume of NMP in the AD synthesis reaction as compared to the amount of PMEA present as a reactant, i.e., less than about 10 mL NMP per gram PMEA, and/or (2) by minimizing the amount of isopropyl acetate that remains entrained in the organic oil after vacuum distillation by allowing sufficient time for vacuum distillation, i.e., usually at least about 4–6 hours. The aggregate of reaction starting materials, e.g., NMP or PMEA, in the oil can account for about 2–20% of the crystallization solution, but generally less than about 1–2%. When crystals are prepared from organic oil, about 20–45%, often about 30–42%, and usually about 35–42% of AD is present in the oil before adding crystallization solvents.

One optionally crystallizes AD optionally from a supersaturated solution. Nucleation occurs in such supersaturated solutions, and readily leads to crystal formation. Nucleation rates typically increase when the degree of supersaturation and the temperature increases. Supersaturated solutions typically are prepared by changing the temperature (usually decreasing it), solvent evaporation or altering solvent composition, e.g., by adding a miscible nonsolvent or poor solvent. Combinations of these methods also generate supersaturated AD solutions, e.g., using evaporation under reduced pressure to both cool the solution while increasing the solute concentration.

Crystalline AD is prepared by allowing crystal formation in an AD composition, usually from a solution of AD in a crystallization mixture containing at least about 6%, typically at least about 30%, usually at least about 35%, of AD. One would ordinarily conduct crystallizations by preparing an AD solution comprising about 6–45% AD and about 55–94% crystallization solvent. The upper limit of solubility of AD is about 10–41% for most crystallization solvents at room temperature. AD is not freely soluble in some crystallization solvents, e.g., AD solubility in di-n-butyl ether is less than about 0.3 mg/mL, and adding these solvents to an AD solution increases the degree of saturation or supersaturation of the solution. One usually uses organic solutions containing an amount of AD that is near the upper solubility limit in the crystallization solvent(s). The lower amount, about 6%, is the minimum amount of AD needed in a solution to consistently yield crystals. Certain solvents, e.g., methanol or $CH_2Cl_2$, can contain more than about 50% AD.

The temperature at which crystallization is conducted is not critical and can vary, as the crystallization process usually proceeds spontaneously over a range of temperatures. Crystallization at temperatures above about 35°, especially about 45–50° may result in reduced yield and/or in an increase in impurities associated with the crystals. Crystallizations are generally conducted at temperature ranges of about −5° to about 50°, often about 0–35°, usually about 4–23°. One can optionally use crystallization temperatures below about −5° to increase the crystal yield or to enhance the crystal formation rate, but a low temperature process may result in increased by-products. Thus it is generally more convenient and economic to use solvents either at approximately ambient temperatures (about 15–23°) or at the typical cooling temperatures that most cooling apparatus or methods can easily reach (about 0–4°). When a solution contains relatively low concentrations of AD, i.e., about 10–20%, crystallization at a relatively low temperature, i.e., about 0–15° will often enhance crystal yields.

Heating the solution containing AD and crystallization solvent(s) to a point above room temperature, preferably to about 35°, appears to facilitate crystallization, presumably by increasing the nucleation rate. The time to heat the crystallization mixture to about 35° is not critical and can vary according to the capacity of the apparatus used, generally over a period of about 20–45 minutes. Heating is then discontinued and the temperature is reduced by cooling or by allowing the temperature to fall for about 10–120 minutes. During this time, crystals form and continue to form over a period of at least about 4–36 hours. Crystallization usually begins immediately or shortly after the crystallization mixture has reached 35°. We usually conduct crystallizations by allowing the temperature to fall to about 0–23° C. after the solution reaches 35°. Crystallizations conducted with or without mild to moderate agitation, typically with mild agitation, routinely give good results.

Appreciable crystallization usually occurs over a period of about 5 minutes to about 72 hours and about 10–16 hours routinely give good results regardless of the solvents used. The time of crystallization is not critical and can vary, although relatively short crystallization times (about 30–90 minutes) may result in reduced AD recovery. When one adds crystallization solvents to reaction mixtures containing other organic solvents, e.g., NMP, crystallization usually begins immediately once the temperature has reached about 35° or less and the solution becomes hazy.

Crystallizations are conducted in common laboratory or manufacturing plant apparatus, e.g., round bottom flasks, Erlenmeyer flasks, stainless steel reactors or glass lined reactors. One will usually conduct the crystallizations using standard laboratory scale or commercial scale manufacturing apparatus for mechanical agitation and temperature control.

When using crystallization systems containing two different solvents, one generally adds the most polar solvent to the AD first, followed by addition of the least polar solvent. One optionally removes undissolved components, if any, from the solution after one has added the first crystallization solvent, e.g., by filtration or centrifugation. For example, when one uses acetone and di-n-butyl ether to prepare Form 1 crystals from an organic solution containing AD and components from the AD synthesis reaction, one usually adds acetone first. Similarly, one would add n-butanol before adding di-n-butyl ether or one would add ethyl acetate before di-n-propyl ether. A solution containing the first polar solvent may become hazy due to precipitation of mono (POM) PMEA which may be present. The mono(POM) PMEA can then be removed from the solution by standard physical methods, e.g., filtration or centrifugation, followed by adding the second solvent, e.g., di-n-butyl ether.

Crystallization solvents we use to prepare Form 1 crystals generally contain less than about 0.2% of water. When a significant amount of water is present in the crystallization solvent, i.e., about 1–2%, the crystallization process yields varying amounts of Form 2 crystals, that are also recovered together with Form 1 crystals. The amount of water that is present in a crystallization reaction is optionally reduced by conventional means, including using anhydrous reagents or by drying solvents using molecular sieves or other known drying agents. One optionally reduces the amount of water that might be present in organic solutions containing AD, e.g., from AD synthesis reactions containing by-products and solvents such as the organic oil described above, by using an azeotroping co-solvent such as isopropyl acetate to reduce water prior to adding crystallization solvents.

In an embodiment, crystallization of Form 1 AD, shown in Diagram A, Step 6, is described as follows. The pale oil containing AD described above is dissolved in acetone (1.0 kg), heated to 35±3° C., and diluted with di-n-butyl ether (5.00 kg) in about 4 portions while maintaining a temperature of about 32–38° C. and moderate agitation. The clear solution is cooled to about 25–30° C. over about 30–60 minutes (no more than 90 minutes), seeded with a small quantity of Form 1 AD crystals (about 5 g), and the contents are then cooled to 22±3° C. over about 30–60 minutes (no more than 90 minutes) while maintaining moderate agitation. Moderate agitation of the mixture is continued at 22±3° C. for a minimum of about 15 hours. The resulting slurry is filtered and the filter cake is washed with a premixed solution of acetone (0.27 kg) in di-n-butyl ether (2.4 kg) (1:9 v/v). The wet solids are optionally further purified by adding premixed acetone (0.57 kg) and di-n-butyl ether (4.92 kg), maintaining the temperature of the contents at 22±3° C. for about 15–24 hours with agitation. The solids are then filtered, and the filter cake is washed with premixed acetone (0.27 kg) and di-n-butyl ether (2.4 kg). The filter cake maintained at ≦35° C. (about 25–35° C.) is dried in vacuo for about 1–3 days (LOD no more than 0.5%), affording Form 1 AD as a white to off-white powdery solid. The dried product is milled.

The invention includes methods to prepare Form 2 crystals. Form 2 crystals are conveniently prepared by hydrating Form 1 crystals, although the hydrate can be obtained by crystallizing AD from crystallization solvents containing an amount of water which does not interfere with crystallization, but which provides the requisite water of hydration. The water may be present as ice, liquid water or water vapor. Typically in placed into physical contact with Form 1 crystals under conditions for formation of Form 2 crystals. Form 1 crystals are optionally contacted with water vapor in a gas such as air, carbon dioxide or nitrogen, at a relative humidity of at least about 75% to obtain complete conversion of Form 1 to Form 2 crystals. Form 1 crystals are usually contacted with air at at least about 75% relative humidity for about 1–10 days at about 18–30° or typically at room temperature to obtain complete conversion to Form 2. However, Form 1 crystals are essentially non-hygroscopic at 54% relative humidity in air at room temperature, with no increase in water content after 13 days exposure.

The process of hydrating Form 1 to Form 2 crystals generates compositions comprising a mixture of Form 1 and Form 2 AD crystals where the proportion of Form 1 AD crystals varies from about 100% to 0%, with the balance of the AD being Form 2. Thus, the proportion of Form 2 crystals increases from 0% to 100% during the conversion process. These compositions may comprise formulations such as tablets.

As noted above Form 2 crystals are also prepared by conducting AD crystallization in the presence of water, e.g., where about 2–5% water is present in the crystallization solvent(s) otherwise used to make Form 1 AD. Crystallization occurs essentially as described above for Form 1 crystals, e.g., over about 4–36 hours at about 0–23°. Such preparations can contain some Form 1 crystals, but any residual Form 1 crystals optionally are converted to Form 2 crystals by exposure to water vapor as described above, or by adding sufficient additional water to the crystallization solvent.

One usually prepares Form 3 crystals by allowing crystals to grow in an anhydrous methanol solution of AD. One obtains AD in methanol by mixing sufficient noncrystalline or crystalline AD in methanol for about 10–15 minutes at room temperature or as needed to dissolve the solid AD to obtain a solution having at least about 100–150 mg AD/mL methanol. AD solubility in methanol at room temperature is greater than 600 mg/mL. Crystallization then proceeds for about 4 to about 48 hours at a temperature of about −5° to about 25°, usually at about 0–23°.

Figure 8:

Crystals obtained using isopropyl acetate as the sole crystallization solvent typically are primarily rods which can be relatively long, i.e., measuring up to about 500 µm in length, with a few needles also present. FIG. 8 shows rod-shaped crystals about 20–500 µm in length obtained by crystallization in isopropyl acetate at temperatures above about 15°.

Crystallization from supersaturated and from saturated or some unsaturated AD solutions is optionally facilitated or enhanced by adding seed crystals of AD to the solution, but seed crystals are not mandatory. For example, Form 1 AD is obtained by adding a small amount of crystalline Form 1 AD to an organic solution as described above, e.g., organic oil to which crystallization solvent has been added, but without heating to 35°. The seeded crystals facilitate formation of Form 1 crystals. Form 2 and Form 3 crystals can similarly be obtained by seeding suitable solutions with the respective crystal form, e.g., an organic solution containing ethyl acetate and about 2% water for Form 2 crystals or a saturated solution of AD in anhydrous methanol for Form 3 crystals. The amount of crystals used for seeding are optionally varied to obtain optimal results. Generally about 0.1–01.0 g of crystals per L of AD recrystallization solution is sufficient.

One can optionally recrystallize crystalline AD as desired, e.g., to increase the purity of the crystals.

For example, one recrystallizes Form 1 AD by essentially the same methods used to prepare Form 1 crystals described above. For example, recrystallization using acetone and di-n-butyl ether is accomplished by dissolving crystalline AD in acetone, about 0.2–0.4 g/mL, at about 20–35°, followed by optionally removing undissolved components, e.g., by filtering or centrifuging the solution, which is usually hazy. An undissolved component is typically mono (POM) PMEA. One then warms the solution to about 35–40° and adds about 5.2–6.2 mL (usually about 5.7 mL) of warmed (about 35–40°) di-n-butyl ether per 0.2–0.4 g of crystals that were initially used in the recrystallization. The recrystallization mixture is then allowed to cool to room temperature over about 4–4.5 hours. The recrystallization mixture will cool to room temperature more rapidly if relatively small volumes, e.g., about 1–3 L, are used. The time to cool the mixture is not critical and can vary.

Recrystallization generally begins shortly after completion of adding and mixing the di-n-butyl ether and one then allows recrystallization to proceed for about 4–36 hours, usually about 6–24 hours. Additional yield of crystals from recrystallization at room temperature for about 4–36 hours is usually obtained by cooling the recrystallization mixture to about 4–10° and allowing the mixture to stand about 1–6 hours at the reduced temperature. Usually, the amount of AD one uses in a recrystallization will be sufficient to form a saturated or nearly saturated solution, i.e., about 0.4 g/mL using acetone. Dissolution of AD in acetone is complete in about 2–8 minutes using moderate agitation. Material remaining undissolved after this initial mixing period is removed and discarded, followed by adding the second less polar solvent of the solvent pair to the mixture containing the first crystallization solvent.

One optionally recrystallizes Form 1 crystals using a single solvent such as acetone. In this embodiment, one dissolves sufficient crystals in the solvent at room temperature, to afford a saturated or nearly saturated solution followed by removal of undissolved components. One then warms the mixture to 35° and allows it to cool as described for recrystallization using the acetone and di-n-butyl ether solvent pair.

Recrystallization of Form 2 crystals will proceed as described for recrystallizing Form 1 crystals but will use Form 2 crystals dissolved in the recrystallization solvents. The Form 1 crystals that are obtained from recrystallization are optionally converted to Form 2 crystals as described herein for conversion of Form 1 to Form 2 crystals. Recrystallization of Form 2 to Form 1 crystals may also be accomplished. In this case, molecular sieves or other solvent drying means can optionally be used to limit the amount of water that is present after the Form 2 crystals are dissolved in the first solvent and during the recrystallization process. One can also recrystallize Form 2 crystals using solvents containing about 1–2% water to directly obtain Form 2 crystals.

One conducts a Form 3 recrystallization in methanol in the same manner as described herein for preparation of Form 3 crystals. A saturated or nearly saturated methanol solution is used to prepare the crystals, i.e., at least about 0.6 g/mL AD.

One optionally prepares salts from acid addition of certain organic and inorganic acids with the basic center in adenosine of AD. One generally prepares acid salts by standard methods, including dissolving AD free base in an aqueous, aqueous-alcohol or aqueous-organic solution containing the selected acid or counterion of the acid, optionally allowing crystallization and optionally accompanied by evaporating, agitating or cooling the solution. One will usually react the free base in an organic solution containing the acid or counterion, in which case the salt usually separates directly or one can seed the solution with crystals or concentrate the solution to facilitate salt precipitation. Embodiments include solutions comprising AD, a solvent, usually a crystallization solvent, and a sulfonic acid such as a $C_{6-16}$ aryl sulfonic acid, a $C_{4-16}$ heteroaryl sulfonic acid or a $C_{1-16}$ alkyl sulfonic acid. Embodiments also include solutions comprising AD, a solvent, usually a crystallization solvent, and a carboxylic acid, such as a tricarboxylic acid, a dicarboxylic acid or a monocarboxylic acid, any of which carboxylic acids comprise about 1–12 carbon atoms.

Pharmaceutical Formulations and Routes of Administration

Invention compositions that comprise crystalline AD, typically Form 1, (hereafter referred to as the active ingredients), are administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). Generally, the invention compositions are administered orally, but compositions containing crystalline AD can be administered by any of the other routes noted above.

While it is possible for AD to be administered as a pure compound it is preferable to present it as a pharmaceutical formulation. The formulations of the present invention comprise AD, together with one or more pharmaceutically acceptable excipients or carriers ("acceptable excipients") and optionally other therapeutic ingredients. The excipient (s) must be "acceptable" in the sense of being compatible with the other ingredients of the formulation and not deleterious to the patient.

The formulations include those suitable for topical or systemic administration, including oral, rectal, nasal, buccal, sublingual, vaginal or parenteral (including subcutaneous, intramuscular, intravenous, intradermal, intrathecal and epidural) administration. The formulations are in unit dosage form and are prepared by any of the methods well known in the art of pharmacy. Such methods include the step of bringing into association the active ingredient with the carrier or excipient which constitutes one or more accessory ingredients. In general the formulations are prepared by uniformly and intimately bringing into association the active ingredient with either liquid carriers or finely divided solid carriers or both, and then, if necessary, drying or shaping the product.

Formulations of the present invention suitable for oral administration may be presented as discrete units such as sachets, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

Invention formulations include compositions comprising AD and an acceptable excipient. Such excipients include binders, diluents, disintegrants, preservatives, dispersants, glidants (antiadherents) and lubricants. Such compositions optionally comprise unit dosages, including tablets and capsules. Such compositions optionally comprise tablets containing about 5–250 mg AD, usually about 5–150 mg, including tablets comprising about 60 mg or 120 mg per tablet. Such tablets optionally comprise about 1–10% binder, about 0.5–10% disintegrant, about 50–60% diluent or about 0.25–5% lubricant. Such compositions also comprise wet granules containing liquid, e.g., water, AD and one or more acceptable excipients selected from the group consisting of binders, diluents, dispersants and disintegrants.

A tablet may be made by compression or molding, optionally with one or more accessory ingredients or excipients. Tablets will typically comprise about 5–250 mg of crystalline AD per tablet, usually about 30–120 mg and usually predominantly Form 1 AD, e.g., about 60 mg per tablet or about 120 mg per tablet of Form 1 AD, where only limited amounts, usually less than about 20%, of Form 2 crystals, other crystal types or noncrystalline AD are present. Compressed tablets may be prepared by compressing on a suitable machine, AD in a free-flowing form such as a powder or granules, optionally mixed with a binder, disintegrant, lubricant, inert diluent, preservative, surface active or dispersing agent. Molded tablets may be made by molding in a suitable machine a mixture of the powdered compound usually moistened with a liquid diluent. The tablets may optionally be coated and printed, embossed, or scored and may be formulated so as to provide slow or controlled release of the active ingredient therein. Embodiments include a product made by the process of compressing a mixture containing crystalline AD, typically Form 1 or Form 2, and an acceptable excipient, e.g., dried wet granules containing, e.g., lactose, pregelatinized starch, croscarmellose sodium, talc and magnesium stearate.

Formulations containing crystalline AD and an excipient(s) may also contain L-carnitine or salts of L-carnitine, e.g., L-carnitine-L-tartrate (2:1). Release of pivalic acid from the pivaloyloxymethyl moiety of AD in vivo appears to lower the levels of L-carnitine in patients. Tablets containing L-carnitine-L-tartrate and AD may decrease the effect of pivalic acid on L-carnitine depletion in patients taking AD. The amount of L-carnitine to be included will be apparent to the clinician in view of the extent of depletion in patients.

Typical formulation ingredients for tablets or related dosage forms include one or more binders, diluents, disintegrants or lubricants. These excipients increase formulation stability, facilitate tablet compression during manufacture or formulation disintegration after ingestion. The tablets are typically made by wet granulation of one or more excipients with AD in a mixture, followed by wet milling the granules and drying to a loss on drying of about 3% or less. A binder such as pregelatinized starch or povidone, which enhances processing, is optionally present at a level of about 1–10%. A disintegrant such as microcrystalline cellulose or a cross-linked cellulose such as coscarmellose sodium is optionally present at a level of about 0.5–5% to facilitate tablet dissolution. A diluent such as a monosaccharide or disaccharide is optionally present at a level of about 40–60% to mask the physical properties of AD or to facilitate tablet dissolution. A lubricant such as magnesium stearate, talc or silicon dioxide is optionally present at a level of about 0.25–10% to facilitate tablet ejection during manufacture. The tablets may optionally contain scavengers such as lysine or gelatin to trap formaldehyde that may be released on storage of AD. Excipients have been described, e.g., Monograph for "Pregelatinized Starch", Handbook of Pharmaceutical Excipients, Second Edition, American Pharmaceutical Association, 1994, pp: 491–493; Monograph for "Croscarmellose Sodium", Handbook of Pharmaceutical Excipients, Second Edition, American Pharmaceutical Association, 1994, pp: 141–142; Monograph for "Lactose Monohydrate", Handbook of Pharmaceutical Excipients, Second Edition, American Pharmaceutical Association, 1994, pp: 252–261; Monograph for "Talc", Handbook of Pharmaceutical Excipients, Second Edition, American Pharmaceutical Association, 1994, pp: 519–521; Monograph for "Magnesium Stearate", Handbook of Pharmaceutical Excipients, Second Edition, American Pharmaceutical Association, 1994, pp: 280–282.

Typical containers for storage of Form 1 AD formulations will limit the amount of water that is present in the container. Typically unit formulations or dosages are packaged with a desiccant such as silica gel or activated carbon, or both. The containers are typically induction sealed. Silica gel packaging alone is a sufficient desiccant for storage of tablets containing AD at ambient temperature. AD contains two pivaloyloxymethyl moieties per molecule. Silica gel is thus suitable as a single desiccant for compounds such as therapeutic agents that contain one or more pivaloyloxymethyl moieties. Water permeation characteristics of containers have been described, e.g., Containers—Permeation, Chapter, USP 23, United States Pharmacopeial Convention, Inc., 12601 Twinbrook Parkway, Rockville, Md. 20852, pp: 1787 (1995).

For infections of the eye or other external tissues, e.g. mouth and skin, the formulations are preferably applied as a topical ointment or cream containing the active ingredient(s) in an amount of, for example, 0.01 to 10% w/w (including active ingredient(s) in a range between 0.1% and 5% in increments of 0.1% w/w such as 0.6% w/w, 0.7% w/w, etc), preferably 0.2 to 3% w/w and most preferably 0.5 to 2% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the wax together with the oil and fat make up the emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is suitably present in such formulations in a concentration of 0.01 to 20%, in some embodiments 0.1 to 10%, and in others about 1.0% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal or inhalational administration, wherein the carrier is a solid, include a powder having a particle size for example in the range 1 to 500 microns (including particle sizes in a range between 20 and 500 microns in increments of 5 microns such as 30 microns, 35 microns, etc). Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration are sterile and include aqueous and non-aqueous injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as recited above, or an appropriate fraction thereof, of an active ingredient.

In addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition to cats, dogs, horses, rabbits and other animals and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing a matrix or absorbent material and as active ingredient one or more compounds of the invention in which the release of the active ingredient can be controlled and regulated to allow less frequent dosing or to improve the pharmacokinetic or toxicity profile of the compound. Controlled release formulations adapted for oral administration in which discrete units comprising one or more compounds of the invention can be prepared according to conventional methods.

All references cited herein are expressly incorporated by reference with specificity.

EXAMPLES

The following examples further exemplify and do not to limit the invention.

Example 1

Preparation of Form 1 Crystals

To a 500 mL single-neck round bottom flask equipped with a magnetic stirring bar was added PMEA (27.3 g, 100 mmol). To this was added, under nitrogen, N-methylpyrrolidinone (109.3 mL) and triethylamine (50.6 g, 69.8 mL, 500 mmol), and the resulting suspension stirred vigorously. Chloromethyl pivalate (75.2 g, 72.0 mL, 500 mmol) was added and the stirring suspension was placed in a 45° oil bath for 18.5 hours. The resulting thick, light yellow suspension was diluted with isopropyl acetate (1.0 L) and stirred for 1 hour. The solid was removed by filtration (a Kimax glass funnel with a "C" glass frit) and washed with more isopropyl acetate (250 mL). The wash was combined with the filtrate and this organic phase extracted with water (200 mL×2). The aqueous extracts were combined and back-extracted with isopropyl acetate (250 mL×2). All organic phases were combined, and measured 1975 mL. Isopropyl acetate was added to bring the total volume of the organic phase up to 2.0 L. For the purpose of an internal control on this experiment, the organic phase was divided into two equal, 1.0 L portions. One portion was worked-up using a brine wash and sodium sulfate treatment while the other portion was processed without these steps (see below).

The 1.0 L organic phase sample for this new procedure was concentrated to an oil directly using a standard (Büchi) rotary evaporator employing a bath temperature of 45° and a vacuum of 50–70 mm throughout the procedure. The weight of the oil was 32.4 g, and it appeared perfectly clear, with no visible salts present. The oil was diluted with acetone (25 mL) and again a perfectly clear solution resulted with no visible precipitated salts present. After standing at room temperature for about 3 hours, the solution still remained perfectly clear. This solution was placed in an oil bath set at 45° C. and di-n-butyl ether (140 mL) was added slowly, keeping the internal temperature near 40° C. The flask was then removed from the oil bath and allowed to cool to room temperature and stirred at room temperature for about 16 hours resulting in the precipitation of Form 1 AD. The solid product was collected by filtration (a Kimax glass funnel with a "M" glass frit). The solid was washed with a 10% acetone in 90% di-n-butyl ether solution (v/v) (40 mL) and dried in a vacuum oven for 12 hours (ambient temperature, nitrogen bleed, 28" vacuum). This yielded 12.2 g (48.8% theoretical yield, based on a 50 mmol reaction scale) of a white solid, identified (HPLC) as AD of 99.8% purity versus external standard.

The remaining 1.0 L of organic phase was used as control for the above results, and was worked-up as follows. This organic phase was washed with brine (25 mL), dried over sodium sulfate (25 g, 12 hours drying time), and concentrated as described above. This afforded 27.4 g of an oil, which was crystallized as described above from acetone (25 mL) and butyl ether (135 mL). The solid was collected by filtration and dried as described above, affording 12.3 g (48.9% theoretical yield) of a white solid, identified (HPLC) as AD of 98.7% purity versus external standard.

Example 2

Preparation of Form 1 Crystals 9.7 kg of NMP at room temperature was added to 3 kg of PMEA in a 30 gallon glass-lined steel reactor vessel (Pfaudler, Rochester, N.Y., model No. P20-30-150-115) and the mixture was moderately agitated after NMP was added. The moderate agitation used was sufficient to maintain solid PMEA in suspension and prevent splashing of reactor contents on the walls. 5.6 kg of TEA was then added, followed by addition of 8.3 kg of chloromethyl pivalate. An additional 2.7 kg of NMP was then added to wash residual materials from the transfer lines used to feed the reactor. The temperature was adjusted to about 48° and the temperature was maintained between 38–48° for 18 hours with moderate agitation. After the reaction was complete, 48 kg of isopropyl acetate at room temperature was added to the reactor and the resulting mixture, under moderate agitation, was maintained for 1 hour at 43–48°, before filtration to remove the solids (Tyvek™ filter, 15.5" diameter, Kavon Filter Products, Wall, N.J., model No. 1058-D). The 30 gallon vessel was washed forward through the filter with 12 kg of additional isopropyl acetate. The filtrate was transferred to a 50 gallon glass-lined steel reactor vessel (Pfaudler, model No. P24-50-150-105) while maintaining the temperature at 43–48°. The temperature was allowed to drop to ambient during subsequent steps.

The mixture was then washed with 22 kg of water by vigorous agitation for about 1.5–2 minutes. Agitation was discontinued and the phases were allowed to completely separate (about 10 min). The lower aqueous phase (about 26 L) was transferred to the 30 gallon glass-lined steel reactor vessel. Another 22 kg of water was added to the organic phase left in the 50 gallon reactor and the phases were vigorously agitated for about 1.5–2 minutes. Agitation was discontinued and the phases were allowed to completely separate (about 1 hour 40 min). The lower aqueous phase was transferred to the 30 gallon glass-lined steel reactor vessel which now contained both aqueous washes. 24 kg of isopropyl acetate was added to the aqueous washes in the 30 gallon reactor and the phases were vigorously agitated for about 1.5–2 minutes, followed by discontinued agitation for sufficient time to obtain complete phase separation (about 10 min). The upper organic phase was retained and mixed with the organic phase previously retained in the 50 gallon reactor. 24 kg of isopropyl acetate was added to the aqueous washes in the 30 gallon reactor and the phases were vigorously agitated for about 1.5–2 minutes, followed by discontinued agitation for sufficient time to obtain complete phase separation (about 20 min). The upper organic phase was retained and mixed with the organic phase previously retained in the 50 gallon reactor. The combined organic phases were then washed with a brine solution (7 kg water, 3.9 kg NaCl) by vigorous agitation for about 1.5–2 minutes followed by discontinued agitation to allow the phases to completely separate (about 5 min). The brine phase was discarded. 18 kg of sodium sulfate was added to the reactor and the mixture was agitated vigorously for about 1.5–2 minutes and then allowed to stand for 1 hour. The organic phase weighed 98.5 kg at this point.

The reactor contents were then gently agitated and filtered through a bag filter (American Felt and Filter Co, model No. RM C S/S 122). The organic solution containing AD was transferred to a clean 50 gallon reactor and the volatile organics were removed by vacuum distillation at 33°–41° C. at a vacuum of 26–30" Hg until 50–55 L of condensate had collected. The organic phase was transferred from the 50 gallon reactor to a clean 30 gallon reactor via vacuum filtration through a cartridge filter (Memtec America, Corp., model No. 910044) containing a cotton spun wound cartridge and washed forward with 8.6 kg of isopropyl acetate. The solution was held overnight at 5° then concentrated under a vacuum at 26°–41° for 3 hours to obtain about 7–9 L of oil. 5.4 kg of acetone was added to the oil which yielded a clear solution. The solution was then agitated and warmed to 43° C. and 27 kg of room temperature di-n-butyl ether was added over a period of about 4 minutes followed by warming to return the temperature to 43° C. An additional 15 kg of di-n-butyl ether was added over about 4 minutes and the temperature was returned to 43°–44° C. at which time the temperature was allowed to drop to 20° C. over about 7 hours 15 minutes. During this time AD crystals formed in the reactor. The crystals were recovered by filteration (Nutche filter) and dried. 2.40 kg of AD was obtained (45.1%).

Example 3

Preparation of Form 1 Crystals

A 3 neck, 12 L, round bottom flask was charged with 546.3 g PMEA (2 mole), followed by 2.18 L of NMP at room temperature. Slow mechanical agitation was initiated (sufficient to keep solid PMEA suspended but without splashing flask contents) to suspend the PMEA and 1.39 L of TEA was then charged to the flask, followed by addition of 1.44 L of pivaloyloxymethyl chloride. The flask was then purged with nitrogen and the reaction was heated to 60° C. over 30–45 minutes. Gentle agitation was maintained for 2–2.5 hours with the reaction at 60°. Completion of the reaction was determined by HPLC. The reaction was terminated by charging the flask with 7.48 L of cold (0–3°) isopropyl acetate when the yield of AD reached 65–68% by area normalization. The agitation was increased to moderate agitation (moderate vortex but no splashing of contents) and the mixture remained at room temperature for 30 minutes under moderate agitation while solids (e.g., TEA.HCl mono (POM) PMEA) precipitated from the solution.

The reaction mixture was then filtered using a glass-sinter funnel (40–60 μm) and the filter cake was washed with 2.51 L of isopropyl acetate at room temperature.

The filtrate was then extracted twice with 2.0 L of potable water at room temperature. The combined aqueous phases were back extracted twice with 2.51 L of isopropyl acetate (room temperature). All organic phases were combined and extracted once with 985 mL of potable water. The organic phase was isolated and concentrated in vacuo for about 1–2 hours at a temperature of 35–39° at a vacuum of about 30 mm Hg to obtain 1.24 kg of yellow oil.

The oil was transferred to a 3 neck, 12 L flask and cooled to room temperature over about 30 minutes. The flask was charged with 628 mL of room temperature acetone and then with 3.14 L of di-n-butyl ether. Slow agitation was initiated and the solution was heated to 35° over about 5–20 minutes. When the temperature reached 35°, heating was discontinued and no further temperature increase occurred. The solution was cooled to below 30° (20–29°) over about 30 minutes. During the cooling period Form 1 crystals formed in the crystallization mixture while slow agitation was maintained, followed by continued slow agitation for 14–20 hours at room temperature. The crystals were then filtered (Tyvek™ filter) and the filter cake was washed with 2 L of a 10% acetone, 90% di-n-butyl ether (v/v) solution. The cake was dried at room temperature in a drying oven with a nitrogen bleed until a constant weight was achieved (about 2 days).

The yield of Form 1 AD obtained was 50–54% of the theoretical yield from PMEA and the purity was 97–98.5% by HPLC by area of normalization.

Example 4

Preparation of Form 1 Crystals

A 3 neck, 3 L, round bottom flask was charged with 273.14 g PMEA (1 mole), followed by 1.09 L of NMP at room temperature. Slow mechanical agitation was initiated (sufficient to keep solid PMEA suspended but without splashing flask contents) to suspend the PMEA and 0.418 L of TEA (3 equivalents) was then charged to the flask, followed by addition of 0.72 L of pivaloyloxymethyl chloride (5 equivalents). The flask was then purged with nitrogen and the reaction was heated to 60° C. over 30–45 minutes. Gentle agitation was maintained for 2–2.5 hours with the reaction at 60°. Completion of the reaction was determined by HPLC. The reaction was terminated by charging the flask with 3.74 L of cold (0–3°) isopropyl acetate when the yield of AD reached 68–70% by area normalization. The agitation was increased to moderate agitation (moderate vortex but no splashing of contents) and the mixture was allowed to stand at room temperature for 30 minutes with the moderate agitation while solids (e.g., TEA.HCl, mono(POM)PMEA) precipitated from the solution. The reaction mixture was filtered using a glass-sinter funnel (40–60 μm) and the filter cake was washed with 1.26 L of isopropyl acetate (room temperature). The filtrate was then extracted twice with 1.01 L of potable water at room temperature for each extraction. The combined aqueous phases were back extracted twice with 1.26 L of isopropyl acetate (room temperature). All organic phases were combined and extracted once with 492 mL of potable water. The organic phase was isolated and concentrated in vacuo for about 1–2 hours at a temperature of 35–39° at a vacuum of about 30 mm Hg to obtain 0.6 kg of yellow oil. The oil was transferred to a 3 neck, 3 L flask and cooled to room temperature by allowing the temperature to fall over about 30 minutes. Then the flask was charged with 314 mL of acetone (room temperature) and then charged with 1.57 L of di-n-butyl ether. Slow agitation was initiated and the solution was heated to 35° over about 5–20 minutes. When the temperature reached 35°, heating was discontinued and no further temperature increase occurred. The solution was cooled to below 30° (20–29°) over about 30 minutes. During the cooling period Form 1 crystals formed in the crystallization mixture while slow agitation was maintained. An additional volume of 1.15 L of room temperature di-n-butyl ether was added to the crystallization mixture. Moderate agitation was continued at room temperature for about 16 hours. The crystals were then filtered (Tyvek™ filter) and the cake was washed with 1 L of a 10% acetone, 90% di-n-butyl ether (v/v) solution and this solution was then removed by filtering. The cake was dried at room temperature in a drying oven with a nitrogen bleed until a constant weight was achieved (about 2 days).

The yield of Form 1 AD obtained was 55–58% of the theoretical yield from PMEA and the purity was 99–100% by HPLC by area of normalization.

Example 5

Preparation of AD Crystals Using Isopropyl Acetate as the Crystallization Solvent 43.7 mL of NMP at room temperature was added to PMEA (10.93 g) under nitrogen in a 500 mL 3 neck flask fitted with a stirring apparatus. The mixture was stirred to suspend the PMEA. TEA (27.9 mL) at room temperature was then added, followed by addition of pivaloyloxymethyl chloride (28.9 mL) at room temperature. The temperature was increased to 45° and the suspension was stirred for 12 hours at 45°. The resulting thick, yellow suspension was diluted with isopropyl acetate (150 mL) at room temperature and stirred vigorously for 75 minutes at room temperature. The solids were removed by filtration with a "C" sintered glass frit and the solids were washed with 50 mL isopropyl acetate at room temperature. The filtrates were combined and washed twice with deionized water using 40 mL per wash. The combined water washes were back-extracted twice with 40 mL isopropyl acetate per extraction. All organic phases were combined, washed once with 20 mL deionized water and the aqueous and organic phases were allowed to separate and remain in contact for 2 hours at 17°. During this time long rod-like crystals were observed to form at the aqueous-organic interface. The crystals were collected by filtration using an "M" glass sintered frit and dried, affording 512 mg of long rod-shaped crystals.

Example 6

Analysis of AD by HPLC

Crystalline Form 1 AD was analyzed by HPLC to assess purity, to isolate or identify by-products and to exemplify the use of by-products as reference standards for AD. Levels of compounds present were analyzed by the area normalization method. HPLC analyses were performed within 12 hours of standard or sample preparation.

A liquid chromatograph equipped with a fixed volume sample injector, variable wavelength absorbance detector and an electronic integrator was used with a column (Alltech Mixed Mode Anion Exchange™ C8, 7 μm, 100 Å pore size, 250 mm×4.6 mm (i.d.), Alltech, Deerfield, Ill.) and guard column (20 mm x×4.6 mm (i.d.), dry packed with Pellicular C8 particles, Alltech, Deerfield, Ill.). Chromatographic quality water was used. Chemicals used were chromatographic grade acetonitrile (Burdick & Jackson, Muskegon, Mich.) anhydrous analytical grade potassium phosphate monobasic ($KH_2PO_4$, Mallinckrodt, Paris, Ky.), anhydrous analytical grade potassium phosphate dibasic ($K_2HPO_4$, Mallinckrodt, Paris, Ky.) and A.C.S. reagent grade phosphoric acid (Mallinckrodt, Paris, Ky.). Aqueous potassium phosphate solutions were filtered (0.45 μm Nylon 66 membrane filter, Rainin, Woburn, Mass.) and degassed prior to use. Equivalents of these components and compounds can also be used. Equivalent apparatus and/or reagents can also be used to obtain similar results.

Mobile phase A, which consisted of potassium phosphate buffer, pH 6.0:acetonitrile 70:30 v/v, was prepared by mixing 1400 mL of 200 mM potassium phosphate buffer, pH 6.0 with 600 mL acetonitrile. Mobile phase B, which consisted of potassium phosphate buffer, pH 6.0:acetonitrile 50:50 v/v, was prepared by mixing 1000 mL of 200 mM potassium phosphate buffer, pH 6.0 with 1000 mL acetonitrile.

Prior to sample analysis, the HPLC column was equilibrated with mobile phase A at 1.2 mL per minute for 1 hour at room temperature. A 5 μL sample of AD (about 1 mg/mL solution) containing by-products was analyzed in a 25 minute run at room temperature and at a flow rate of 1.2 mL per minute using 100% mobile phase A for 1 minute, followed by a 19-minute linear gradient to 100% mobile phase B. The column was then held at 100% mobile phase B for 5 minutes.

The sample containing AD was prepared by accurately weighing about 25 mg of an AD sample or preparation and dissolving the AD in a final volume of 25.0 mL of sample solvent. Sample solvent was prepared by mixing 200 mL of potassium phosphate buffer (3.40 g of potassium phosphate monobasic per 1 L water, adjusted to pH 3.0 with phosphoric acid) with 800 mL of acetonitrile and equilibrating to room temperature. Compounds are identified on the basis of their elution times and/or their retention times. AD usually elutes from such a gradient at about 9.8 minutes, mono(POM) PMEA elutes at about 6.7 minutes and PMEA elutes at about 3.5 minutes.

Example 7

Physical Characterization of Form 1 Crystals

Form 1 crystals were analyzed by XRD by loading about 100 to 150 mg of crystals into an aluminum holder which was mounted into a diffractometer (GE model XRD-5 automated with a Nicolet automation package). Form 1 crystals were scanned between 4 and 35 degrees 2θ at a scan speed of 0.05° per 1.5 seconds by exposure to an X-ray generator operated at 40 KV and at −20 mA using a standard focus copper X-ray tube (Viarican CA-8) with a graphite monochromator (ES Industries) and a scintillation detector. The weighted mean value of X-ray wavelengths used for the calculations was CuKα 1.541838 Å. Form 1 AD crystals exhibit characteristic XRD peaks expressed in degrees 2θ at about 6.9, 11.8, 12.7, 15.7, 17.2, 20.7, 21.5, 22.5 and 23.3. An exemplary XRD pattern for Form 1 is shown in FIG. 1.

Figure 2:
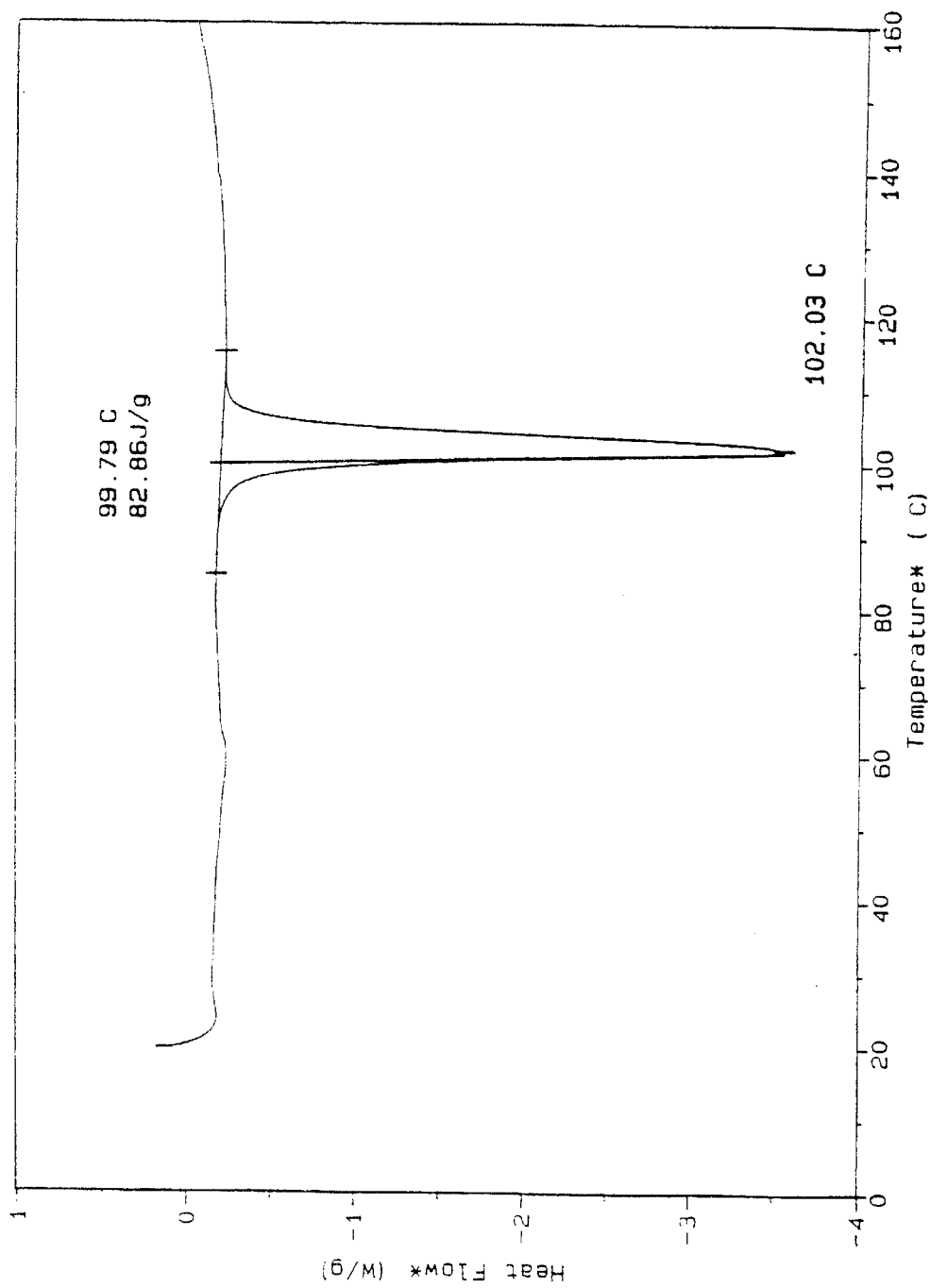
FIG. 2 shows a thermogram obtained by differential scanning calorimetry of Form 1 crystals.
Figure 3:
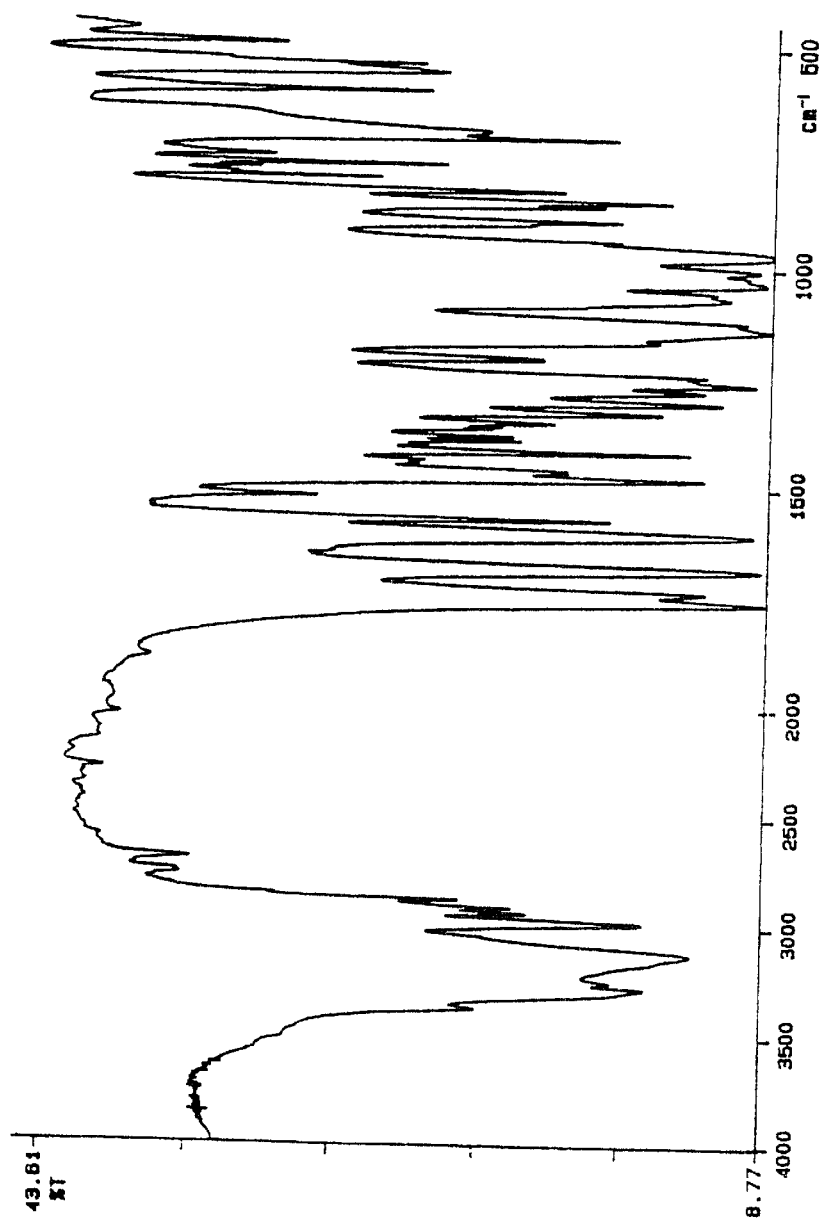
FIG. 3 shows a Fourier transform infrared absorption spectrum of Form 1 crystals.
Figure 4:
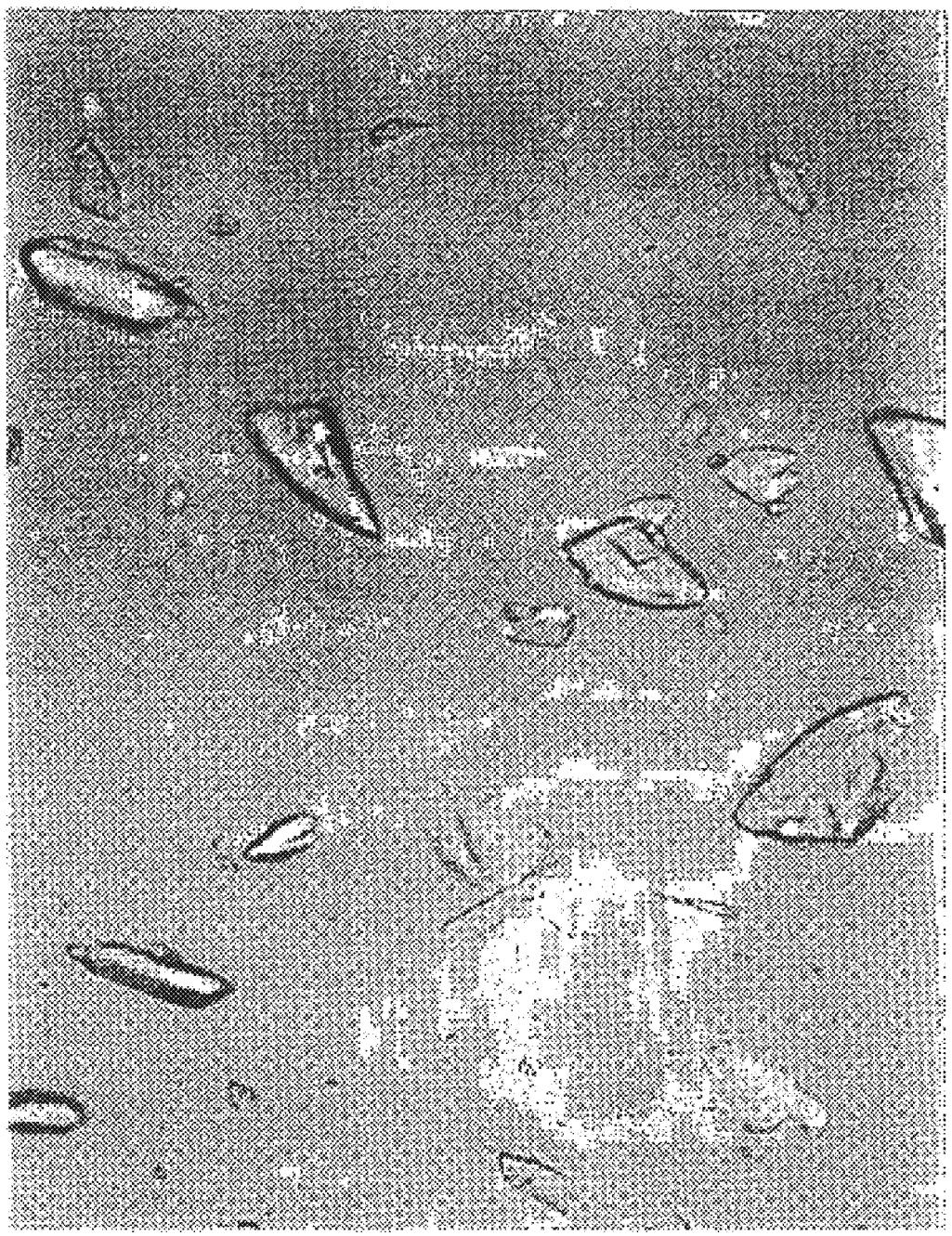
FIGS. 4–10 are pictures of a photograph showing embodiments of Form 1 crystals at 100× magnification.
Figure 5:
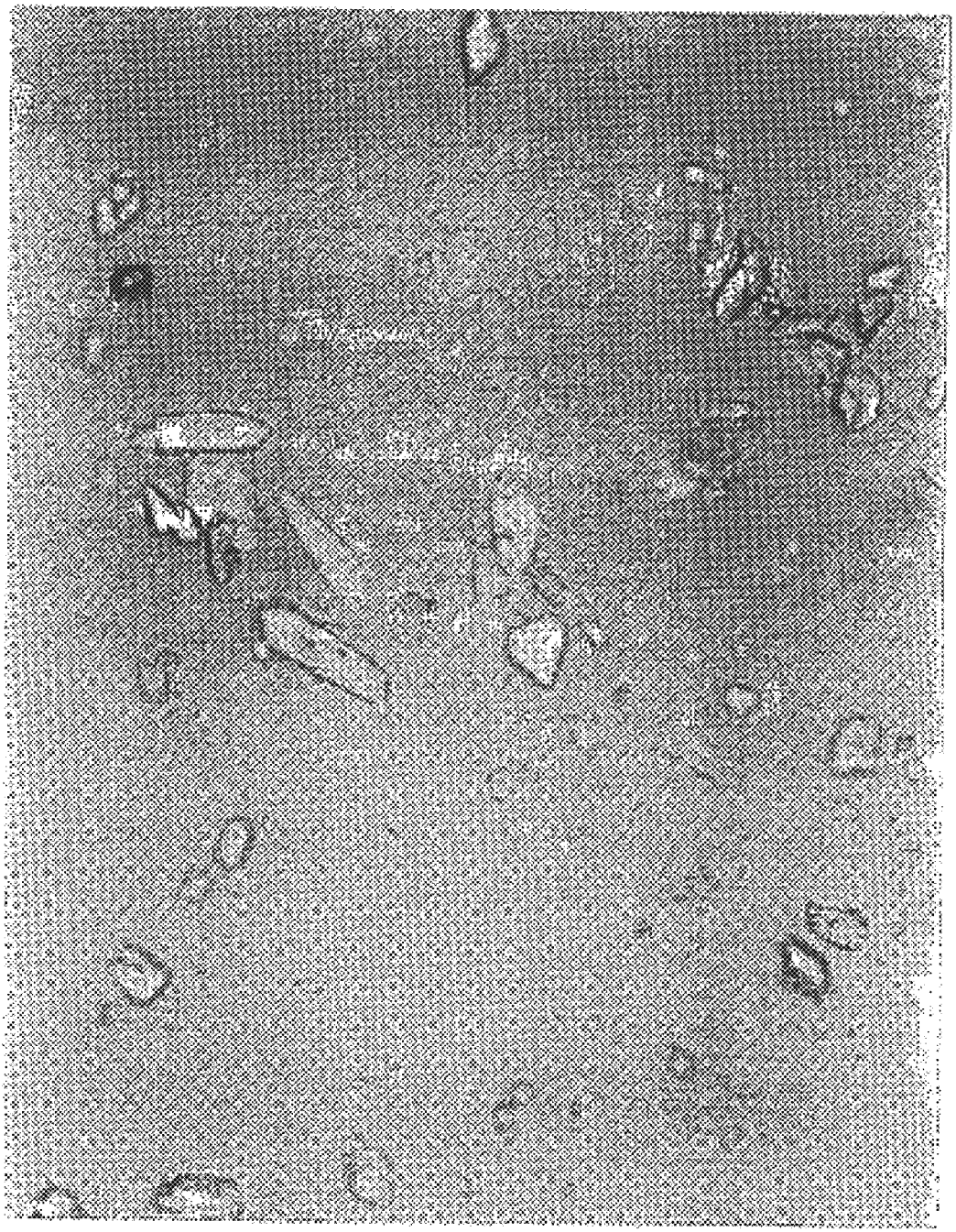
Figure 6:
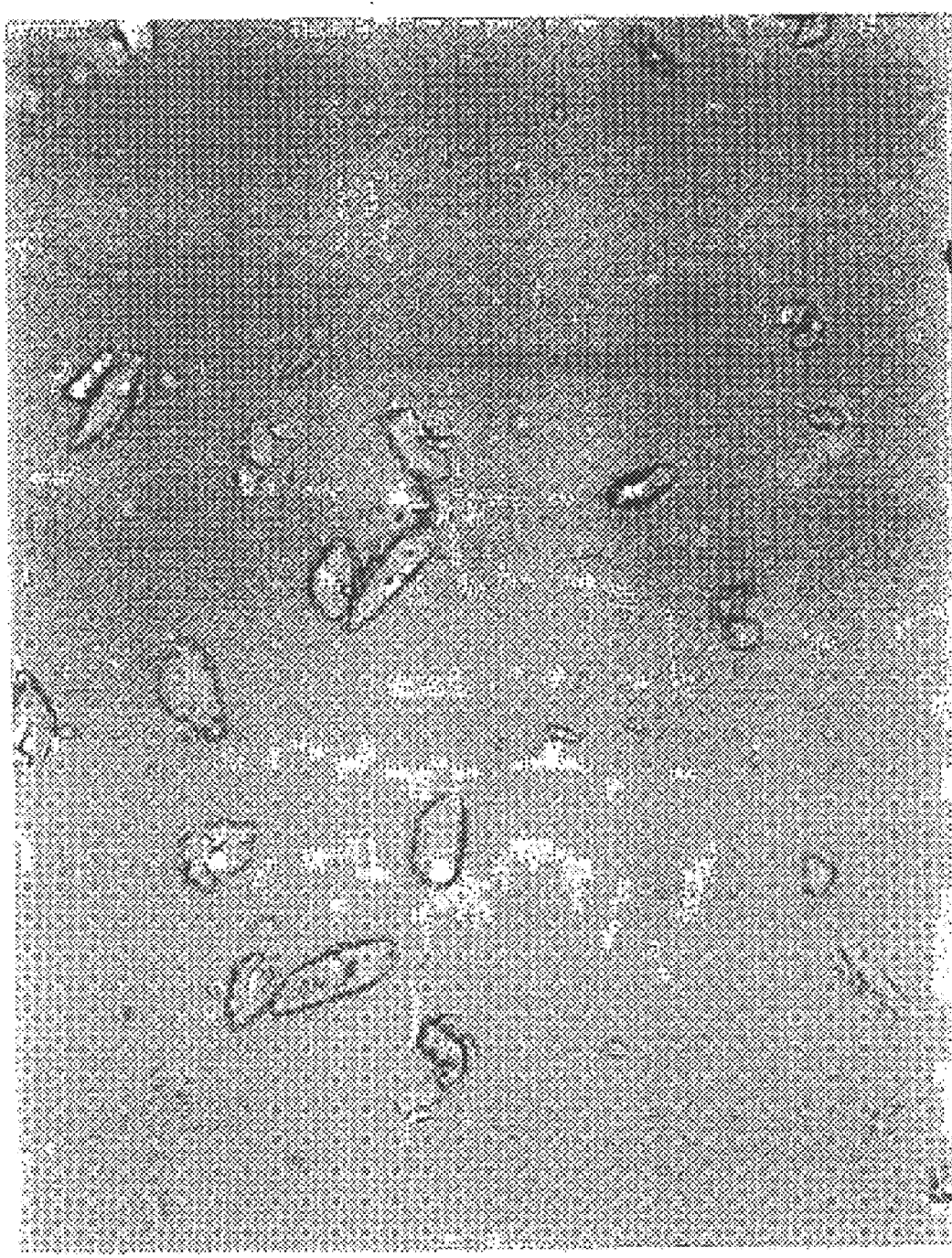
Figure 7:

Form 1 crystals were also analyzed by differential scanning calorimetry and exhibited a thermogram as shown in FIG. 2 with a characteristic endothermic transition at approximately 102.0°, having an onset at approximately 99.8°. The thermogram was obtained using a scan rate of 10° per minute under a nitrogen atmosphere. The sample was not sealed in a container in the DSC apparatus and instead was analyzed at ambient pressure in the DSC apparatus. The calorimetry scan was obtained using a differential scanning calorimeter (TA Instruments, model DSC 2910 with a model 2200 controller). Approximately 5 mg of AD was used to obtain the thermogram. Differential scanning calorimetry has been described (see, e.g., U.S. Pharmacopoeia, vol. 23, 1995, method 891, U.S.P. Pharmacopeial Convention, Inc, Rockville, Md.).

The melting point of Form 1 crystals was determined by conventional melting point analysis. The analysis was conducted using a Mettler model FP 90 Central Processor equipped with a model FP 81 measuring cell according to the manufacturer's instructions. The sample was equilibrated for 30 seconds at an initial temperature of 63° followed by a temperature increase of 1.0°/minute. Form 1 crystals melted over a range of 99.1° to 100.7°.

The infrared absorption (IR) spectrum of Form 1 crystals was obtained using a Perkin-Elmer Model 1650 FT-IR spectrophotometer according to the manufacturer's instructions. A translucent pellet containing about 10% by weight (5 mg) of Form 1 crystals and about 90% by weight (50 mg) of dried (60° C. under vacuum overnight) potassium bromide (Aldrich, IR grade) was prepared by grinding the two powders together to obtain a fine powder. IR spectroscopy has been described (see, e.g., U.S. Pharmacopoeia, vol. 23, 1995 method 197, U.S.P. Pharmacopeial Convention, Inc, Rockville, Md.; Morrison, R. T. et al, *Organic Chemistry*, 3rd ed., Allyn and Bacon, Inc., Boston, p 405–412, 1973). The spectrophotometer sample chamber was purged for at least 5 minutes with high purity nitrogen gas at about 6 p.s.i. to reduce carbon dioxide absorbance interference to ≦3% in a background scan prior to scanning with the sample. Form 1 crystals exhibited an infrared absorption spectrum in potassium bromide with characteristic bands expressed in reciprocal centimeters at approximately 3325-3275, 3050, 2800-1750, 1700, 1625, 1575-1525, 1200-1150, 1075 and 875. An exemplary infrared absorption spectrum for Form 1 is shown in FIG. 3.

Figure 9:
Figure 10:
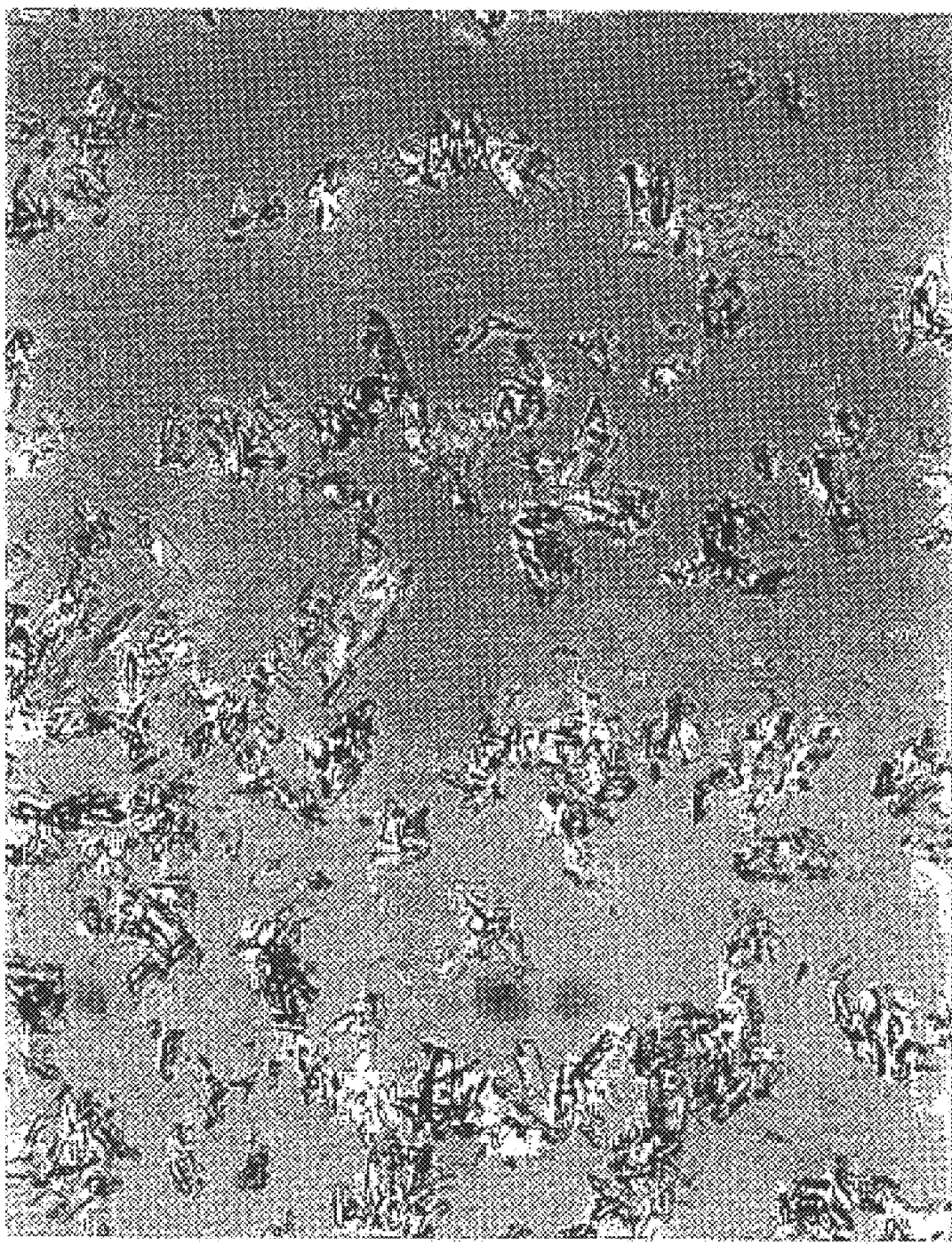

Form 1 crystals usually appear as an opaque white or off-white powder when dry. The crystals obtained from a given preparation are usually polydisperse and have a range of crystal habits including tablets, needles, plates and aggregates of tablets, needles and plates. Form 1 crystals typically range in size from about 1 μm to about 300 μm in length and are irregular tablet shaped with fractured or angular edges. Form 1 crystals obtained at low temperature, usually about 2–4°, from preparations using acetone and di-n-butyl ether as crystallization solvents are typically aggregates that comprise mostly needles and some plates. FIGS. 4–7 are photographs showing Form 1 crystals obtained from crystallization in acetone and di-n-butyl ether at temperatures above 15°. These photographs show tablet or plate-shaped and needle-shaped crystals that range in size from about 10 μm to about 250 μm in length. FIG. 9 shows Form 1 crystals obtained from crystallization in acetone and di-n-butyl ether at temperatures between about 2–4°. The photograph shows plate-shaped and needle-shaped crystal aggregates that range in diameter from about 30 μm to about 120 μm. The individual crystals in the aggregates have angular edges.

Form 1 crystals were found to have a water content of less than 1% by Karl Fischer titration. We performed the water content analysis essentially as described (see, e.g., U.S. Pharmacopoeia, 1990, pages 1619–1621, U.S. Pharmacopoeial Convention).

Example 8

Preparation of Form 2 Crystals

Form 1 crystals were converted to the Form 2 dihydrate by incubation in air at 94% relative humidity for 3 days at room temperature. During conversion of Form 1 to Form 2, a mixture of Form 1 and Form 2 crystals was obtained which increased over time from no detectable Form 2 in the initial Form 1 preparation. At the end of three days incubation, the final Form 2 preparation contained no detectable Form 1 crystals.

Example 9

Physical Characterization of Form 2 Crystals

Form 2 crystals were analyzed by XRD by the same method that was used for Form 1. Form 2 AD crystals had characteristic XRD peaks expressed in degrees 2θ at approximately 8.7–8.9, 9.6, 16.3, 18.3, 18.9, 19.7, 21.0, 21.4, 22.0, 24.3, 27.9, 30.8 and 32.8. An exemplary XRD pattern for Form 2 is shown in FIG. 11.

Figure 12:
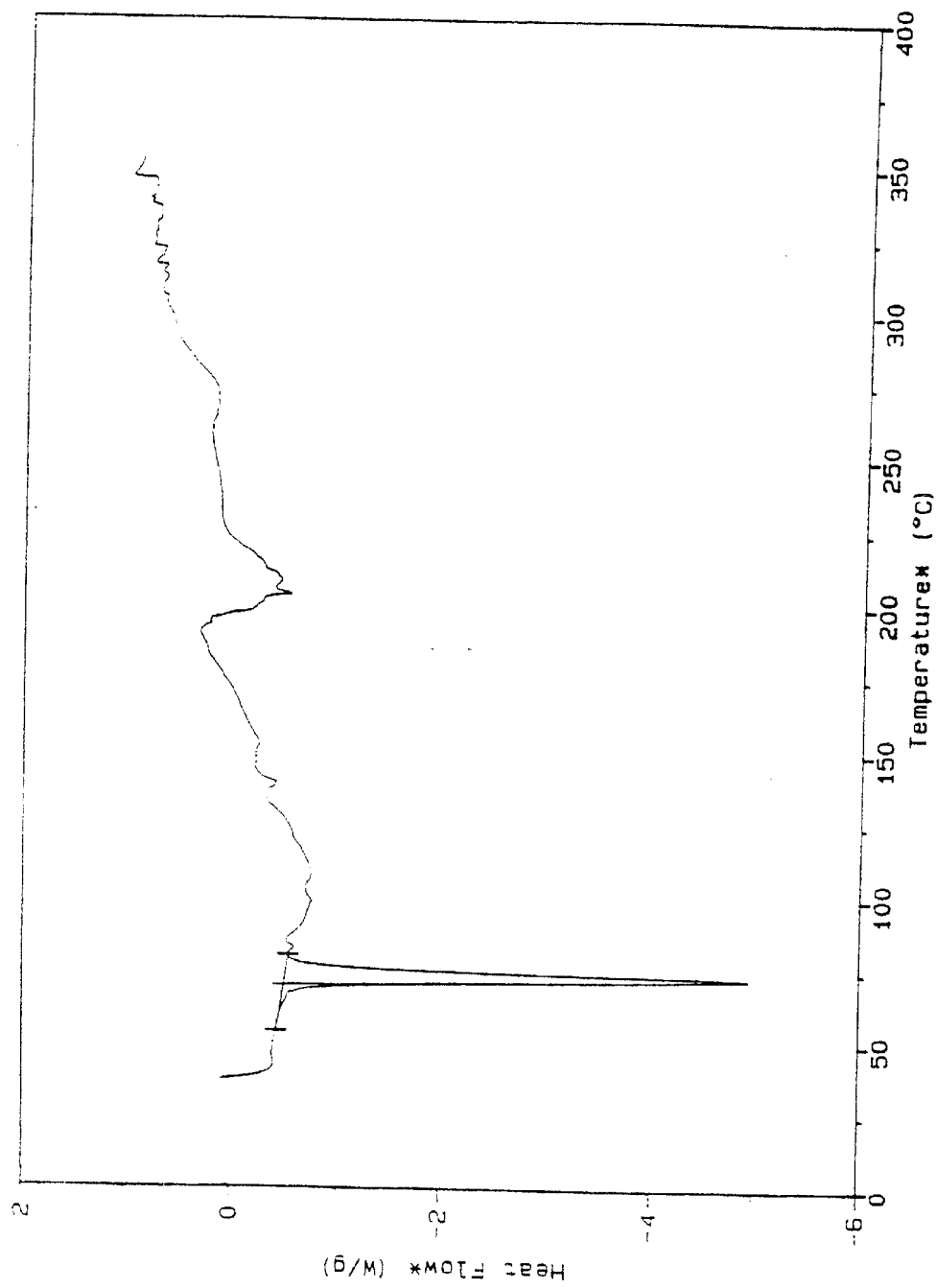
FIG. 12 shows a thermogram obtained by differential scanning calorimetry of Form 2 crystals.
Figure 13:
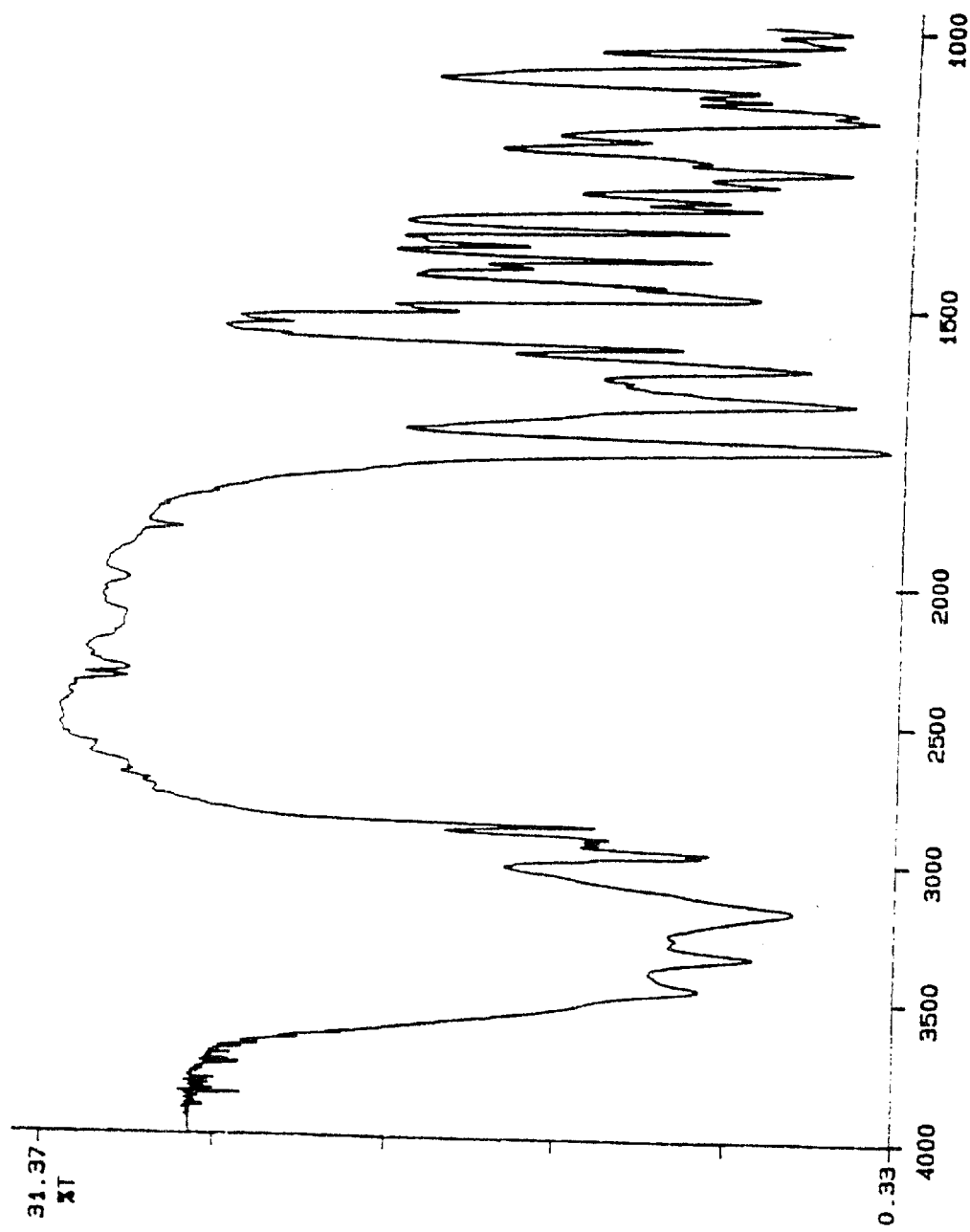
FIG. 13 shows a Fourier transform infrared absorption spectrum of Form 2 crystals.

Form 2 crystals were also analyzed by differential scanning calorimetry by the same method used to analyze Form 1 crystals and exhibited a thermogram as shown in FIG. 12 with a characteristic endothermic transition at about 72.7°, having an onset at about 69.5°.

The melting point of Form 2 crystals was determined by conventional melting point analysis. The analysis was conducted using the same method as described for Form 1. Form 2 crystals melted over a range of 70.9° to 71.8°.

The IR spectrum of Form 2 crystals was obtained using the same method as that described for Form 1 crystals. The IR spectrum is shown in FIG. 13 and exhibits the following characteristic absorption bands, expressed in reciprocal centimeters at approximately 3300–3350, 3050, 2800-1750, 1700, 1625, 1575-1525, 1200-1150, 1075 and 875. These bands are similar to those associated with Form 1 crystals, but Form 2 shows an additional O—H bond stretch band associated with water at approximately 3500.

Form 2 crystals were found to have a water content of 6.7% by Karl Fischer titration. We performed the water content analysis essentially as described (see, e.g., U.S. Pharmacopoeia, 1990, pages 1619–1621, U.S. Pharmacopoeial Convention).

Example 10

Preparation of Form 3 Crystals

Sufficient Form 1 crystals (about 250 mg) were dissolved in anhydrous methanol (about 2 mL) at room temperature to obtain a solution. The solution was obtained by mixing for about 10–15 minutes until the crystals were dissolved. The solution was allowed to stand without mixing for 10–48 hours and Form 3 crystals were then recovered from the solution.

Example 11

Physical Characterization of Form 3 Crystals

Form 3 crystals were analyzed by XRD by the same method that was used for Form 1. Crystalline Form 3 AD crystals were characterized as essentially having XRD peaks expressed in degrees 2θ at approximately 8.1, 8.7, 14.1, 16.5, 17.0, 19.4, 21.1, 22.6, 23.4, 24.2, 25.4 and 30.9. An exemplary XRD pattern for Form 3 is shown in FIG. 14.

Example 12

Synthesis and Purification of PMEA

PMEA used for AD synthesis and crystallization was purified to increase product yield and purity. A 12 L 3 neck round bottom flask containing 548.8 g of diethyl PMEA was charged with 637.5 mL of acetonitrile at room temperature. The diethyl PMEA was dissolved by moderate agitation (moderate vortex with little or no splashing of the flask contents). The flask was purged with nitrogen and 803.8 g of bromotrimethylsilane was slowly added (about 2–5 minutes). The flask contents were heated to reflux (65°) for 2 hours until $\leq 1\%$ monoethyl PMEA remained by HPLC area of normalization analysis. Volatiles were distilled off at $\leq 80°$ and ~20 mm Hg. The flask was then charged with 1500 mL of room temperature water. The pH of the solution in the flask was then adjusted to 3.2 with 25% w/v NaOH. The flask contents were then heated to 75° for 2 hours and the contents were then cooled to 3–4° over 15–20 minutes and held at 3–4° for 3–3.5 hours. The flask contents were then filtered with a glass frit filter and the cake was washed with 150 mL of cold (3–4°) water. The washed cake was transferred to a clean 12 L 3 neck flask and the flask was charged with 2025 mL of water and the flask was heated to 75° and held at that temperature for 2 hours. Heating was discontinued and the flask was cooled and held at 3–4° for 3–3.5 hours. The flask contents were then filtered with a glass frit filter and the cake was washed with 150 mL of cold (3–4°) water and then washed with 1050 mL of room temperature acetone. The cake was dried to constant weight by heating at 65–70° at ~20 mm Hg. PMEA yield was 85.4% with 99% purity by either area of normalization or external standard HPLC analysis.

Example 13

Single Crystal X-ray Crystallography of Form 1

About 200 mg of lot 840-D-1 AD drug substance was dissolved in 200 mg of acetone. The solution was heated to about 60° C. Di-n-butyl ether, at ambient temperature, was slowly added to the solution at 60° C. until the appearance of the first trace of precipitate. The mixture was then shaken and re-heated to about 60° C. to form a clear and homogeneous solution. The solution was allowed to cool to ambient temperature overnight and was held at ambient temperature for about 2 days. The resulting crystals were highly polydisperse with some having long dimensions of up to 1 mm. The supernatant was decanted and the remaining crystals were washed with a total of about 1 mL of di-n-butyl ether over four cycles to remove the residual supernatant. A crystal having approximate dimensions of 150×200×320 μm was subjected to analysis using single crystal X-ray diffraction.

All measurements were made on a Siemens SMART diffractometer (Siemens Industrial Automation, Inc., Madison, Wis.) with graphite monochromated Mo—Kα radiation ($\lambda = 0.71069$ Å). The crystal was mounted on a glass fiber using Paratone N™ hydrocarbon oil. Data acquisition was carried out at $-135 \pm 1°$ C. Frames for an arbitrary hemisphere of reciprocal space were collected using w scans of 0.3° per frame counted for 10 seconds per frame.

5967 integrated reflections, measured out to a maximum 2θ of 51.6°, were averaged to yield 3205 Friedel unique reflections ($R_{int}$=0.044). The structure was solved with the non-hydrogen atoms refined anisotropically. The hydrogen atoms were introduced in idealized positions. The final cycle of full matrix least squares refinement, based on 2438 observed reflections having I>3σ and 306 variable parameters, converged at R=0.048 ($R_w$=0.054).

Cell constants and an orientation matrix obtained from a least squares refinement using the measured positions of 3242 reflections with I>10σ in the range 3.00<2θ<45.00° corresponded to a C-centered monochnic cell specified as follows: a=12.85 Å, b=24.50 Å, c=8.28 Å, β=100.2°, Z=4, space group Cc.

Figure 27:
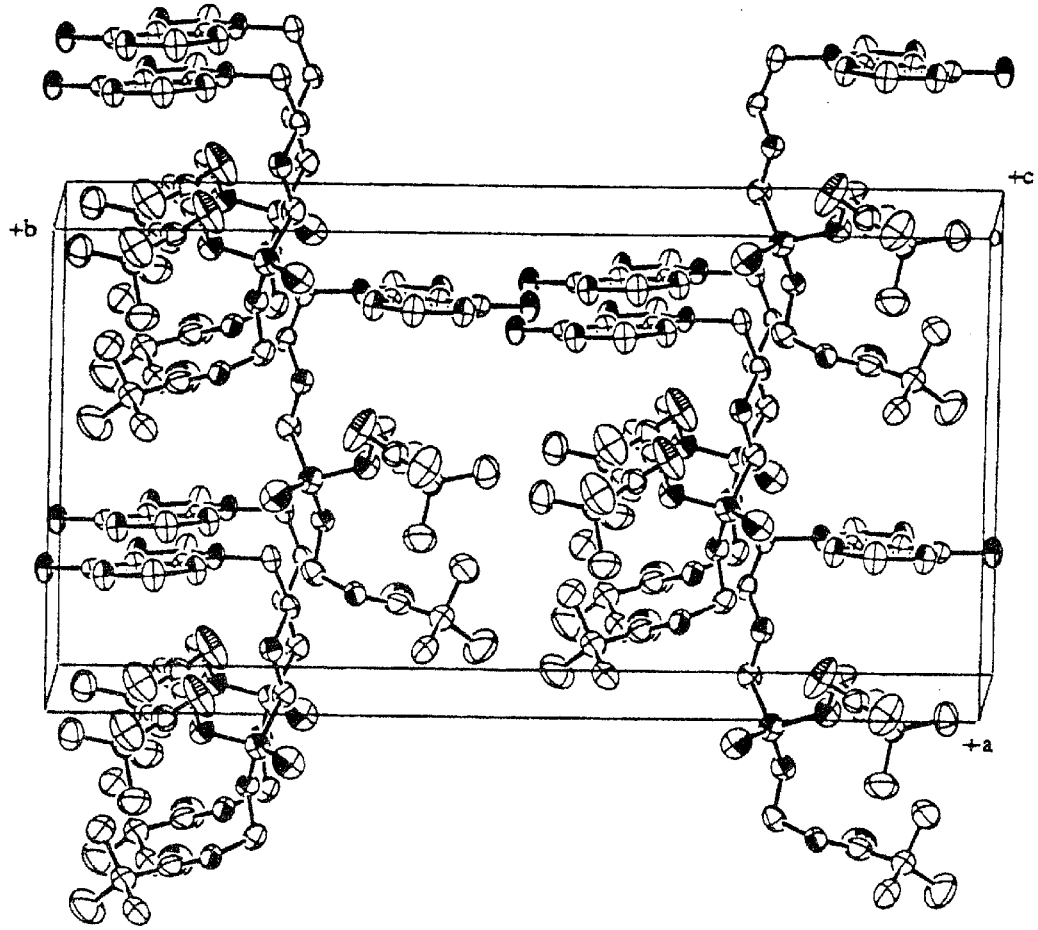
FIG. 27 is a packing diagram showing unit cell of form 1 AD.
Figure 28:
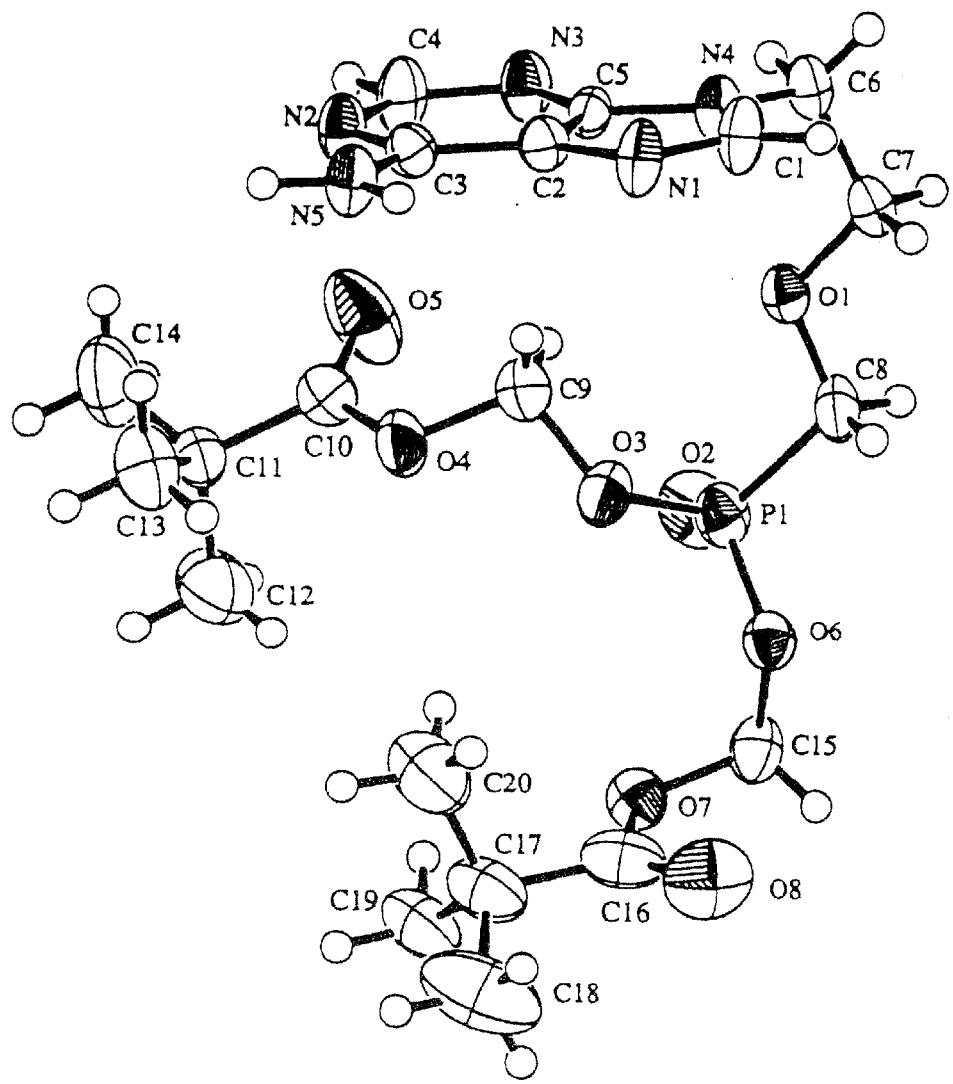
FIG. 28 is the atomic numbering scheme for form 1 AD.
Figure 29:
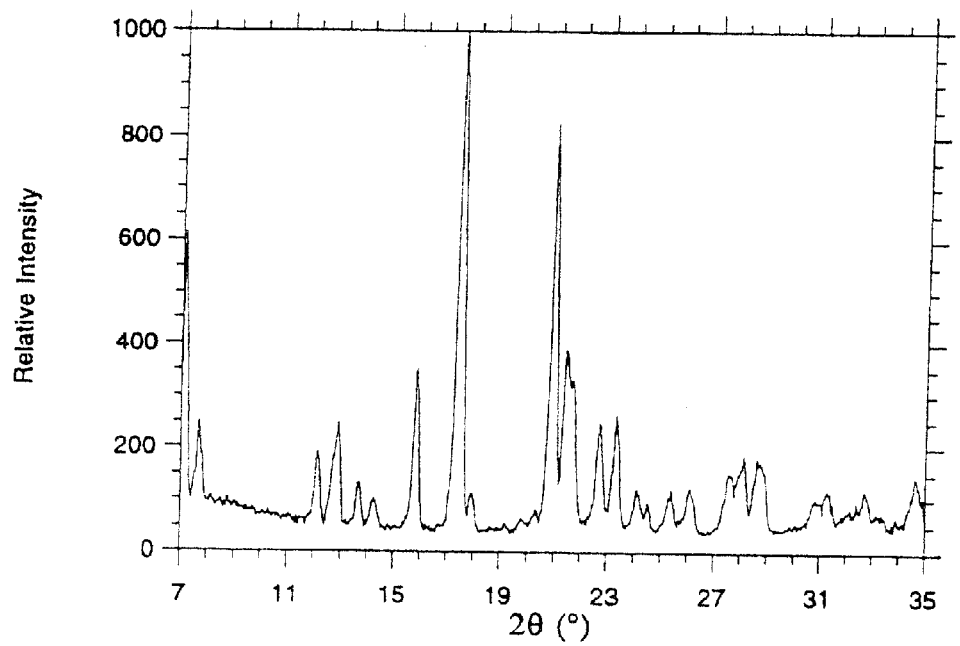
FIGS. 29($a$) and 29($b$) are the powder X-ray diffraction patterns for form 1 AD that were observed (FIG. 29($a$)) and calculated (FIG. 29($b$)).
Figure 29:
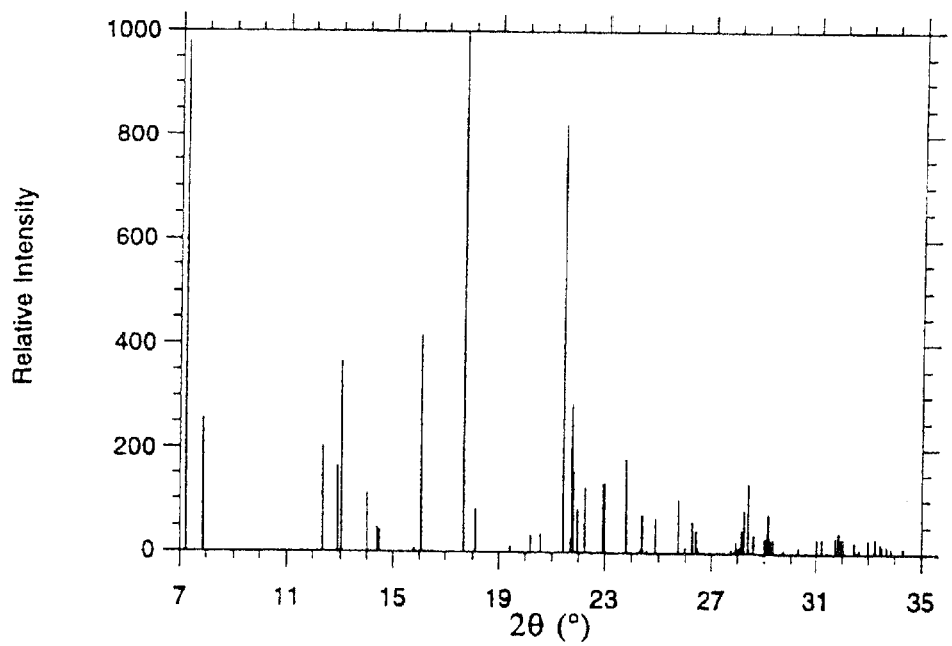

FIGS. 27, 28 and 29(a) and (b), and the following tables, show data obtained from the study.

Fractional atomic coordinates for Form 1 AD.[a]

| Atom | x | y | z |
| --- | --- | --- | --- |
| P1 | 1.0808 | 0.22760(05) | 0.6554 |
| O1 | 0.8826(03) | 0.23934(12) | 0.6880(04) |
| O2 | 1.1005(04) | 0.26242(16) | 0.5213(05) |
| O3 | 1.0440(03) | 0.16716(14) | 0.6037(05) |
| O4 | 1.0034(04) | 0.12075(16) | 0.3651(05) |
| O5 | 0.9271(05) | 0.16940(19) | 0.1501(06) |
| O6 | 1.1768(03) | 0.21530(12) | 0.7951(04) |
| O7 | 1.3179(03) | 0.17817(13) | 0.6942(04) |
| O8 | 1.3518(04) | 0.13595(19) | 0.9392(06) |
| N1 | 0.6976(04) | 0.09182(15) | 0.7806(05) |
| N2 | 0.6997(04) | 0.06321(14) | 0.3428(05) |
| N3 | 0.6929(04) | 0.15993(15) | 0.3987(05) |
| N4 | 0.6929(04) | 0.17777(13) | 0.6860(05) |
| N5 | 0.7041(04) | −0.00364(15) | 0.5388(05) |
| C1 | 0.6935(05) | 0.14417(19) | 0.8165(06) |
| C2 | 0.7000(04) | 0.09175(17) | 0.6147(06) |
| C3 | 0.7008(04) | 0.04924(19) | 0.4999(06) |
| C4 | 0.6945(05) | 0.11621(19) | 0.3029(06) |
| C5 | 0.6962(04) | 0.14452(17) | 0.5538(05) |
| C6 | 0.6968(05) | 0.23782(18) | 0.6890(06) |
| C7 | 0.8026(04) | 0.25795(18) | 0.7733(06) |
| C8 | 0.9855(05) | 0.25344(20) | 0.7701(07) |
| C9 | 0.9597(06) | 0.1557(03) | 0.4715(08) |
| C10 | 0.9798(05) | 0.1318(02) | 0.2018(07) |
| C11 | 1.0283(04) | 0.08975(19) | 0.1036(06) |
| C12 | 1.1460(06) | 0.1018(03) | 0.1244(10) |
| C13 | 1.0105(06) | 0.0329(02) | 0.1618(08) |
| C14 | 0.9783(07) | 0.0959(03) | −0.0773(08) |
| C15 | 1.2825(05) | 0.22414(20) | 0.7731(06) |
| C16 | 1.3473(05) | 0.1340(02) | 0.7942(09) |
| C17 | 1.3650(05) | 0.0841(02) | 0.6937(09) |
| C18 | 1.4337(07) | 0.0440(03) | 0.8045(12) |
| C19 | 1.4160(05) | 0.1000(02) | 0.5486(09) |
| C20 | 1.2561(06) | 0.0599(03) | 0.6340(11) |
| H1 | 0.6911 | 0.1572 | 0.9239 |
| H2 | 0.6915 | 0.1239 | 0.1897 |
| H3 | 0.7060 | −0.0145 | 0.6494 |
| H4 | 0.7044 | −0.0304 | 0.4560 |
| H5 | 0.6836 | 0.2511 | 0.5796 |
| H6 | 0.6439 | 0.2511 | 0.7458 |
| H7 | 0.8166 | 0.2445 | 0.8826 |
| H8 | 0.8025 | 0.2967 | 0.7751 |
| H9 | 0.9977 | 0.2379 | 0.8768 |
| H10 | 0.9916 | 0.2920 | 0.7786 |
| H11 | 0.9032 | 0.1380 | 0.5107 |
| H12 | 0.9346 | 0.1884 | 0.4165 |
| H13 | 1.1770 | 0.0992 | 0.2371 |
| H14 | 1.1785 | 0.0762 | 0.0630 |
| H15 | 1.1561 | 0.1377 | 0.0861 |
| H16 | 0.9367 | 0.0263 | 0.1513 |
| H17 | 1.0404 | 0.0072 | 0.0974 |
| H18 | 1.0430 | 0.0293 | 0.2736 |
| H19 | 0.9919 | 0.1315 | −0.1138 |
| H20 | 1.0079 | 0.0696 | −0.1405 |
| H21 | 0.9041 | 0.0903 | −0.0902 |
| H22 | 1.2855 | 0.2557 | 0.7074 |
| H23 | 1.3266 | 0.2293 | 0.8768 |
| H24 | 1.3999 | 0.0345 | 0.8938 |
| H25 | 1.4441 | 0.0122 | 0.7442 |
| H26 | 1.5002 | 0.0604 | 0.8454 |
| H27 | 1.4811 | 0.1181 | 0.5869 |
| H28 | 1.4288 | 0.0681 | 0.4897 |
| H29 | 1.3701 | 0.1237 | 0.4784 |
| H30 | 1.2125 | 0.0863 | 0.5708 |
| H31 | 1.2623 | 0.0287 | 0.5684 |
| H32 | 1.2254 | 0.0497 | 0.7257 |

[a]Numbers in parentheses denote standard deviation in the last significant figures Example 14

Preparation of Form 4 Crystals

Form 1 AD (10.05 g) was dissolved in isopropanol (50 mL) with warming (about 35° C.) and then filtered through a glass frit (M frit, ASTM 10–15 μm). The filtrate was added to a stirred solution of isopropanol (49 mL) at about 35° C. containing dissolved fumaric acid (2.33 g) and the mixture was allowed to passively cool to room temperature. Form 4 crystals, AD.fumaric acid (1:1) spontaneously formed in the mixture shortly after the AD solution was added to the isopropanol solution. The crystals were allowed to form for 2 days at room temperature, recovered by filtration and dried in vacuo under nitrogen at room temperature.

Example 15

Preparation of Form 4 Crystals

Form 1 AD (1005.1 g) was dissolved in warm (about 45° C.) isopropanol (3.0 L). The warm AD solution was added over about 20 minutes with moderate agitation to a stirred solution of isopropanol (6.0 L) at about 45° C. in a 12 L flask containing dissolved fumaric acid (233.0 g). The mixture temperature was maintained at 40–45° C. for 10 minutes and warming was discontinued when thick precipitate formed. Several minutes after the all of the AD solution was added, the mixture became hazy and then a few minutes later the precipitate became thick, at which point agitation was discontinued (mixture temperature 42° C.). Precipitate was allowed to form for an hour. Slow agitation was started and continued for about 2 hours, followed by immersing the 12 L flask in room temperature water with slow stirring continued overnight to facilitate mixture cooling. The precipitate was recovered by a first filtration (Tyvek™ filter) and a second filtration (M glass frit) and dried in vacuo at room temperature under nitrogen.

Example 16

Preparation of Crystalline AD Salts from Organic and Inorganic Acids

Form 1 AD (500 mg, 1.0 mmol) was dissolved in isopropyl alcohol (5 mL) with warming (<40° C.). Acid (1.0 mmol) dissolved in 2 mL of isopropyl alcohol, or a larger volume as needed to dissolve the acid, was added to the AD solution. The solution was stored in a tightly capped scintillation vial at room temperature. In some cases, precipitated salts were observed shortly after the solution was capped (about 1 minute). For other salts, precipitate began to form at times up to several months after the solution was capped. Melting points for all 13 salts is shown below. XRD data (degrees 2θ) for nine salts is also shown below. The XRD data shows most of the highest intensity peaks for these salts.

| Acid | melting point (° C.) | XRD spectrum peaks |
|---|---|---|
| hemisulfate | 131–134 | 8.0, 9.5, 12.0, 14.6, 16.4, 17.0, 17.5–17.7*, 18.3, 19.0, 20.2, 22.7, 24.1, 28.2 |
| HBr | 196–199 (decomp.) | 13.2, 14.3, 15.9, 17.8, 20.7, 21.8, 27.2, 28.1 |
| HCl | 204–205 (decomp.) | ND*** |
| HNO$_3$ | 135–136 (decomp.) | 8.0, 9.7, 14.1, 15.2, 16.7, 17.1, 18.3, 18.9, 19.4, 20.0, 21.2, 22.3, 23.2, 24.9, 27.6, 28.2, 29.4, 32.6 |
| CH$_3$SO$_3$H | 138–139 | 4.8, 15.5, 16.2, 17.5, 18.5, 20.2, 24.8, 25.4, 29.5 |
| C$_2$H$_5$SO$_3$H | 132–133 | 4.4, 8.8, 18.8, 23.0–23.3*, 27.3 |
| β-naphthylene sulfonic acid | 156–157 | 9.8, 13.1, 16.3, 17.4, 19.6, 21.6–22.3*, 23.4, 24.1–24.5**, 26.6 |
| α-naphthylene sulfonic acid | 122–128 | 8.3, 9.8, 11.5, 15.6, 16.3, 16.7–17.4**, 19.6, 21.0, 22.9, 23.7, 25.0, 26.1 |
| (S)-camphor sulfonic acid | 160–161 | 5.4, 6.5, 13.7, 15.5, 16.8–17.2*, 19.6, 20.4–20.7*, 21.2, 23.1, 26.1, 27.5, 28.4, 31.3, 32.2 |
| fumaric acid | 144–145 | ND |
| succinic acid | 122–124 | 4.7, 9.5, 10.6, 14.9, 16.3, 17.4, 17.9, 19.9, 20.8, 22.1, 23.9–24.2*, 26.5, 27.6, 28.2 |
| maleic acid | 72–75 | ND |
| ascorbic acid | 210–212 | ND |
| nicotinic acid | 192–193 | ND |

*present as two peaks or as a peak with shoulder
**3–4 peaks present in broad peak
***ND = XRD analysis not done Example 17

AD Formulation

Form 1 AD was formulated with several excipients in tablets containing 30, 60 or 120 mg AD per tablet as follows.

| | 30 mg Tablet | | 60 mg Tablet | | 120 mg Tablet | |
|---|---|---|---|---|---|---|
| Component | % w/w | mg/ tab. | % w/w | mg/ tab. | % w/w | mg/ tab. |
| Adefovir dipivoxil | 7.5 | 30.0 | 15.0 | 60.0 | 30.0 | 120.0 |
| Pregelatinized Starch, NF | 5.0 | 20.0 | 5.0 | 20.0 | 5.0 | 20.0 |
| Croscarmellose Sodium, NF[1] | 6.0 | 24.0 | 6.0 | 24.0 | 6.0 | 24.0 |
| Lactose Monohydrate, NF[1] | 74.5 | 298.0 | 67.0 | 268.0 | 52.0 | 208.0 |
| Purified Water, USP[2] | — | — | — | — | — | — |
| Talc, USP | 6.0 | 24.0 | 6.0 | 24.0 | 6.0 | 24.0 |
| Magnesium Stearate, NF | 1.0 | 4.0 | 1.0 | 4.0 | 1.0 | 4.0 |
| Total | 100.0 | 400.0 | 100.0 | 400.0 | 100.0 | 400.0 |

[1]To be incorporated into the dosage form in two portions (intragranular and extragranular) during the manufacturing process.
[2]The quantity of water added is sufficient to produce a suitable wet granulation. Water was removed to a level of not more than 3% loss on drying (LOD).

Tablets containing Form 1 AD were made by blending croscarmellose sodium, pregelatinized starch and lactose monohydrate in a granulator. Water was added and the contents were mixed in a granulator until a suitable wet granulation formed. The wet granulation was milled, dried in a dryer to a moisture content of not more than 3% loss on drying and the dried granules were passed through a mill. The milled granules were combined with extragranular excipients, lactose monohydrate, croscarmellose sodium and talc, and blended in a blender to obtain a powder blend. Magnesium stearate was added, blended in a blender, and compressed into tablets. The tablets were filled into high density polyethylene or glass bottles along with polyester fiber packing material and optionally with a silica gel desiccant.

Example 18

AD Formulation

Form 1 AD was formulated with several excipients in tablets weighing 100 mg each and containing either 25 or 50 mg AD per tablet as follows. The tablets were prepared by wet granulation in a manner similar to that described above.

| | per unit content | |
|---|---|---|
| Component | % w/w | % w/w |
| Form 1 AD | 25.0 | 50.0 |
| Lactose Monohydrate, NF | 40.5 | 26.5 |
| Microcrystalline Cellulose, NF | 31.0 | 20.0 |
| Croscarmellose Sodium, NF | 2.0 | 2.0 |
| Silicon Dioxide, NF | 0.5 | 0.5 |
| Magnesium Stearate, NF | 1.0 | 1.0 |

We claim:
1. A composition comprising crystalline adefovir dipivoxil.
2. The composition of claim 1 wherein the crystalline adefovir dipivoxil is Form 1 adefovir dipivoxil.
3. The composition of claim 2 comprising a C-centered monoclinic cell specified substantially as follows: a=12.85 Å, b=24.50 Å, c=8.28 Å, β=100.2°, Z=4, space group Cc.
4. The composition of claim 2 having an X-ray powder diffraction spectrum peak using Cu—Kα radiation, expressed in degrees 2θ at about 6.9.
5. The composition of claim 4 having a DSC endothermic transition at about 102° C.
6. The composition of claim 1 wherein the crystalline adefovir dipivoxil is Form 2 adefovir dipivoxil.
7. The composition of claim 6 having an X-ray powder diffraction spectrum peak using Cu—Kα radiation, expressed in degrees 2θ at about 9.6, about 18.3, about 22.0 and about 32.8.

8. The composition of claim 7 having a DSC endothermic transition at about 73° C.

9. The composition of claim 1 wherein the crystalline adefovir dipivoxil is Form 3 adefovir dipivoxil.

10. The composition of claim 9 having an X-ray powder diffraction spectrum peak using Cu—Kα radiation, expressed in degrees 2θ at about 8.1, about 19.4, about 25.4 and about 30.9.

11. The composition of claim 10 having a DSC endothermic transition at about 85° C.

12. The composition of claim 1 wherein the crystalline adefovir dipivoxil is Form 4 adefovir dipivoxil.

13. The composition of claim 12 having an X-ray powder diffraction spectrum peak using Cu—Kα radiation, expressed in degrees 2θ at about 9.8, about 15.2, about 26.3 and about 31.7.

14. The composition of claim 12 having a DSC endothermic transition at about 148° C.

15. The composition of claim 1 comprising a crystalline salt of adefovir dipivoxil.

16. The crystalline salt of claim 15 wherein the crystalline salt is a salt of an organic acid.

17. The crystalline salt of claim 15 wherein the crystalline salt is a salt of an inorganic acid.

18. The composition of claim 1 wherein the crystalline adefovir dipivoxil is a crystalline salt of adefovir dipivoxil selected from the group consisting of hemisulfate, hydrobromide, hydrochloride, nitrate, mesylate, ethane sulfonate, β-naphthylene sulfonate, α-naphthylene sulfonate, (S)-camphor sulfonate, succinic acid, maleic acid, ascorbic acid or nicotinic acid.

19. The composition of claim 1 comprising a pharmaceutically acceptable excipient.

20. A method comprising administering to a subject an antivirally effective amount of the composition of claim 19.

21. A method comprising contacting a crystallization solvent and adefovir dipivoxil.

22. The method of claim 21 wherein the adefovir dipivoxil is in a a solution.

23. The method of claim 22 wherein the crystallization solvent is mixed with the solution to obtain a second solution, which is allowed to form crystals.

24. A method comprising crystallizing adefovir dipivoxil from a solution comprising about 6–45% adefovir dipivoxil and about 55–94% crystallization solvent wherein the crystallization solvent is selected from the group consisting of (1) a mixture between about 1:10 v/v to about 1:3 v/v of acetone:di-n-butyl ether, (2) a mixture between about 1:10 v/v to about 1:3 v/v of ethyl acetate:di-n-propyl ether, (3) a mixture between about 1:10 v/v to about 10:1 v/v of t-butanol:di-n-butyl ether, (4) a mixture between about 1:10 v/v to about 1:3 v/v of methylene chloride:di-n-butyl ether, (5) a mixture between about 1:10 v/v to about 10:1 v/v of diethyl ether:di-n-propyl ether, (6) a mixture between about 1:10 v/v to about 1:3 v/v of tetrahydrofuran:di-n-butyl ether, (7) a mixture between about 1:10 v/v to about 1:3 v/v of ethyl acetate:di-n-butyl ether, (8) a mixture between about 1:10 v/v to about 1:3 v/v of tetrahydropyran:di-n-butyl ether, (9) a mixture between about 1:10 v/v to about 1:3 v/v of ethyl acetate:diethyl ether, (10) t-butyl-methyl ether, (11) diethyl ether, (12) di-n-butyl ether, (13) t-butanol, (14) toluene, (15) isopropyl acetate, (16) ethyl acetate, and (17) a mixture consisting essentially of (A) a first crystallization solvent consisting of a first dialkyl ether of the formula $R^1$—O—$R^2$ wherein $R^1$ is an alkyl group having 1, 2, 3, 4, 5 or 6 carbon atoms, $R^2$ is an alkyl group having 2, 3, 4, 5 or 6 carbon atoms wherein $R^1$ and $R^2$ are the same or different, or both $R^1$ and $R^2$ are linked together to form a 5-, 6-, 7-, or 8-membered ring, provided that the dialkyl ether is not methyl-ethyl ether, and (B) a second crystallization solvent selected from the group consisting of (a) a second dialkyl ether of the formula $R^1$—O—$R^2$, wherein the second dialkyl ether is different from the first dialkyl ether, (b) toluene, (c) tetrahydrofuran, (d) t-butanol, (e) ethyl acetate, (f) methylene chloride, (g) propyl acetate and (h) isopropanol.

25. A method for preparing Form 2 adefovir dipivoxil comprising forming adefovir dipivoxil crystals in the presence of water.

26. The method of claim 25 wherein the Form 2 adefovir dipivoxil is produced by (1) hydrating Form 1 adefovir dipivoxil crystals, and/or (2) crystallizing adefovir dipivoxil in the presence of water.

27. A method comprising contacting adefovir dipivoxil with methanol.

28. A method for preparing Form 4 adefovir dipivoxil comprising forming crystals comprising adefovir dipivoxil in the presence of fumaric acid.

29. A method for preparing adefovir dipivoxil comprising contacting 9-[2-(phosphonomethoxy)ethyl]adenine with chloromethyl pivalate in 1-methyl-2-pyrrolidinone and a trialkylamine and recovering adefovir dipivoxil.

30. The method of claim 29 wherein the trialkylamine is triethylamine.

31. The method of claim 30 comprising contacting 1 molar equivalent of 9-[2-(phosphonomethoxy)ethyl]adenine and about 5.6–56.8 molar equivalents of 1-methyl-2-pyrrolidinone.

32. The method of claim 29 comprising contacting 1 molar equivalent of 9-[2-(phosphonomethoxy)ethyl]adenine and about 2–5 molar equivalents of triethylamine.

33. A method comprising contacting 9-[2-(phosphonomethoxy)ethyl]adenine containing less than about 2% salt with chloromethyl pivalate.

34. The method of claim 33 wherein the salt is NaBr or KBr.

35. A product produced by the process of compressing a mixture comprising Form 1 adefovir dipivoxil and a pharmaceutically acceptable excipient.

36. The product of claim 35 wherein the compression results in a tablet.

37. A product produced by the process of preparing wet granules from a mixture comprising a liquid, Form 1 adefovir dipivoxil and a pharmaceutically acceptable excipient.

38. The product of claim 37 wherein the liquid is water.

39. The product of claim 37 wherein the process further comprises drying the wet granules.

40. A composition comprising a tablet containing adefovir dipivoxil, 20 mg pregelatinized starch, 24 mg croscarmellose sodium, lactose monohydrate, 24 mg talc and 4 mg magnesium stearate, wherein the adefovir dipivoxil comprises at least about 70% form 1 adefovir dipivoxil.

41. The composition of claim 40 wherein the tablet contains 60 mg adefovir dipivoxil and 268 mg lactose monohydrate.

42. The composition of claim 41 wherein the tablet weighs about 400 mg.

43. The composition of claim 41 wherein the adefovir dipivoxil comprises at least about 80% form 1 adefovir dipivoxil.

44. The composition of claim 40 wherein the tablet contains 120 mg adefovir dipivoxil and 208 mg lactose monohydrate.

45. The composition of claim 44 wherein the tablet weighs about 400 mg.

46. The composition of claim 44 wherein the adefovir dipivoxil comprises at least about 80% form 1 adefovir dipivoxil.

47. A method for preparing 9-[2-(diethylphosphonomethoxy)ethyl]-adenine comprising contacting sodium alkoxide and 9-(2-hydroxyethyl)adenine.

* * * * *